(12) United States Patent
Takahashi et al.

(10) Patent No.: US 8,147,403 B2
(45) Date of Patent: Apr. 3, 2012

(54) CAPSULE PROPULSION DEVICE AND PROPULSION METHOD

(75) Inventors: Masaki Takahashi, Hachioji (JP); Hironao Kawano, Machida (JP); Hironobu Takizawa, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 142 days.

(21) Appl. No.: 12/791,079

(22) Filed: Jun. 1, 2010

(65) Prior Publication Data

US 2010/0312077 A1 Dec. 9, 2010

Related U.S. Application Data

(63) Continuation of application No. PCT/JP2009/070259, filed on Dec. 2, 2009.

(30) Foreign Application Priority Data

Dec. 4, 2008 (JP) .................................. 2008-310027

(51) Int. Cl.
*A61B 5/00* (2006.01)
(52) U.S. Cl. ......................... 600/117; 600/302
(58) Field of Classification Search .................. 600/117, 600/302

See application file for complete search history.

(56) References Cited

U.S. PATENT DOCUMENTS

| 2008/0035521 | A1 | 2/2008 | Takizawa et al. |
| 2008/0300453 | A1 | 12/2008 | Aoki et al. |

FOREIGN PATENT DOCUMENTS

| JP | H01-221134 | 9/1989 |
| JP | 04-144533 | 5/1992 |
| JP | 2003-172738 | 6/2003 |
| JP | 2005-040400 | 2/2005 |
| JP | 2006-093916 | 4/2006 |
| JP | 2006-101204 | 4/2006 |
| JP | 2006-325838 | 12/2006 |
| JP | 2007-010345 | 1/2007 |
| JP | 2008-092857 | 4/2008 |
| JP | 2008-228873 | 10/2008 |
| JP | 2010-514461 | 5/2010 |
| WO | WO 2007/077768 A1 | 7/2007 |

OTHER PUBLICATIONS

Abstract only of International Publication No. WO 2008-082005 A1 (Corresponding to JP 2010-514461).
Decision on Patent Grant dated Mar. 15, 2011 with English language translation.
Japanese Office Action with English-language translation dated Jul. 27, 2010.

*Primary Examiner* — Patricia Mallari
*Assistant Examiner* — Christian Jang
(74) *Attorney, Agent, or Firm* — Smith, Scott, Murphy & Presser, P.C.

(57) ABSTRACT

A capsule propulsion device has: at least one acoustic streaming generator for generating acoustic streaming as a flow of the a medium in a space; a control unit for driving and controlling the acoustic streaming generator; and a distance obtaining unit for obtaining an object distance between the acoustic streaming generator and an object existing in the space. The control unit drives and controls the acoustic streaming generator on the basis of the distance information obtained by the distance obtaining unit.

13 Claims, 40 Drawing Sheets

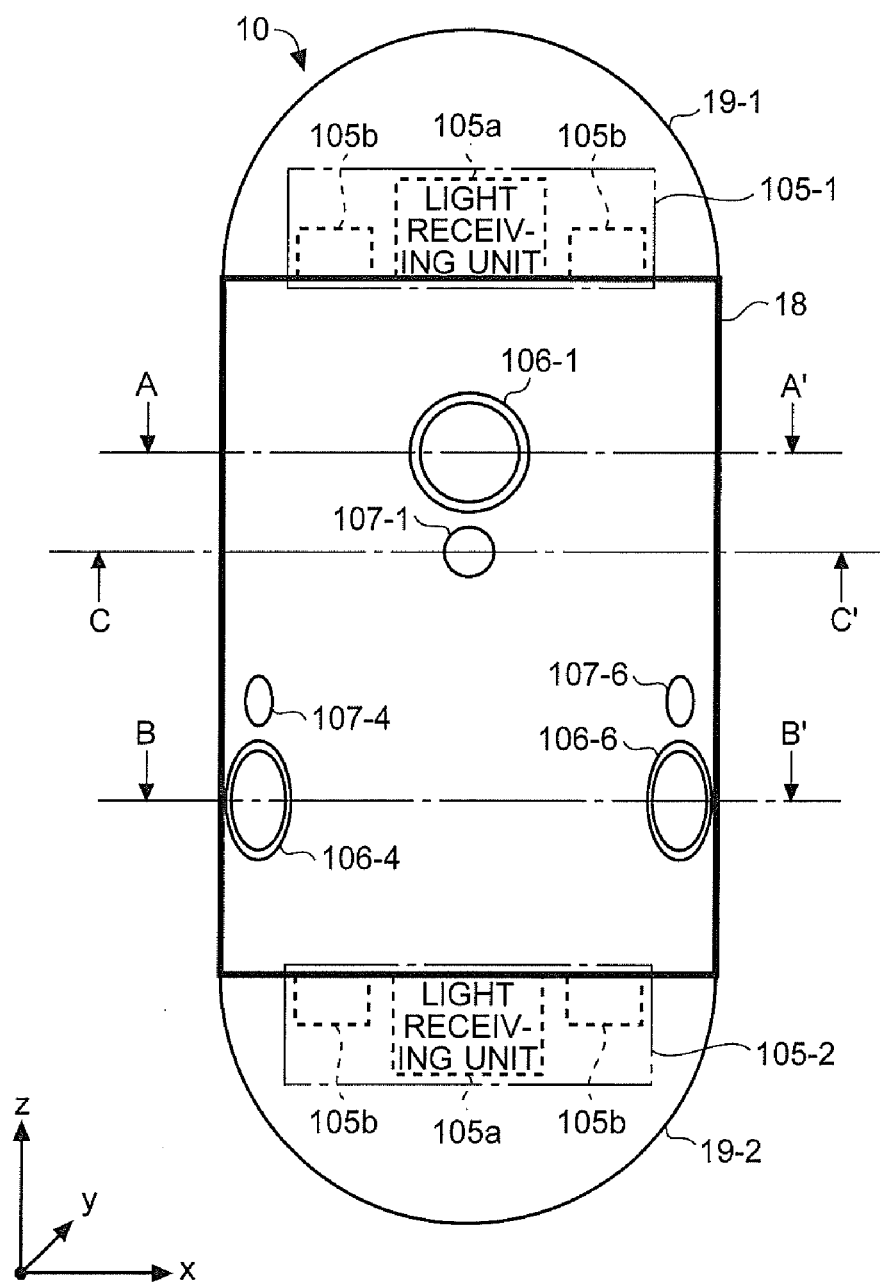

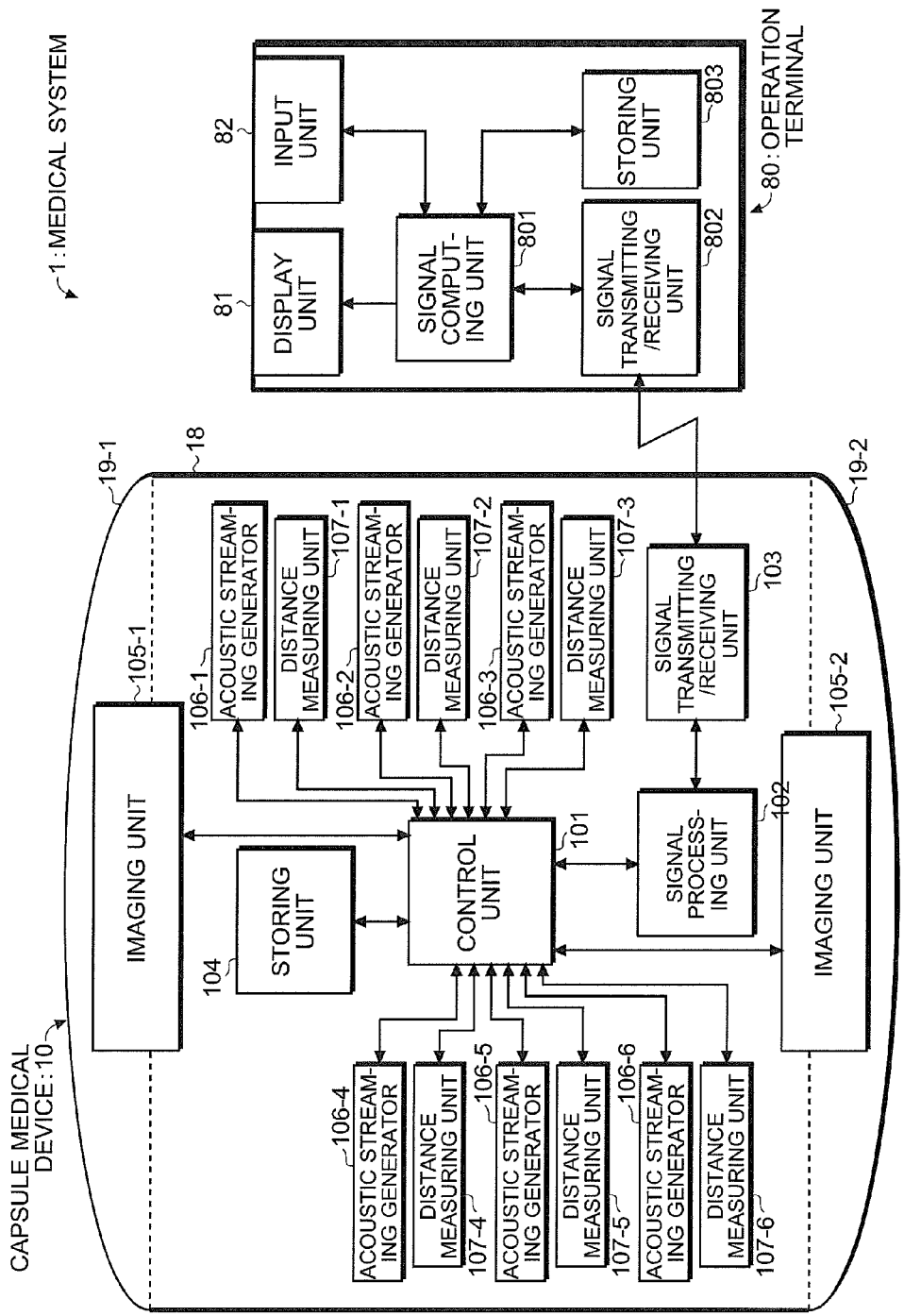

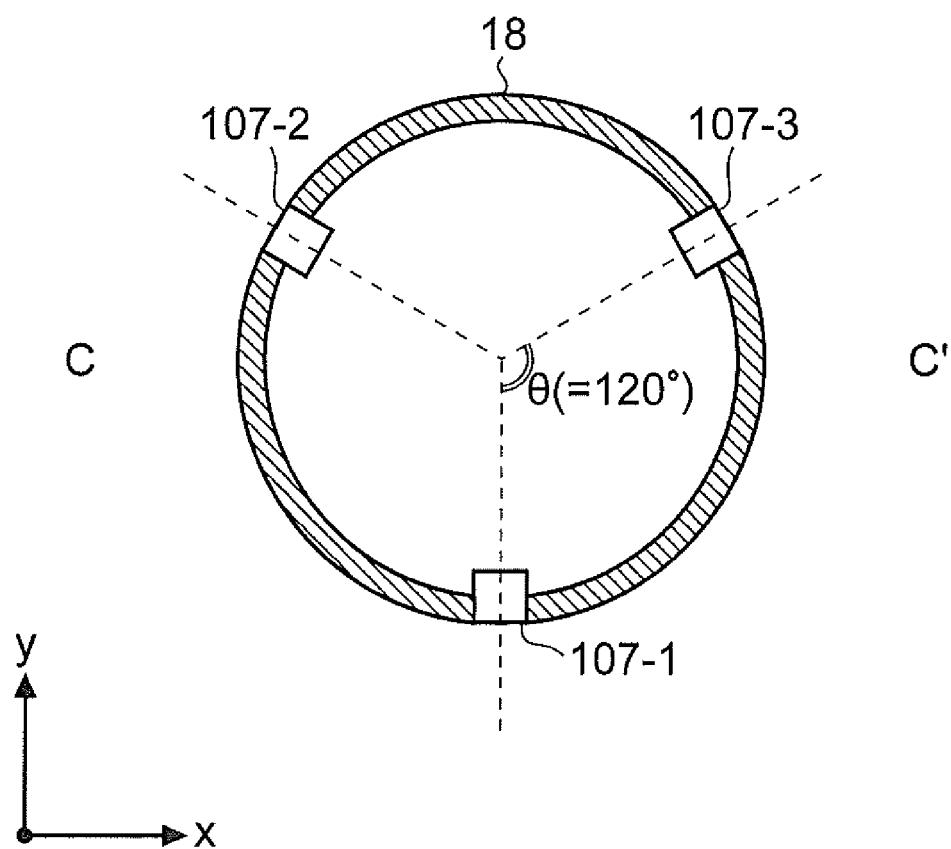

DRIVE CONTROL TABLE

| TRAVEL DIRECTION | UPPER-STAGE CONTROL INFORMATION (ID; POWER INFORMATION) | LOWER-STAGE CONTROL INFORMATION (ID; POWER INFORMATION) |
|---|---|---|
| (1,0) DIRECTION | (01;50) + (02;115.5) | (04;115.5) + (05;50) |
| (1,1) DIRECTION | (01;115.5) + (02;50) | (04;115.5) + (06;50) |
| (0,1) DIRECTION | (01;100) | (04;100) + (06;100) |
| (-1,1) DIRECTION | (01;115.5) + (03;50) | (04;50) + (06;115.5) |
| (-1,0) DIRECTION | (01;50) + (03;115.5) | (05;50) + (06;115.5) |
| (-1,-1) DIRECTION | (02;50) + (03;115.5) | (05;115.5) + (06;50) |
| (0,-1) DIRECTION | (02;100) + (03;100) | (05;100) |
| (1,-1) DIRECTION | (02;115.5) + (03;50) | (04;50) + (05;115.5) |

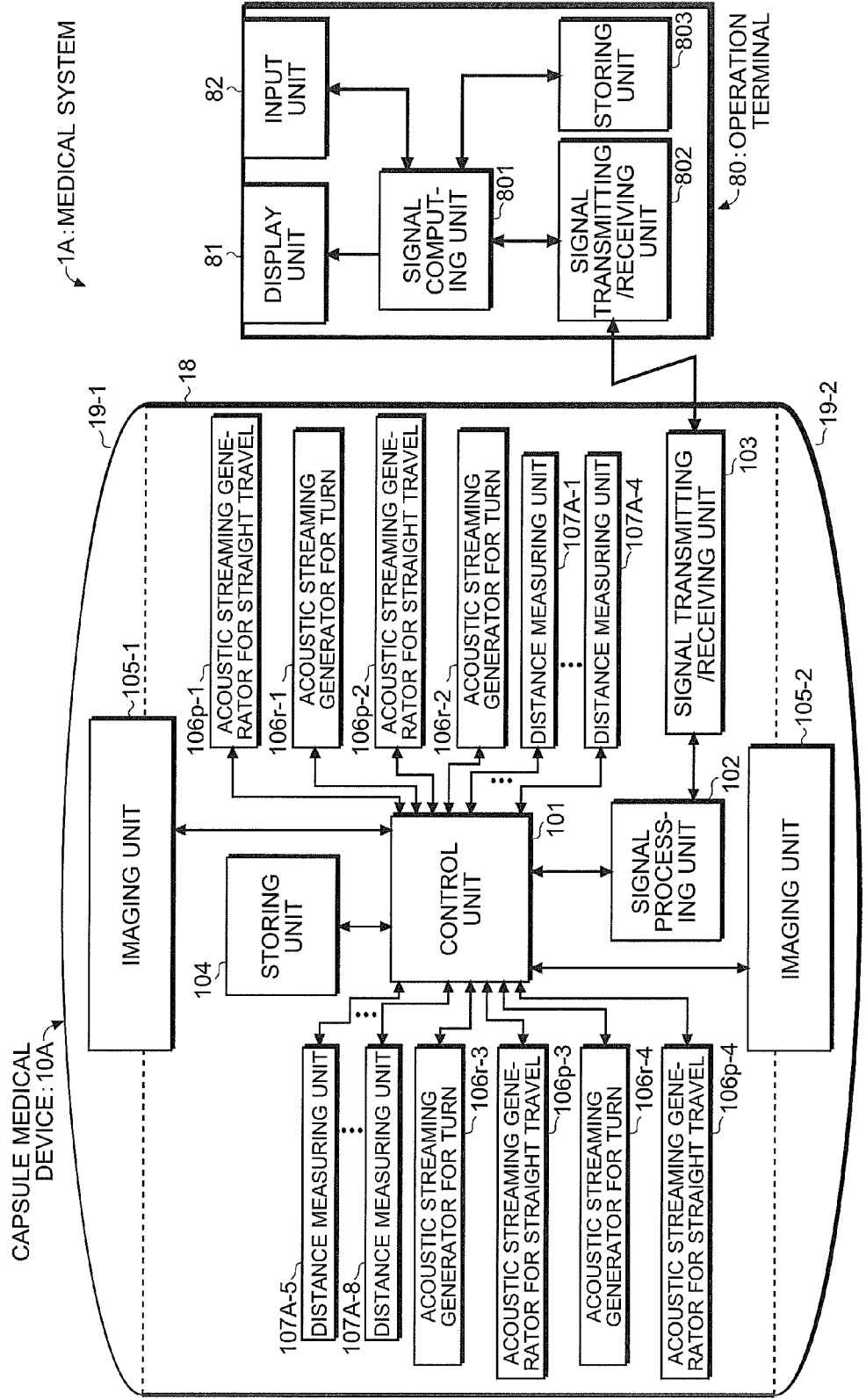

CAPSULE PROPULSION DEVICE AND PROPULSION METHOD

CROSS-REFERENCE TO RELATED APPLICATIONS

This application is a continuation of PCT international application Ser. No. PCT/JP2009/070259 filed on Dec. 2, 2009 which designates the United States, incorporated herein by reference.

BACKGROUND OF THE INVENTION

1. Field of the Invention

The present invention relates to a capsule propulsion device and propulsion method and, more particularly, to a capsule propulsion device and propulsion method capable of obtaining a propulsion force by generating acoustic streaming.

2. Description of the Related Art

For example, in the medical field, Japanese Unexamined Patent Application Publication No. 4-144533 discloses a swallow-type capsule medical device having an information obtaining function of obtaining various information of the inside of a subject when the device is introduced in the subject such as a human or animal and a wireless communication function of transmitting/receiving the obtained information, a control signal from the outside, and the like via radio waves. Japanese Unexamined Patent Application Publication No. 4-144533 also discloses a capsule medical device capable of traveling in a subject by generating acoustic streaming by vibrating a piezoelectric element which can be operated from the outside.

SUMMARY OF THE INVENTION

A capsule propulsion device according to an aspect of the present invention is introduced in a space in which a medium for transmitting a sound wave exists. The capsule propulsion device includes at least one acoustic streaming generator that generates acoustic streaming as a flow of the medium in the space; a control unit that drives and controls the acoustic streaming generator; and a distance obtaining unit that obtains an object distant between the acoustic streaming generator and an object existing in the space. The control unit drives and controls the acoustic streaming generator on the basis of the distance information obtained by the distance obtaining unit.

A capsule propulsion device according to another aspect of the present invention is introduced in a space in which a medium for transmitting a sound wave exists. The capsule propulsion device includes at least one acoustic streaming generating means for generating acoustic streaming as a flow of the medium in the space; a control means for driving and controlling the acoustic streaming generating means; and a distance obtaining means for obtaining an object distant between the acoustic streaming generating means and an object existing in the space. The control means drives and controls the acoustic streaming generating means on the basis of the distance information obtained by the distance obtaining means.

A propulsion method according to still another aspect of the present invention is for propelling a capsule propulsion device in a medium that transmits a sound wave. The propulsion method includes an operation instructing step of instructing a travel direction of the capsule propulsion device; a distance measuring step of measuring distance from the capsule propulsion device to an object existing in the medium; and an acoustic streaming generating step of generating acoustic streaming for propelling the capsule propulsion device on the basis of the distance to the object measured in the distance measuring step.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2 is an external view showing a schematic configuration of a capsule medical device according to the first embodiment of the invention;

FIG. 3 is a block diagram showing a schematic configuration of a medical system made by the capsule medical device according to the first embodiment of the invention and an operation terminal connected to the capsule medical device via radio waves;

FIG. 4C is a cross-section diagram showing a schematic arrangement configuration in a section taken along line C-C' in FIG. 2;

FIG. 21 is a block diagram showing a schematic configuration of a medical system made by the capsule medical device according to the fifth modification of the first embodiment of the invention and an operation terminal connected to the capsule medical device via radio waves;

DETAILED DESCRIPTION OF THE PREFERRED EMBODIMENTS

Figure 1:
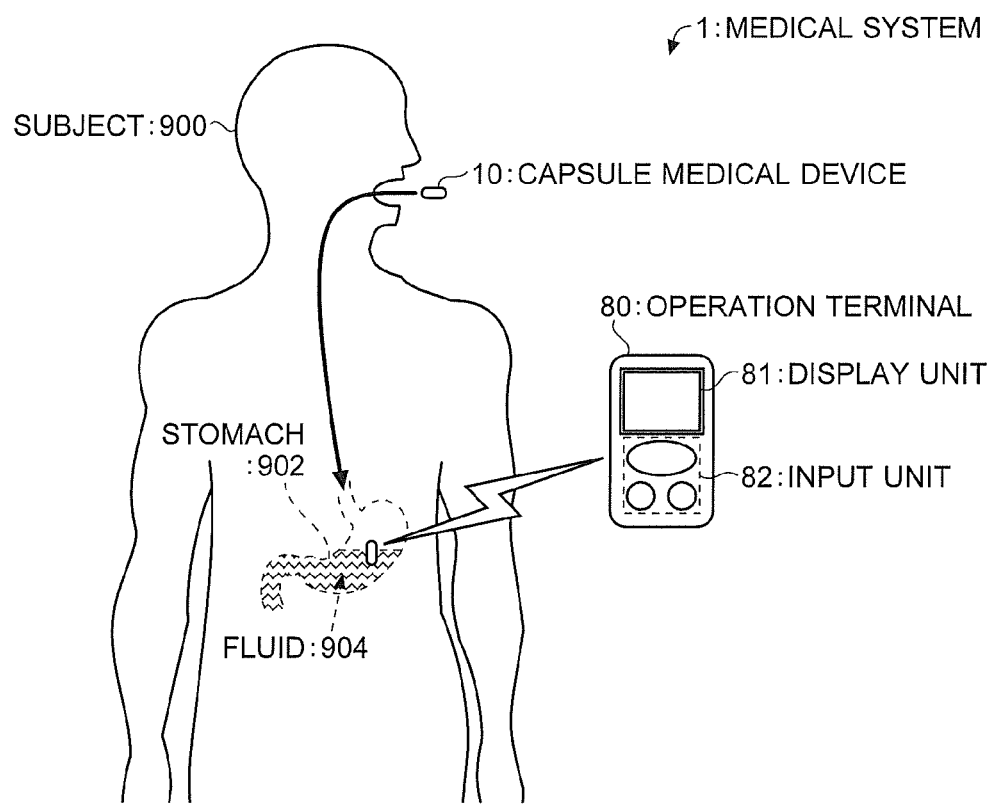
FIG. 1 is a schematic diagram showing a schematic configuration of a medical system according to a first embodiment of the invention.

Modes for carrying out the present invention will be described in detail below with reference to the drawings. The present invention is not limited to the following embodiments. In the following description, the drawings just schematically show shapes, sizes, and positional relations to a degree that the content of the present invention can be understood. Therefore, the present invention is not limited to the shapes, sizes, and positional relations shown in the drawings. In the drawings, to clearly show the configuration, a part of hatching in cross sections is omitted. Further, numerical values exemplified in the following description are just preferable examples of the invention. Therefore, the invention is not limited to the numerical values exemplified.

First Embodiment

First, the configuration and operation of a medical system 1 according to a first embodiment of the invention will be described in detail with reference to the drawings. In the embodiment, the case of using a capsule medical device 10 floating in a fluid 904 accumulated in a stomach 902 of a subject 900 as a capsule propulsion device and acquiring an image of the inner wall of the stomach 902 by using the capsule medical device 10 will be described as an example. The invention, however, is not limited to the case but can be also applied to a capsule propulsion device or a capsule medical device for obtaining some information in the subject 900 during travel from the esophagus to the anus. In-vivo information acquired by the capsule medical device 10 is not limited to a captured image but may be various information such as pH values in the body, cell tissues, blood, body fluids, and the like. An organ in which the fluid 904 is accumulated is not limited to the stomach 902 but may be any organ such as a small intestine or a large intestine. It is preferable to use, as the fluid 904, a fluid which does not exert an adverse influence on the subject 900 and the capsule medical device 10 such as saline or water. The fluid 904 is preferably transparent. It can avoid a situation that, in the case of acquiring an in-vivo image as the in-vivo information, a captured image becomes unclear due to the fluid 904.

Configuration

FIG. 1 is a schematic diagram showing a schematic configuration of the medical system 1 according to the first embodiment. As shown in FIG. 1, the medical system 1 has the capsule medical device 10 introduced into the subject 900, for example, via the oral route and floating in the fluid 904 accumulated in the stomach 902, and an operation terminal 80 used by the user to wirelessly operate the capsule medical device 10 from the outside. The operation terminal 80 has a display unit 81 for displaying an image obtained by the capsule medical device 10, and an input unit 82 including one or more operation buttons for entering various operations such as moving of the capsule medical device 10 to a desired direction, switching of an image to be displayed on the display unit, and turn-on/off of the power.

Capsule Medical Device

A schematic configuration of the capsule medical device 10 according to the embodiment will be described in detail with reference to the drawings. FIG. 2 is an external view showing a schematic configuration of the capsule medical device 10. FIG. 3 is a block diagram showing a schematic configuration of the medical system 1 made by the capsule medical device 10 and the operation terminal 80 connected to the capsule medical device 10 via radio waves.

Caps 19-1 and 19-2 are formed of a transparent material. The optical axes of a light receiving unit 105*a* and a light emitting unit 105*b* pass through the transparent cap 19-1 or 19-2 and are oriented to the outside of the capsule medical device 10 (for example, stomach wall). For example, in the embodiment, it is assumed that the optical axes of the light receiving unit 105*a* and the light emitting unit 105*b* of an imaging unit (in-vivo information acquiring unit) 105-1 disposed on the upper side are directed upward (z axis direction), and those of the light receiving unit 105*a* and the light emitting unit 105*b* of an imaging unit (in-vivo information acquiring unit) 105-2 disposed on the lower side are directed downward (−z axis direction). The invention, however, is not limited to the configuration and can be variously modified so that, for example, the optical axes are tilted in the y axis direction or oriented in the y axis direction. Further, each of the caps 19-1 and 19-2 also functions as a lens for adjusting distribution of light incident on the light receiving unit 105*a* and/or light emitted from the light emitting unit 105*b*. Each of the imaging units 105-1 and 105-2 (refer to FIG. 3) acquires an in-vivo image as image data by receiving light used to illuminate the inside of the stomach 902 by driving the light emitting unit 105*b* in FIG. 2. As the light receiving unit 105*a*, for example, a Charge Coupled Device (CCD) camera or the like can be used. As the light emitting unit 105*b*, for example, a Light Emitting Diode (LED) or the like can be used.

As shown in FIG. 2, at least one of acoustic streaming generators 106-1 to 106-6 are provided around a body portion 18. With reference to FIGS. 4A to 4C, FIGS. 5A and 5B, and FIG. 6, a layout example of the acoustic streaming generators 106-1 to 106-6 and distance measuring units 107-1 to 107-6 according to the embodiment and an operation example of the acoustic streaming generators 106-1 to 106-6 and the distance measuring units 107-1 to 107-6 will be described.

Figure 4A:
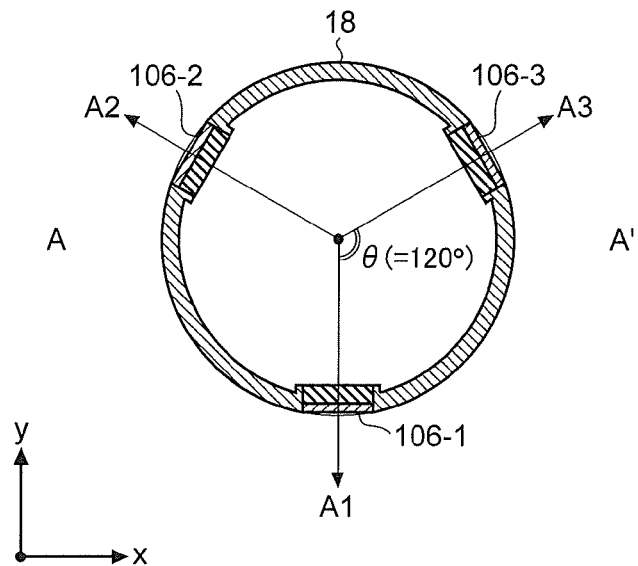
FIG. 4A is a cross-section diagram showing a schematic arrangement configuration in a section taken along line A-A' in FIG. 2.
Figure 4B:
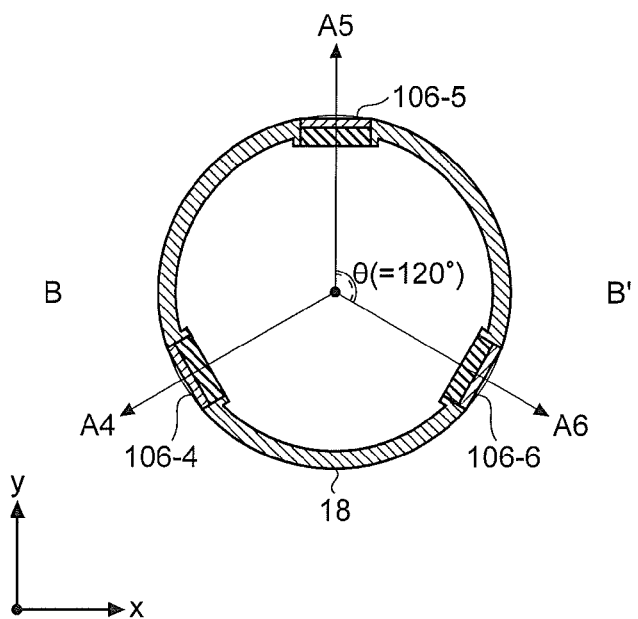
FIG. 4B is a cross-section diagram showing a schematic arrangement configuration in a section taken along line B-B' in FIG. 2.
Figure 5A:
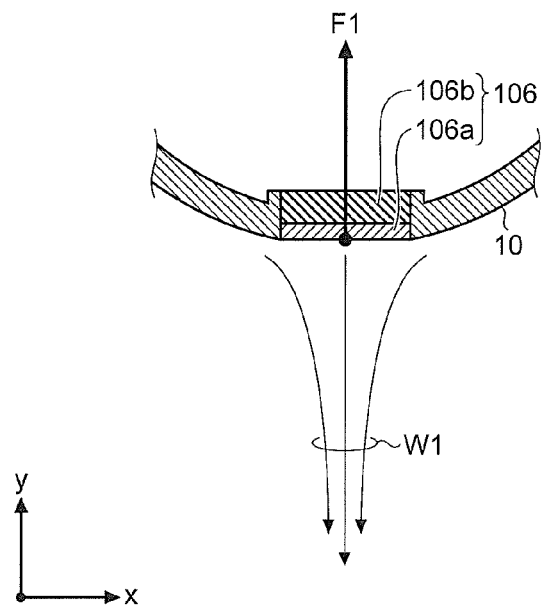
FIG. 5A is a diagram showing operation of an acoustic streaming generator when the capsule medical device according to the first embodiment of the invention moves by using one acoustic stream generator.
Figure 5B:
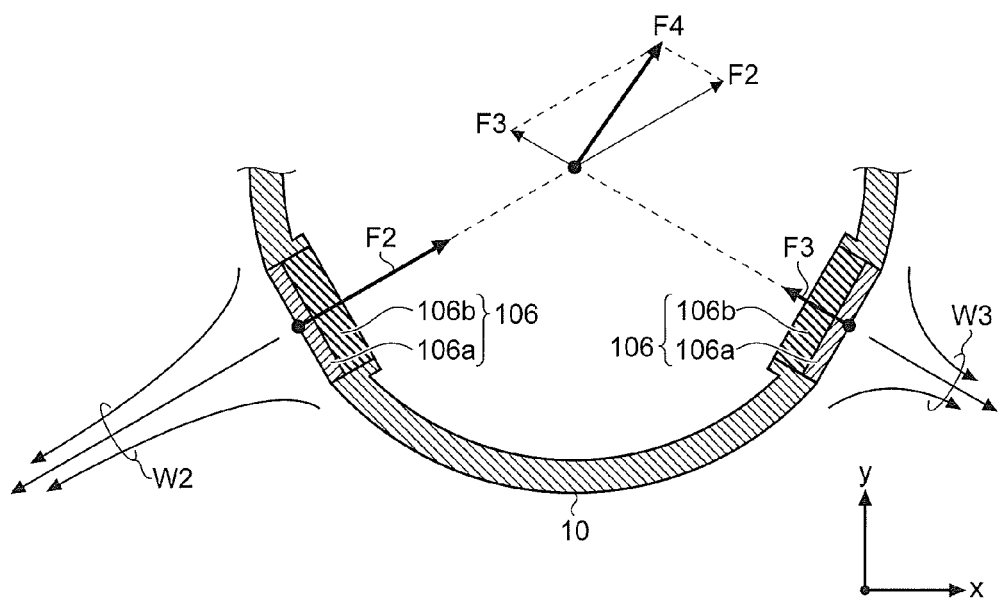
FIG. 5B is a diagram showing operations of acoustic stream generators when the capsule medical device according to the first embodiment of the invention moves by using a plurality of (for example, two)
Figure 6:
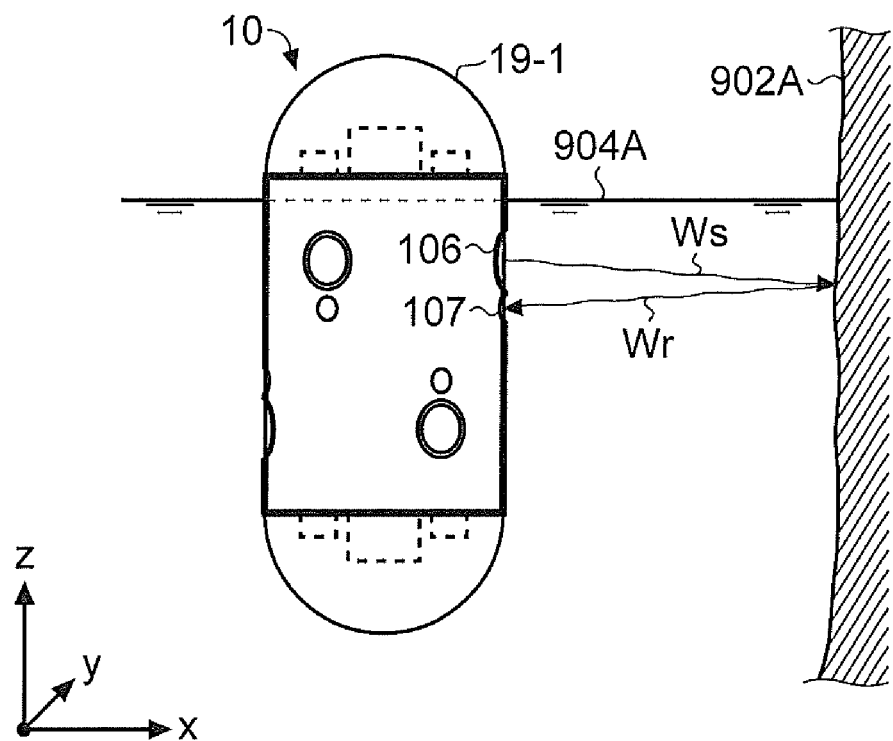
FIG. 6 is a diagram for explaining outline of detection of sound waves generated by the acoustic streaming generator by a distance measuring unit according to the first embodiment of the invention.

FIG. 4A is a cross-section diagram showing a schematic arrangement configuration in a section taken along line A-A' in FIG. 2. FIG. 4B is a cross-section diagram showing a schematic arrangement configuration in a section taken along line B-B' in FIG. 2. FIG. 4C is a cross-section diagram showing a schematic arrangement configuration in a section taken along line C-C' in FIG. 2. FIG. 5A is a diagram showing operations when the capsule medical device 10 moves by using one acoustic streaming generator. FIG. 5B is a diagram showing operations when the capsule medical device 10 moves by using a plurality of (for example, two) acoustic streaming generators. Further, FIG. 6 is a diagram for explaining outline of detection of sound waves or ultrasonic waves (hereinbelow, called sound waves) generated by the acoustic streaming generator, by the distance measuring unit. In the following description, the reference numeral of arbitrary one of the acoustic streaming generators 106-1 to 106-6 will be 106, and that of arbitrary one of the distance measuring units 107-1 to 107-6 will be 107.

As shown in FIGS. 4A and 4B, the acoustic streaming generators 106-1 to 106-6 are disposed on the side face of the body portion 18 so that travel directions of acoustic streaming (called acoustic stream axes A1 to A6) generated by them become different from one another. In the embodiment, the six acoustic streaming generators 106-1 to 106-6 are used as an example. Three acoustic streaming generators (106-1 to 106-3) are disposed on the cap 19-1 side (the upper stage), and the remaining three acoustic streaming generators (106-4 to 106-6) are disposed on the other cap 19-2 side (the lower stage). The three acoustic streaming generators 106-1 to 106-3 disposed in the upper stage are disposed so that the angle formed by neighboring ones of their acoustic stream axes A1 to A3 becomes 120°, and the three acoustic streaming generators 106-4 to 106-6 disposed in the lower stage are disposed so that the angle formed by neighboring ones of their acoustic stream axes A4 to A6 becomes 120°. With the arrangement, the propulsion force can be generated in any direction in the x-y plane using one or more of the acoustic streaming generators 106-1 to 106-3 in the upper stage. Similarly, the propulsion force can be generated in any direction in the x-y plane using one or more of the acoustic streaming generators 106-4 to 106-6 in the lower stage. Further, the directions of the three acoustic streaming generators 106-1 to 106-3 disposed in the upper stage are deviated from those of the three acoustic streaming generators 106-4 to 106-6 disposed in the lower stage by 60°. With the configuration, for example, even in the case of inhibiting driving of the acoustic streaming generators 106-1 to 106-3 in the upper stage, the capsule medical device 10 can be moved by driving the acoustic streaming generators 106-4 to 106-6 in the lower stage. However, the present invention is not limited to the above-described numbers and directions but can be variously modified as long as the propulsion force can be generated in any direction in the x-y plane.

As shown by the acoustic streaming generator 106 in FIG. 5A, each of the acoustic streaming generators 106-1 to 106-6 has, for example, a piezoelectric element 106*a* having a flat plate shape and a damping unit (vibration absorbing unit) 106*b* that prevents vibration generated by the piezoelectric element 106a from propagating to the capsule medical device 10 side. An AC voltage having a predetermined resonance frequency is applied to the piezoelectric element 106a so that vibration whose amplitude is in the direction perpendicular to (normal direction) the side face of the body portion 18 occurs. Consequently, as shown in FIG. 5A, acoustic streaming W1 generated by the acoustic streaming generator 106 travels in the direction normal to the side face of the body portion 18. In other words, the acoustic streaming axes A1 to A6 of the acoustic streaming generated by the acoustic streaming generators 106-1 to 106-6 are in the direction normal to the side face of the capsule medical device 10. Therefore, the propulsion force F1 obtained by the acoustic streaming W1 is in the direction (−A1 direction) opposite to the travel direction of the acoustic streaming W1. The frequency of the AC voltage applied to the piezoelectric element 106a has to be a resonance frequency at which the piezoelectric element 106a can generate acoustic streaming. The resonance frequency is usually a few MHz.

As shown in FIG. 5B, by simultaneously driving a plurality of (for example, two) acoustic streaming generators 106, propulsion forces generated by the acoustic streaming generators 106 (for example, a propulsion force F2 obtained by the acoustic streaming W2 and a propulsion force F3 obtained by the acoustic streaming W3) can be combined. By adjusting the frequency and amplitude of the AC voltage applied to the piezoelectric element 106a of each of the acoustic streaming generators 106, each of the propulsion forces can be adjusted. Therefore, the direction and magnitude of a force (a combined propulsion force F4) obtained by combining the plurality of propulsion forces (for example, the propulsion forces F2 and F3) can be controlled.

As described above, the capsule medical device 10 according to the embodiment can obtain the propulsion force (combined propulsion force) in any direction in the xy plane by driving one of the acoustic streaming generators 106-1 to 106-3 in the upper stage, so that it can move in any direction in the xy plane. Similarly, the capsule medical device 10 can obtain the propulsion force (combined propulsion force) in any direction in the xy plane by driving one of the acoustic streaming generators 106-4 to 106-6 in the lower stage, so that it can move in any direction in the xy plane.

As shown in FIGS. 2 and 4C, the plurality of distance measuring units 107-1 to 107-6 for measuring the distances from the acoustic streaming generators 106-1 to 106-6 to an object existing in the travel directions of the acoustic streaming generated by the acoustic streaming generators 106-1 to 106-6 are provided around the body portion 18. In the embodiment, one distance measuring unit 107 is provided for one acoustic streaming generator 106. The present invention is not limited to the configuration but can be variously modified to a configuration such that one distance measuring unit 107 is provided for the plurality of acoustic streaming generators 106.

The distance measuring unit 107 is constructed by, for example, a microphone and is disposed close to the corresponding acoustic streaming generator 106. The distance measuring unit 107 detects, as shown in FIG. 6, a wave (reflection wave Wr) returned by being reflected by an object (for example, a stomach wall 902A), in the sound waves Ws output from the acoustic streaming generator 106. Preferably, the sound wave Ws output from the acoustic streaming generator 106 for distance measurement is weaker than a sound wave output from the acoustic streaming generator 106 in order to generate a propulsion force. Such a sound wave Ws can be generated by applying an AC voltage having a frequency sufficiently lower than the frequency (resonance frequency) used in the case of generating the acoustic streaming generator to the piezoelectric element 106a.

The distance to an object can be obtained by using any of various methods such as a method of measuring time since the acoustic streaming generator 106 outputs the sound wave Ws until the distance measuring unit 107 detects a refection component (reflection wave Wr) of the sound wave Ws and multiplying the measured time with propagation velocity of the sound wave Ws, and a method of calculating the distance by comparing the phase of the output sound wave Ws (or the phase of AC voltage to be applied to the acoustic streaming generator 106) with the phase of the reflection wave Wr detected by the distance measuring unit 107. For example, a detection value of the distance measuring unit 107 is supplied to a control unit 101, and the above-described computation is executed in the control unit 101.

In addition, the center of gravity of the capsule medical device 10 according to the embodiment is deviated in a predetermined direction from the center of the capsule medical device 10 to control the posture of the capsule medical device 10 which is floating or sinking in the fluid 904 accumulated in the stomach 902. In the embodiment, the center of gravity of the capsule medical device 10 is deviated to the cap 19-2 side so that the imaging unit 105-1 on the cap 19-1 side obtains an image of the above or the stomach wall 902A above a fluid level 904A and the imaging unit 105-2 on the cap 19-2 side obtains an image of the lower part or the stomach wall 902A below the fluid level 904A. It can be realized by various configurations such that, for example, the weight of the cap 19-2 is set to be heavier than that of the cap 19-1, the parts provided on the inside such as the body portion 18 and the caps 19-1 and 19-2 are disposed on the side of the cap 19-2, and a weight such as a lead plate is attached on the side of the cap 19-2 so as not to disturb imaging.

For example, to enable the capsule medical device 10 move at the fluid level 904A of the fluid 904 or in the fluid 904, the specific gravity of the capsule medical device 10 is preferably smaller than or about the same as that of the fluid 904. In the embodiment, for example, as shown in FIG. 6, the specific gravity of the capsule medical device 10 is set to be light to a degree that at least a part of the cap 19-1 positioned in an upper part projects from the fluid level 904A and to be heavy to a degree that at least a part of the acoustic steaming generator 106 disposed in an upper stage is positioned below the fluid level 904A.

As shown in FIG. 3, provided in a casing (18, 19-1, and 19-2) of the capsule medical device 10 are, for example, the control unit 101 for executing control on the components mounted on the capsule medical device 10 and various processes, a signal processing unit 102 for processing data to be output to the operation terminal 80 and data input from the operation terminal 80, a signal transmitting/receiving unit 103 for controlling transmission/reception of a signal to/from the operation terminal 80, the two imaging units 105-1 and 105-2 for acquiring an in-vivo image as image data, a storing unit 104 for storing various data such as the image data of an in-vivo image acquired by the imaging units 105-1 and 105-2 and control instructions received via the signal transmitting/receiving unit 103, and various programs executed by the control unit 101 to control the components in the capsule medical device 10, the plurality of acoustic streaming generators 106-1 to 106-6 for generating the propulsion force of the capsule medical device 10, and the distance measuring units 107-1 to 107-6 for measuring the distance between the acoustic streaming generators 106-1 to 106-6 and the object.

The control unit 101 makes the components execute various operations such as imaging operation and transmitting/ receiving operation by, for example, controlling/driving the components in the capsule medical device 10 on the basis of various control programs read from the storing unit 104, an operation instruction received from the operation terminal 80 via the signal transmitting/receiving unit 103, and the like. The control unit 101 can be constructed by, for example, information processing units such as a Central Processing Unit (CPU) and a Microprocessor (MPU).

The storing unit 104 stores the various control programs properly executed by the control unit 101, image data obtained by the imaging units 105-1 and 105-2, and various data and other setting information received via the signal transmitting/receiving unit 103. The storing unit 104 can be constructed by using, for example, a Random Access Memory (RAM). The storing unit 104 may include a Read Only Memory (ROM) for storing the above-described various control programs.

Each of the imaging units 105-1 and 105-2 has, for example, a configuration in which the light receiving unit 105a (refer to FIG. 2) for obtaining an image of the inside of the subject 900 as image data and one or more light emitting units 105b for illuminating the inside of the subject 900 with light at the time of imaging are mounted on a circuit board having predetermined drive/control circuits, lines, and the like. When the imaging units 105-1 and 105-2 operate under control of the control unit 101, an in-vivo image (an image of the inner wall of the stomach 902) is properly acquired as image data. The acquired image data is, for example, recorded on the storing unit 104 via the control unit 101 or subjected to a predetermined process in the signal processing unit 102 and, after that, sent to the operation terminal 80 by the signal transmitting/receiving unit 103. An objective lens and the like may be also disposed on the light receiving plane side of the light receiving unit 105a.

The signal processing unit 102 executes predetermined processes such as coding of transmission data and decoding of reception data. The signal transmitting/receiving unit 103 executes superimposition of a transmission signal input from the signal processing unit 102 to a reference frequency signal for transmission, modulation, up-conversion, and the like, or filtering, down-conversion, demodulation, and the like on the received frequency signal. The signal processing unit 102 and the signal transmitting/receiving unit 103 function as an input receiving unit of receiving an input such as a travel instruction, power-on/off, from the operation terminal 80 as an external apparatus, and inputting the received input to the control unit 101.

Since the acoustic streaming generators 106-1 to 106-6 and the distance measuring units 107-1 to 107-6 are the same as those described above, their detailed description will not be repeated.

Operation Terminal

The operation terminal 80 shown in FIG. 1 has, as shown in FIG. 3, a signal transmitting/receiving unit 802 for establishing a wireless circuit to the signal transmitting/receiving unit 103 in the capsule medical device 10 and transmitting/receiving a signal, a signal computing unit 801 for executing a predetermined computing process on reception data which is input via the signal transmitting/receiving unit 802 and data which is input from the input unit 82, the display unit 81 for displaying the in-vivo image sent from the capsule medical device 10 to the user, the input unit 82 used by the user to enter operation, and a storing unit 803 for storing data of an in-vivo image sent from the capsule medical device 10, data corresponding to an operation signal (in the description, simply called operation instruction) generated by the input unit 82, and various programs used by the signal computing unit 801 to execute various operations.

In the configuration, reception data such as image data sent from the capsule medical device 10 is subjected to a predetermined process in the signal transmitting/receiving unit 802, and is input to the signal computing unit 801. The signal computing unit 801 executes a process such as decompression/compression on the image data and enters the resultant data and displays it in the display unit 81.

When any of the operation buttons in the input unit 82 is depressed by the user, the input unit 82 generates a signal corresponding to the depressed operation button (called an operation signal) and supplies it to the signal computing unit 801. The signal computing unit 801 reads an operation instruction corresponding to the input operation signal from the storing unit 803 and transmits it to the capsule medical device 10 via the signal transmitting/receiving unit 802.

In the embodiment as described above, the medical system 1 by which the user can diagnose the subject 900 while seeing an image of the inside of the subject 900 using the capsule medical device 10 which can be operated by the operation terminal 80 is realized.

Operation

Figure 7:
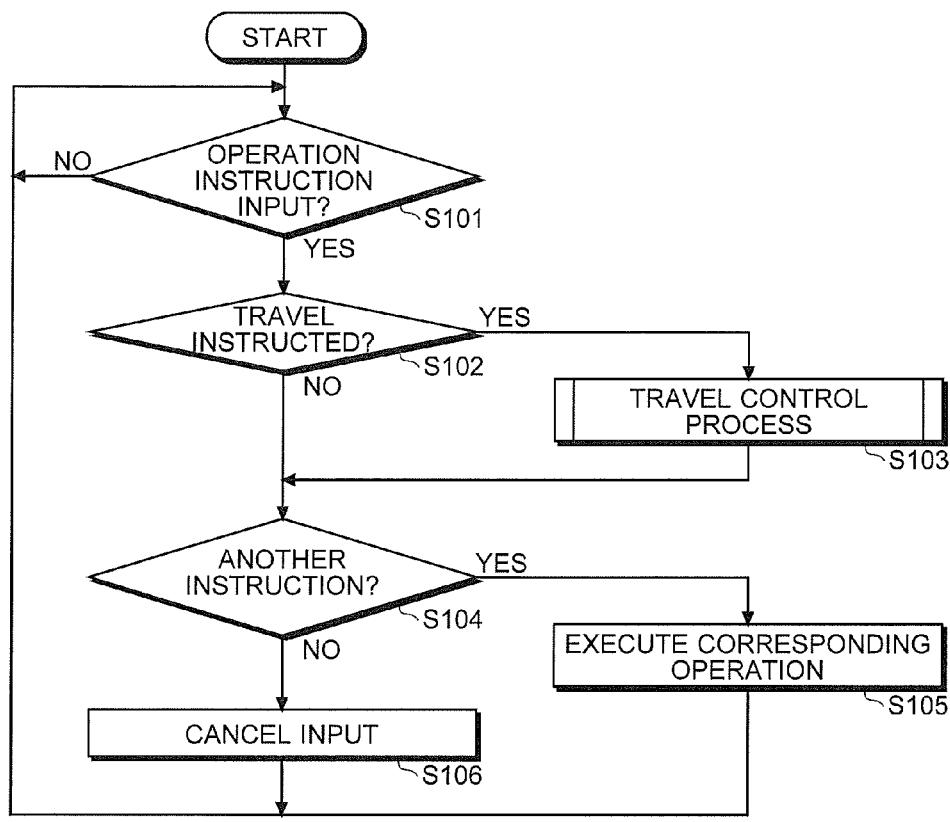
FIG. 7 is a flowchart showing an example of general operations performed at the time of operating the capsule medical device by using an operation terminal according to the first embodiment of the invention.
Figure 8:
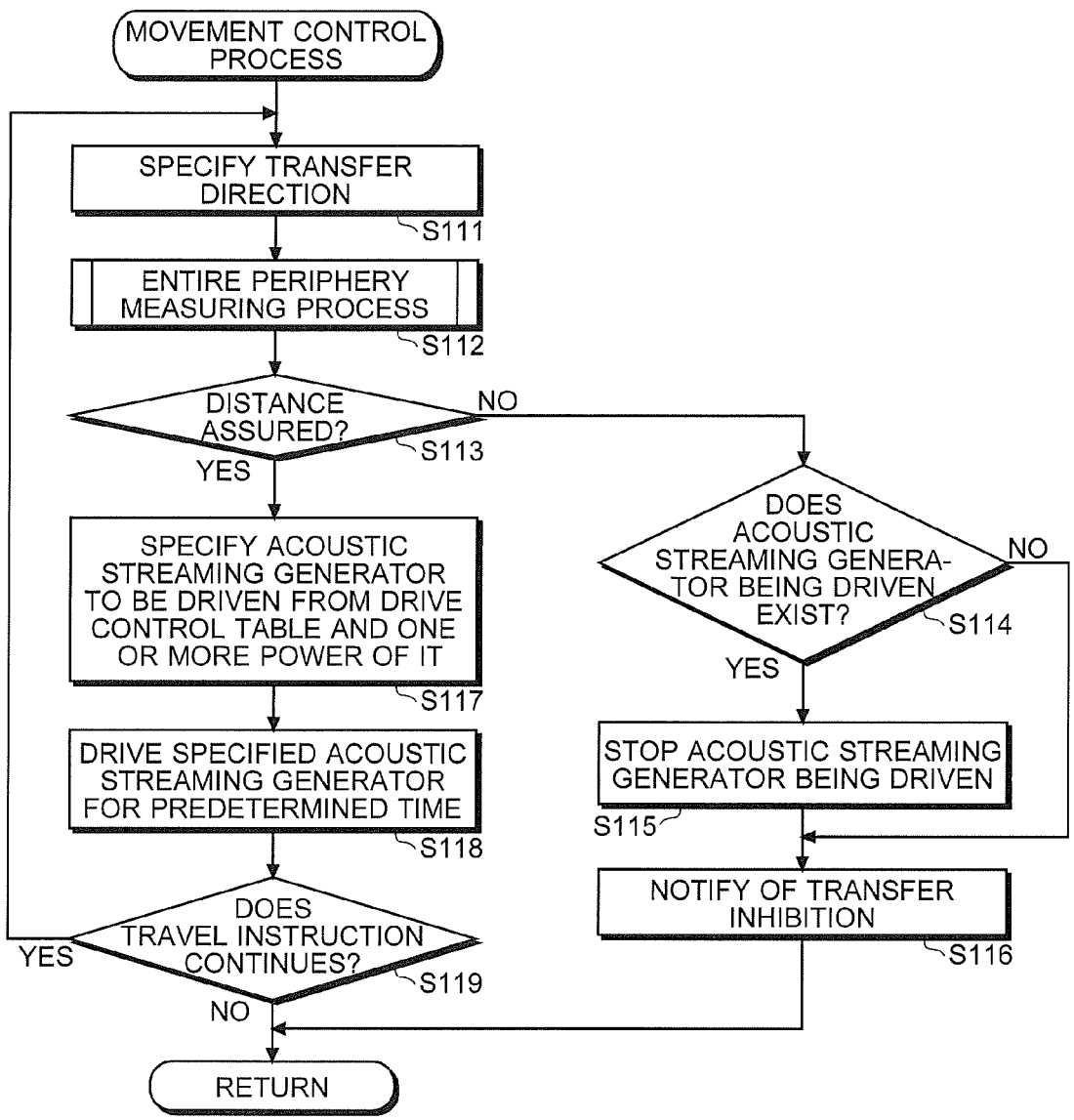
FIG. 8 is a flowchart showing an example of operation in a travel control process according to the first embodiment of the invention.
Figure 9:
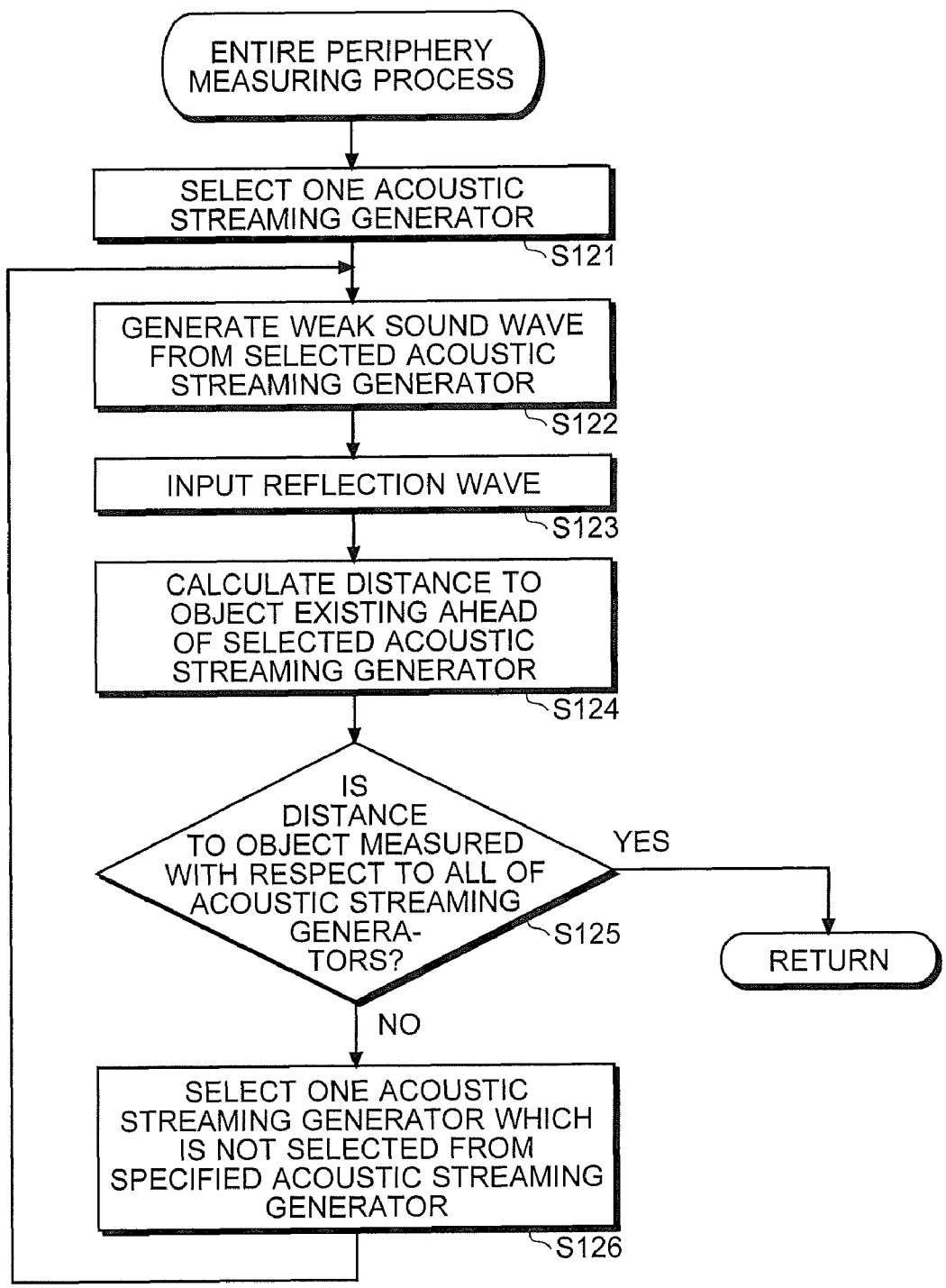
FIG. 9 is a flowchart showing an example of operation in an entire periphery measuring process according to the first embodiment of the invention.

Next, the operation performed at the time of operating the capsule medical device 10 by using the operation terminal 80 in the embodiment will be described in detail with reference to the drawings. FIGS. 7 to 9 are flowcharts showing the operations of the capsule medical device 10 operated by the operation terminal 80 according to the embodiment. FIGS. 10 to 12B are diagrams for supplementing description of the operation of the capsule medical device 10 according to the embodiment. In the following description, attention is paid to the operation of the control unit 101 for controlling the general operation of the capsule medical device 10.

General Operation

Figures 10, 11:
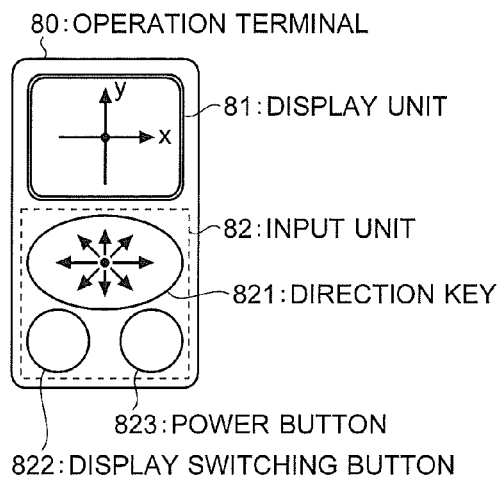
FIG. 10 is an external view showing a schematic configuration of the operation terminal according to the embodiment of the invention.
FIG. 11 is a diagram showing an example of a drive control table according to the first embodiment of the invention.
Figure 12A:
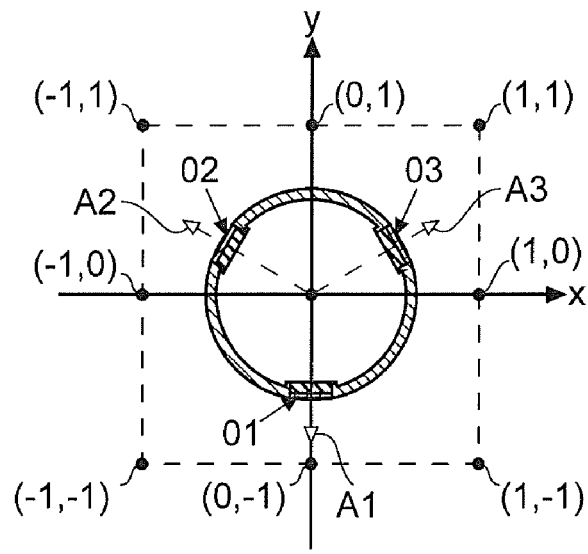
FIG. 12A is a diagram showing the relation between three acoustic streaming generators disposed in an upper stage in the capsule medical device according to the first embodiment of the invention and coordinates (display orientation) of a display unit of the operation terminal.
Figure 12B:
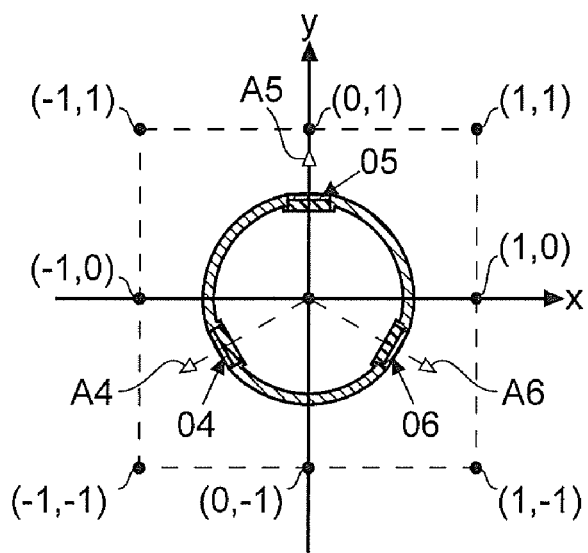
FIG. 12B is a diagram showing the relation between three acoustic streaming generators disposed in a lower stage in the capsule medical device according to the first embodiment of the invention and coordinates (display orientation) of a display unit of the operation terminal.

FIG. 7 is a flowchart showing an example of general operations performed at the time of operating the capsule medical device 10 by using the operation terminal 80 according to the embodiment. FIG. 8 is a flowchart showing an example of operation in a travel control process (step S103 in FIG. 7) according to the embodiment. FIG. 9 is a flowchart showing an example of operation in an entire periphery measuring process (for example, step S112 in FIG. 8) according to the embodiment. FIG. 10 is an external view showing a schematic configuration of the operation terminal 80 according to the embodiment. FIG. 11 is a diagram showing an example of a drive control table in which an operation instruction (travel direction) entered from the operation terminal 80, the acoustic streaming generator 106 (ID) driven in response to the operation instruction, and information of power (power information) for the driving are associated. FIG. 12A is a diagram showing the relation between the three acoustic streaming generators 106-1 to 106-3 disposed in an upper stage in the capsule medical device 10 and coordinates (display orientation) of the display unit 81 of the operation terminal 80. FIG. 12B is a diagram showing the relation between the three acoustic streaming generators 106-4 to 106-6 disposed in a lower stage in the capsule medical device 10 and coordinates (display orientation) of the display unit 81 of the operation terminal 80.

As described above, the operation by the user of the capsule medical device 10 is performed by using the operation terminal 80. The operation terminal 80 according to the embodiment will be described more specifically. As shown in FIG. 10, the operation terminal 80 includes the display unit 81 for displaying an in-vivo image captured by the capsule medical device 10 to the user, and the input unit 82 used by the user to enter various operation instructions for operating the capsule medical device 10. The input unit 82 includes a direction key 821 for entering the travel direction of the capsule medical device 10, a display switching button 822 for switching an image displayed on the display unit 81 among an image obtained by the imaging unit 105-1 on the upper side in the capsule medical device 10, an image obtained by the imaging unit 105-2 on the lower side, and an image obtained by combining the images obtained by the imaging units 105-1 and 105-2 (2 split screen), and a power button 823 for turning on/off the power of the capsule medical device 10. With the direction key 821 according to the embodiment, travel instructions in eight directions in an xy plane using, as a start point, the capsule medical device 10 (for example, the axis passing through the center of the display unit 81) can be entered. The invention is not limited to the configuration but can be variously modified. For example, travel instructions in four directions, 16 directions, 360° directions, and the like can be entered. For example, when the optical axis of the imaging unit 105-1 and/or the imaging unit 105-2 tilts with respect to the z axis direction, a horizontal component of the tilt can be used as a reference (for example, the y axis direction).

When the power of the capsule medical device 10 is turned on by a starter of a contact type or a noncontact type or the power button 823, the capsule medical device 10 starts the generation operation shown in FIG. 7. In the general operation shown in FIG. 7, the control unit 101 first determines whether an operation instruction is received from the operation terminal 80 (step S101). Until some operation instruction is received from the operation terminal 80, the control unit 101 holds an operation except for an imaging process (No at step S101). The control unit 101 periodically drives the imaging unit 105-1 and/or the imaging unit 105-2 selected by using the display switching button 82 in the operation terminal 80 (hereinbelow, the reference numeral for an arbitrary imaging unit will be written as 105) to obtain an in-vivo image and transmits the in-vivo image to the operation terminal 80. The operation terminal 80 displays the image periodically received from the capsule medical device 10 on the display unit 81. Since the image of the inside of the subject is displayed in a real-time manner to the operator, the operator can operate the capsule medical device 10 in accordance with the situation.

On the other hand, when an operation instruction is entered by the operation terminal 80 (Yes at step S101), the control unit 101 determines whether the entered operation instruction is an instruction to move the capsule medical device 10 entered by using the direction key 821 (refer to FIG. 10) (step S102). When it is a travel instruction (Yes at step S102), the control unit 101 executes a travel control process (step S103). The details of the travel control process will be described later with reference to FIG. 8.

On the other hand, when the operation instruction entered by the operation terminal 80 is not a travel instruction (No at step S102), the control unit 101 determines whether the operation instruction is another predetermined instruction (step S104). If the operation instruction is another predetermined instruction (Yes at step S104), the control unit 101 executes a corresponding operation (step S105). If the operation instruction is an instruction which does not belong to any of the above-described instructions (No at step S104), the control unit 101 cancels the entered instruction (step S106) and returns to step S101. For example, the operation of the capsule medical device 10 is finished by an interrupt control in response to a power-off instruction entered from the power button 823 in the input unit 82 of the operation terminal 80 or finished when a not-shown battery in the capsule medical device 10 runs out.

Travel Control Process

Next, the travel control process shown in step S103 in FIG. 7 will be described in detail with reference to the drawings. FIG. 8 is a flowchart showing the flow of the travel control process according to the embodiment.

As shown in FIG. 8, in the travel control process (step S103 in FIG. 7), first, the control unit 101 specifies the travel direction of the capsule medical device 10 instructed by the travel instruction (step S111). Next, the control unit 101 executes the entire periphery measuring process of obtaining the distance to an object in the entire periphery of the capsule medical device 10 (periphery distance) by sequentially driving, for example, all of the acoustic streaming generators 106 and all of the distance measuring units 107 (step S112). The details of the entire periphery measuring process will be described later with reference to FIG. 9.

Next, the control unit 101 determines whether a distance equal to or longer than a predetermined threshold (distance D1) to an object (stomach wall 902A) in the travel direction specified in step s111 is assured on the basis of the periphery distance obtained in step S112 (step S113). When a distance corresponding to the predetermined threshold (distance D1) is assured (Yes at step S113), the control unit 101 moves to step S117. On the other hand, when the distance is not assured (No at step S113), the control unit 101 determines whether the acoustic streaming generator 106 which is being driven exists (step S114). When it exists (Yes at step S114), the control unit 101 stops the acoustic streaming generator 106 (step S115). After that, the control unit 101 notifies the operation terminal 80 of the state that travel in the direction entered by the operation terminal 80 is not allowed (step S116) and returns to the general operation in FIG. 7. On the other hand, when the acoustic streaming generator 106 which is being driven does not exist (No at step S114), the control unit 101 moves to step S116, notifies the operation terminal 80 of the state that travel is not allowed and, after that, returns to the general operation in FIG. 7. The operation terminal 80 which is notified of the state that travel in the instructed direction is not allowed displays the state on the display unit 81 or notifies the operator of the state by sound or voice from a not-shown speaker.

When the predetermined threshold (distance D1) is not assured as a result of determination in step S113 (No at step S113), the control unit 101 determines whether the capsule medical device 10 is traveling. If the capsule medical device 10 is traveling, the control unit 101 may drive the acoustic streaming generator 106 to temporarily generate a propulsion in a direction opposite to the travel direction of the capsule medical device 10, thereby stopping the capsule medical device 10. Whether the capsule medical device 10 is presently traveling can be known by using various methods such as a method of determining it by using a not-shown acceleration sensor, a method of determining it from an image captured periodically by the imaging unit 105, and a method of determining it from a periphery distance obtained by periodically executing the entire periphery measuring process.

In step S117, the control unit 101 specifies the acoustic streaming generator 106 (its ID) which enables travel in the direction specified as the travel direction in step S111 and one or more powers (power information) to be given at the time of driving the acoustic streaming generators 106 from a drive control table (refer to FIG. 11) which will be described later. The invention is not limited to the configuration but may employ a configuration of specifying the acoustic streaming generator 106 to be driven in accordance with the instructed direction and computing the power at the time of driving the acoustic streaming generator 106 each time. It is sufficient to select the acoustic streaming generator 106 specified in step S117 in consideration of balance on the capsule medical device 10, of the propulsion force generated from the acoustic streaming generators 106 on the upper and lower stages.

Next, the control unit 101 drives the acoustic streaming generator 106 specified in step S117 in accordance with the power information similarly specified for predetermined time (step S118). By the driving, the propulsion force in the travel direction is given to the capsule medical device 10.

As described above, when one or more acoustic streaming generators 106 are driven to give the propulsion force in the travel direction to the capsule medical device 10, the control unit 101 determines whether the travel instruction is continuously received from the operation terminal 80 (step S119). When the travel instruction is continuously received (Yes at step S119), the control unit 101 returns to step S111 and repeats the following operation. On the other hand, when the travel instruction is not continuously received (No at step S119), the control unit 101 returns to the general operation in FIG. 7.

The capsule medical device 10 as the capsule propulsion device according to the embodiment, which is introduced in a space (the stomach 902) in which a medium for transmitting a sound wave exists, includes: a plurality of acoustic streaming generators 106-1 to 106-6 for generating acoustic streaming as a flow of the a medium in the stomach 902; the distance obtaining unit (the distance measuring units 107-1 to 107-6 and the control unit 101) for obtaining an object distance between the acoustic streaming generators 106-1 to 106-6 and the object (stomach wall 902A) existing in the direction of the flow of the acoustic streaming generated by the acoustic streaming generators 106-1 to 106-6; and the control unit 101 for performing driving and control to make the acoustic streaming generator 106 having an object distance equal to or longer than a predetermined threshold (distance D1) generate acoustic streaming. With the configuration, the capsule medical device 10 capable of traveling in a desired direction regardless of the position and orientation in the subject 900 and the medical system 1 having the same can be realized.

Entire Periphery Measuring Process

The entire periphery measuring process shown in step S112 in FIG. 8 will be described in detail with reference to the drawings. FIG. 9 is a flowchart showing the flow of the entire periphery measuring process according to the embodiment.

As shown in FIG. 9, in the entire periphery measuring process (step S112 in FIG. 8), first, the control unit 101 selects any of the acoustic streaming generators 106-1 to 106-6 (step S121) and makes the selected acoustic streaming generator 106 generate a weak sound wave Ws (step S122).

The control unit 101 receives a reflection wave Wr of the sound wave Ws generated by the acoustic streaming generator 106 by using the distance measuring unit 107 associated with the selected acoustic streaming generator 106 (step S123) and, on the basis of the difference between the timing at which the acoustic streaming generator 106 is made output the sound wave Ws and the timing at which the distance measuring unit 107 detects the reflection wave Wr, calculates the distance from the selected acoustic streaming generator 106 to an object ahead (step S124).

Next, the control unit 101 determines whether the distance to the object is calculated with respect to all of the acoustic streaming generators 106 (step S125). In the case of "No" (No at step S125), the control unit 101 selects one of the acoustic streaming generators 106 which are not selected (step S126), after that, returns to step S122, and repeats the subsequent operations until the distance to the object is calculated with respect to all of the acoustic streaming generators 106. On the other hand, when the distance to the object is calculated with respect to all of the acoustic streaming generators 106 (Yes at step S125), the control unit 101 returns to the travel control process in FIG. 8.

As described above, by calculating the distance from each of the acoustic streaming generators 106 to an object by using the sound wave Ws emitted from the acoustic streaming generators 106 disposed along the entire periphery of the capsule medical device 10, the distances (periphery distance) to the object from the entire periphery of the capsule medical device 10 can be obtained.

Drive Control Table

A drive control table shown in FIG. 11 will be described by using a diagram showing the relation between the acoustic streaming generators 106-1 to 106-3 in an upper stage shown in FIG. 12A and a diagram showing the relation between the acoustic streaming generators 106-4 to 106-6 in a lower stage shown in FIG. 12B. The x-y coordinates shown in FIGS. 12A and 12B is coordinates using, as a reference, the center of an image captured by the imaging unit 105-1 or 105-2 and the center of a display region of the display unit 81 in the operation terminal 80. The coordinate system of the direction key 821 in the input unit 82 of the operation terminal 80 is also set on the basis of the x-y coordinates.

As shown in FIG. 12A, in the acoustic streaming generators 106-1 to 106-3 disposed in the upper stage in the capsule medical device 10, the acoustic streaming generator 106-1 to which ID "01" is given is disposed so that its acoustic streaming axis A1 is in the (0,−1) direction in the x-y plane. The acoustic streaming generator 106-2 to which ID "02" is given is disposed so that its acoustic streaming axis A2 is in the (−√3 (about 1.732),1) direction in the x-y plane. The acoustic streaming generator 106-3 to which ID "03" is given is disposed so that its acoustic streaming axis A3 is in the (√3 (about 1.732),1) direction in the x-y plane.

Similarly, in the acoustic streaming generators 106-4 to 106-6 disposed in the lower stage in the capsule medical device 10, the acoustic streaming generator 106-4 to which ID "04" is given is disposed so that its acoustic streaming axis A4 is in the (−√3 (about 1.732),−1) direction in the x-y plane. The acoustic streaming generator 106-5 to which ID "05" is given is disposed so that its acoustic streaming axis A5 is in the (0,1) direction in the x-y plane. The acoustic streaming generator 106-6 to which ID "06" is given is disposed so that its acoustic streaming axis A6 is in the (√3 (about 1.732),−1) direction in the x-y plane.

In the embodiment, the direction key 821 of the operation terminal 80 is a so-called 8-way key by which travel instructions in eight directions can be entered. Consequently, for example, when the right direction of the direction key 821 is depressed, a travel instruction in the (1,0) direction is entered from the operation terminal 80 to the capsule medical device 10. Similarly, when a right upper direction, an upper direction, a left upper direction, a left direction, a left lower direction, a lower direction, and a right lower direction are depressed, travel instructions of a (1,1) direction, a (0,1) direction, a (−1,1) direction, a (−1,0) direction, a (−1,−1) direction, a (0,−1) direction, and a (1,−1) direction are entered to the capsule medical device 10, respectively.

In the embodiment, to make the capsule medical device 10 travel at the same travel speed in response to a travel instruction in any direction, the correspondence relations between the direction of a travel instruction (travel direction), the acoustic streaming generator 106 (ID) to be driven, and power used for the driving (power information) are managed by using the drive control table shown in FIG. 11. The power is electric power expressed by the frequency and amplitude of AC voltage applied to the piezoelectric element 106a of the acoustic streaming generator 106.

In the drive control table of FIG. 11, the power applied to the acoustic streaming generator 106 at the time of moving the capsule medical device 10 by driving one acoustic streaming generator 106 is set to 100, and an acoustic streaming generator 106 (ID) to be driven and its power (power information) is managed so as to obtain the same propulsion force as that in the case of driving one acoustic streaming generator 106 by the same power "100" even when a travel instruction in any direction is received. For example, when a travel instruction in the (1,0) direction is entered, the acoustic streaming generators 106-1 to 106-3 in the upper stage are managed in the drive control table shown in FIG. 11 as follows. Two acoustic streaming generators 106 of the acoustic streaming generator 106-1 having the ID of "01" and the acoustic streaming generator 106-2 having the ID Of "02" are driven, the power given to the acoustic streaming generator 106-1 is set to "50", and the power given to the acoustic streaming generator 106-2 is set to "115.5 (about $2/\sqrt{3}$))".

By managing a travel direction, information (ID) for specifying an acoustic streaming generator 106 to be enabled to be moved in the travel direction, and information of power (power information) to be given at the time of driving the acoustic streaming generator 106 so as to be associated with one another, the acoustic streaming generator 106 to be driven at the time of travel and the power to be given to the acoustic streaming generator 106 can be easily specified with a small process amount, and swifter travel control is enabled.

Object Distance Assuring Process

Figure 13:
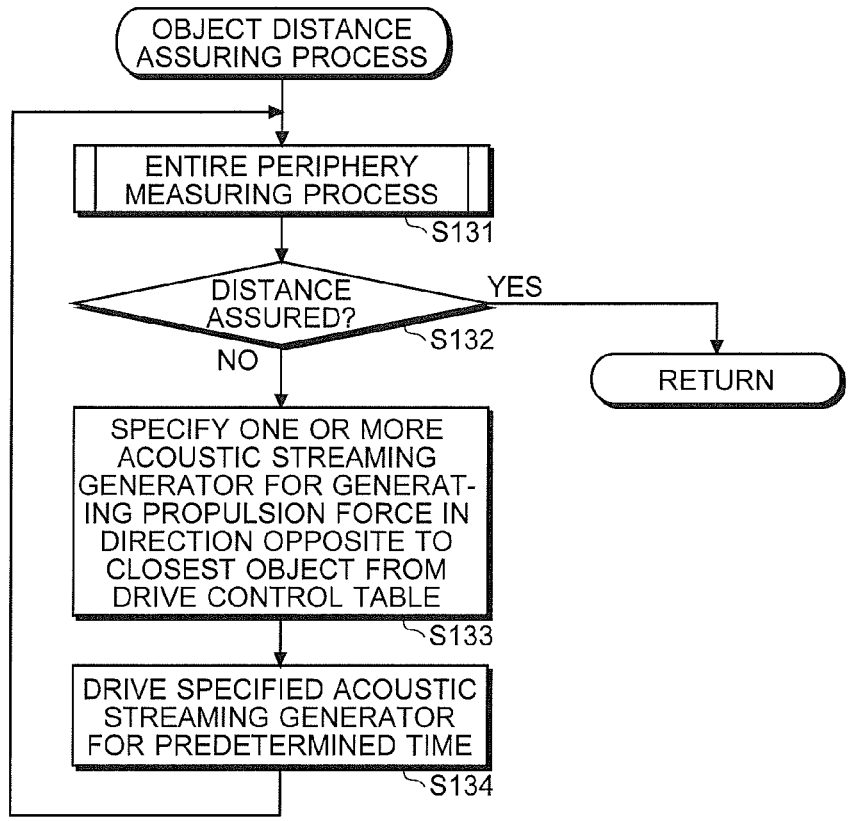
FIG. 13 is a flowchart showing an example of operations in an object distance assuring process according to the first embodiment of the invention.
Figure 14:
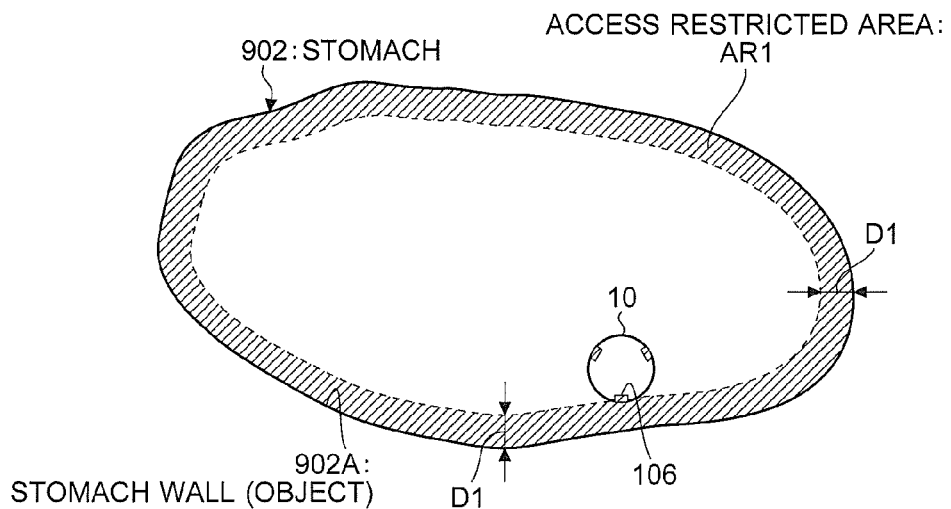
FIG. 14 is a conceptual diagram for explaining how the capsule medical device according to the first embodiment of the invention is controlled with respect to an object (stomach wall)

The capsule medical device 10 according to the embodiment may periodically execute an operation of maintaining the distance to the object (stomach wall 902A) to be a predetermined distance (predetermined threshold (distance D1)) or longer (object distance assuring process) during the flow in the general operation shown in FIG. 7. FIG. 13 is a flowchart showing the flow of the object distance assuring process according to the embodiment. FIG. 14 is a conceptual diagram for explaining how the capsule medical device 10 according to the embodiment is controlled with respect to an object (stomach wall 902A).

As shown in FIG. 13, in the object distance assuring process according to the embodiment, first, the control unit 101 sequentially drives, for example, all of the acoustic streaming generators 106-1 to 106-6 and all of the distance measuring units 107-1 to 107-6, thereby executing an entire periphery measuring process similar to the operation shown in FIG. 9 (step S131).

Next, the control unit 101 determines whether a predetermined threshold (distance D1) is assured as the distance to the object (the stomach wall 902A in the description (refer to FIG. 14)) in the entire periphery direction of the capsule medical device 10 (step S132). When it is assured (Yes at step S132), the control unit 101 returns to the general operation shown in FIG. 7. In the invention, obviously, whether the distance to be object is equal to or larger than the predetermined threshold (distance D1)) can be replaced with determination of whether the distance is larger than a predetermined threshold.

On the other hand, when a direction in which the predetermined threshold or larger is not assured as the distance between the capsule medical device 10 and the object (stomach wall 902A) exists (No at step S132), one or more acoustic streaming generator 106 for generating a propulsion force in a direction opposite to the direction closest to the object and power given to drive the acoustic streaming generator 106 (power information) is specified on the basis of the peripheral distance obtained in the entire periphery measuring process in step S131 (step S133). The invention, however, is not limited to the configuration. An acoustic streaming generator 106 to be driven and power at the time of the driving may be computed according to an instructed direction each time.

Next, the control unit 101 drives the specified acoustic streaming generator 106 for predetermined time in accordance with the specified power information (step S134). After that, the control unit 101 returns to step S131 and executes similar operation. In such a manner, in the embodiment, the operation is performed so that the distance between the capsule medical device 10 and the object (stomach wall 902A) is maintained to be equal to or larger than the predetermined threshold (distance D1).

By the above operation, in the embodiment, the operation is performed so that the distance between the capsule medical device 10 and the object (stomach wall 902A) is maintained to be equal to or larger than the predetermined threshold (distance D1). Therefore, occurrence of a problem such that the space in which acoustic streaming is generated cannot be assured because the capsule medical device 10 is too close to the object can be prevented.

By providing an acoustic streaming generation plane of the acoustic streaming generator 106 with an acoustic lens for diffusing or converging acoustic streaming, the width (predetermined threshold=distance D1) of an access restricted area AR1 (refer to FIG. 14) can be made shorter. As a result, the travel range of the capsule medical device 10 in the space can be made wider. Thus, the capsule medical device 10 can get closer to the stomach wall 902A and more specific in-vivo information can be obtained.

First Modification

Figure 15:
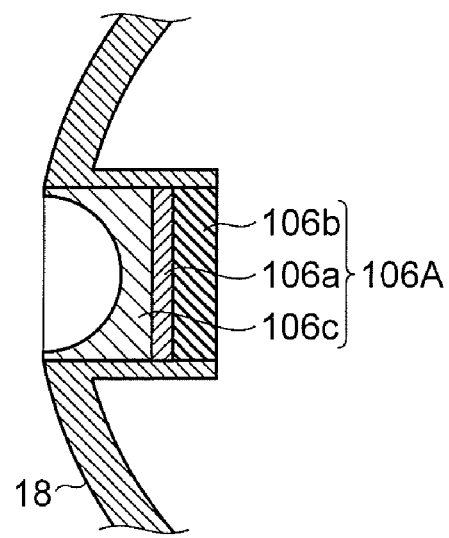
FIG. 15 is a cross section showing a schematic configuration of a first modification of the acoustic streaming generator according to the first embodiment of the invention.

A first modification of the acoustic streaming generator 106 in the first embodiment will be described in detail with reference to the drawings. FIG. 15 is a cross section showing a schematic configuration of an acoustic streaming generator 106A according to the modification. As shown in FIG. 15, the acoustic streaming generator 106A has a configuration similar to that of the acoustic streaming generator 106 that an acoustic lens 106c for enhancing directionality of a sound wave output from the piezoelectric element 106a is provided for the vibration plane of the piezoelectric element 106a as a vibration generator. The acoustic lens 106c has, preferably, a focal point on the inside of the outer package of the capsule medical device 10. By enhancing the directionality of a sound wave generated by the piezoelectric element 106a, the energy density of the sound wave can be increased. Therefore, acoustic streaming which becomes a propulsion force can be generated more efficiently. Further, the acoustic streaming which is generated can be diffused on the outside of the capsule medical device 10, so that the distance to the object necessary to generate sound streaming can be shortened. The acoustic impedance of the acoustic lens 106c is preferably equal to or close to that of the fluid 904 as an acoustic field. At least one of the acoustic streaming generators 106 provided for the capsule medical device 10 has the acoustic lens 106c.

Second Modification

Figure 16:
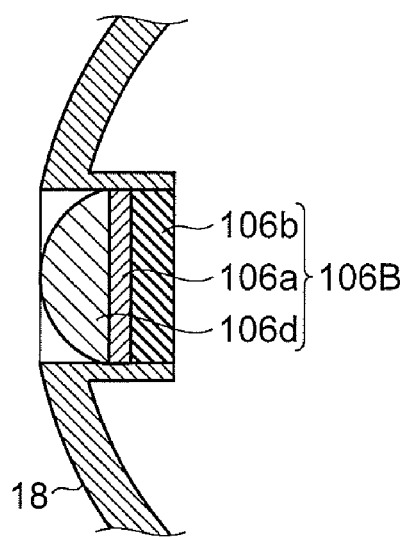
FIG. 16 is a cross section showing a schematic configuration of a second modification of the acoustic streaming generator according to the first embodiment of the invention.

A second modification of the acoustic streaming generator 106 in the embodiment will be described in detail with reference to the drawings. FIG. 16 is a cross section showing a schematic configuration of an acoustic streaming generator 106B according to the modification. As shown in FIG. 16, the acoustic streaming generator 106B has a configuration similar to that of the acoustic streaming generator 106 that an acoustic lens 106d for reducing directionality of a sound wave output from the piezoelectric element 106*a* on the outside of the outer package is provided for the vibration plane of the piezoelectric element 106*a* as a vibration generator. By reducing the directionality of the sound wave generated in the piezoelectric element 106*a*, the acoustic streaming which is generated can be diffused, so that the distance to the object necessary to generate the acoustic streaming can be shortened. The acoustic impedance of the acoustic lens 106*d* is preferably equal to or close to that of the fluid 904 as an acoustic field.

Third Modification

The acoustic lens 106*c* of the first modification or the acoustic lens 106*d* of the second modification may be provided for all or a part of the acoustic streaming generators 106 of the capsule medical device 10. When some of the acoustic streaming generators 106 (for example, the acoustic streaming generators 106-4 to 106-6 in the lower stage) have the acoustic lens 106*c* or 106*d*, the acoustic streaming generator 106 having the acoustic lens 106*c*/106*d* and the acoustic streaming generator 106 having no acoustic lens 106*c*/106*d* can be properly used according to the situation. In the following, the case where the acoustic streaming generators 106-4 to 106-6 in the lower stage have the acoustic lens 106*d* for diffusing acoustic streaming will be described as a third modification of the first embodiment of the invention.

Figure 17:
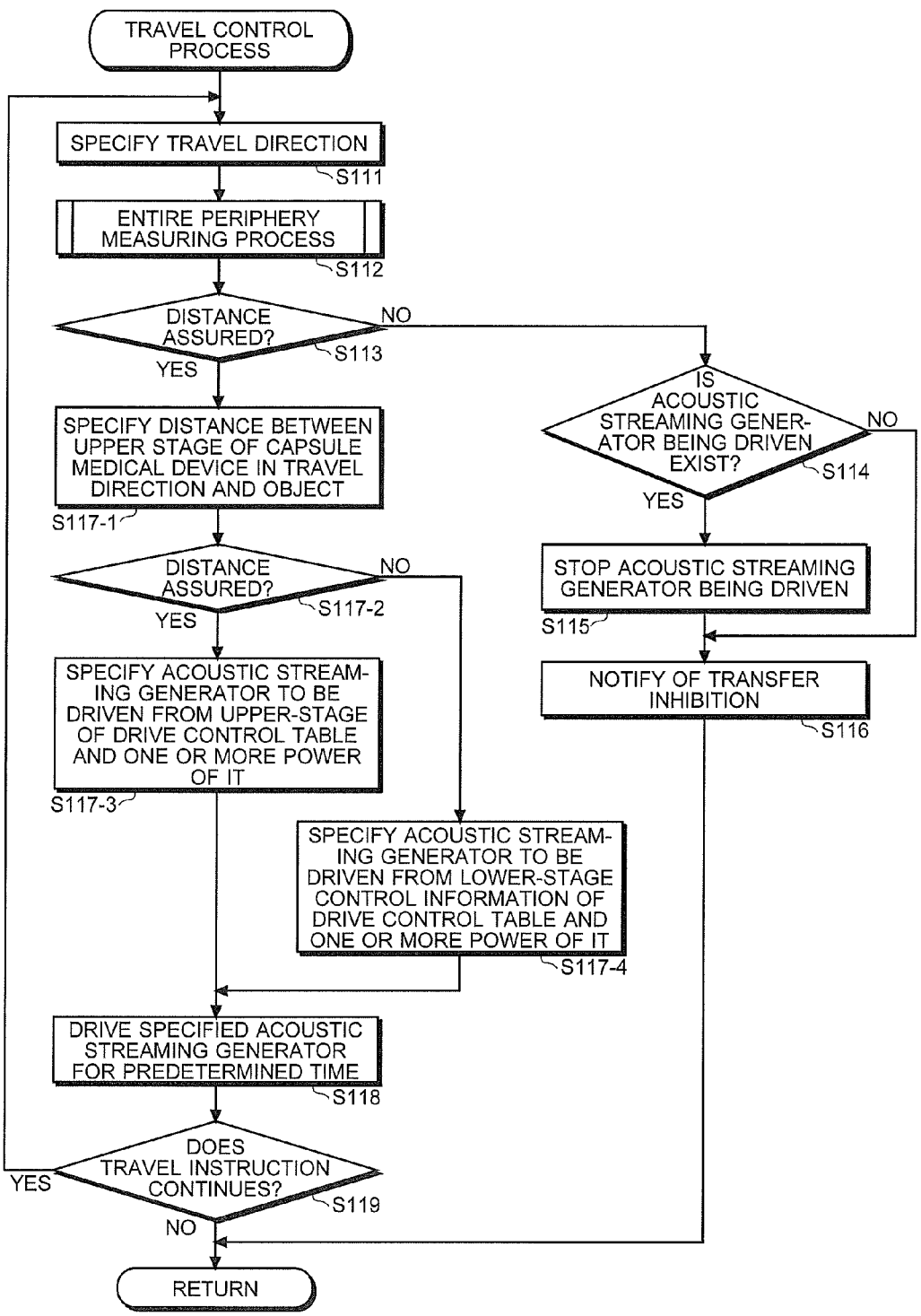
FIG. 17 is a flowchart showing an example of operations in a travel controlling process according to a third modification of the first embodiment of the invention.

In the third modification, in place of the travel control process shown in FIG. 8, the process shown in FIG. 17 is employed. Specifically, when a travel instruction is received from the operation terminal 80 (step S103 in FIG. 7), first, the control unit 101 executes operations similar to those in steps 5111 to 5116 in FIG. 8 (refer to FIGS. 7 and 17). The distance determined to be assured or not in step S113 is a distance in which a propulsion force is obtained even when the acoustic streaming generator 106 having the acoustic lens 106*d* is driven (called a distance D1'). The distance D1' is a distance shorter than the distance D1 in which the propulsion force is obtained when the acoustic streaming generator 106 having no acoustic lens 106*d* is driven. That is, in the third embodiment, the capsule medical device 10 can come closer to the object (stomach wall 902A) as compared with the first embodiment.

Next, when the distance D1' (<D1) is assured as a result of the determination in step S113 (Yes at step S113), the control unit 101 specifies the distance between the upper stage in the capsule medical device 10 in the travel direction and the object (stomach wall 902A) from the peripheral distance specified in step S112 (step S117-1), and determines whether the specified distance is equal to or larger than a predetermined threshold (distance D1>D1') (step S117-2). When it is determined that the distance D1 is assured (Yes at step S117-2), the control unit 101 specifies one or more piece of the acoustic streaming generator 106 (ID) in the upper stage which enables travel in the direction specified as the travel direction in step 5111 and power (power information) to be given at the time of driving the acoustic streaming generator 106 from upper-stage control information in the drive control table (refer to FIG. 11) (step S117-3). On the other hand, when the predetermined threshold (distance D1) is not assured (No at step S117-2), the control unit 101 specifies one or more piece of the acoustic streaming generator 106 (ID) in the lower stage which enables travel in the direction specified as the travel direction in step 5111 and power (power information) to be given at the time of driving the acoustic streaming generator 106 from lower-stage control information in the drive control table (refer to FIG. 11) (step S117-4). The invention, however, is not limited to the configuration. An acoustic streaming generator 106 to be driven according to an instructed direction and power to drive it may be computed each time.

Next, the control unit 101 drives the acoustic streaming generator 106 specified in step S117-3 or S117-4 in accordance with the specified power information for predetermined time (step S118), thereby giving a propulsion force in the travel direction to the capsule medical device 10.

As described above, the propulsion force in the travel direction is given to the capsule medical device 10 by driving one or more acoustic streaming generators 106 specified. After that, the control unit 101 determines whether the travel instruction is continuously received from the operation terminal 80 (step S119). When the travel instruction is continuously received (Yes at step S119), the control unit 101 returns to step S111 and repeats the following operation. On the other hand, when the travel instruction is not continuously received (No at step S119), the control unit 101 returns to the general operation in FIG. 7.

By the above operation, in the third modification, when the predetermined threshold (distance D1) or larger is assured as the distance between the capsule medical device 10 and the object, acoustic streaming having high directionality is generated and a propulsion force can be obtained efficiently. In the third modification, acoustic streaming having low directionality can be generated. Consequently, even when the predetermined threshold (distance D1) or larger cannot be assured as the distance between the capsule medical device 10 and the object, the propulsion force can be given to the capsule medical device 10. That is, the capsule medical device 10 can be allowed to get closer to the object (stomach wall 902A).

Fourth Modification

Figure 18:
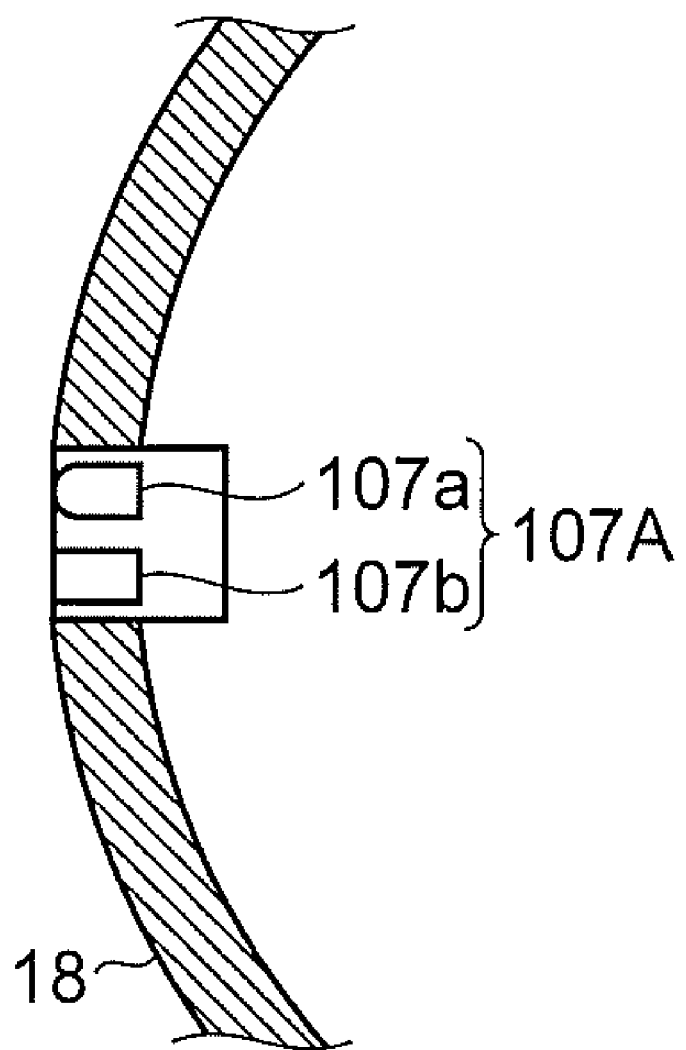
FIG. 18 is a cross section showing a schematic configuration of a fourth modification of the distance measuring unit according to the first embodiment of the invention.

A fourth modification of the distance measuring unit 107 according to the embodiment will be described in detail with reference to the drawings. FIG. 18 is a cross section showing a schematic configuration of a distance measuring unit 107A according to the modification. As shown in FIG. 18, the distance measuring unit 107A is a so-called optical ranging sensor having a light emitting unit 107*a* such as an LED for emitting light using a direction perpendicular to the side face of the capsule medical device 10 as an optical axis and a light receiving unit 107*b* such as a photodiode for detecting light reflected by an object in the light emitted from the light emitting unit 107*a*. Also by using such a distance measuring unit 107A, the configuration and effect similar to those of the foregoing embodiment can be obtained.

Fifth Modification

In the foregoing first embodiment, the case of giving the propulsion force for straight travel to the capsule medical device 10 by generating the acoustic streaming in a direction perpendicular to the outer wall of the capsule medical device 10 from each of the acoustic streaming generators 106 has been described. However, the invention is not limited to the case. For example, a propulsion force for turn can be also given in addition to the propulsion force for straight travel to the capsule medical device 10. A medical system 1A including a capsule medical device 10A constructed as described above will be described in detail as a fifth modification of the first embodiment of the invention with reference to the drawings. In the following, the same reference numeral is designated to the configuration or operation similar to that of the first embodiment of the invention in order to simplify explanation, and its detailed description will not be repeated.

Configuration

Figure 19:
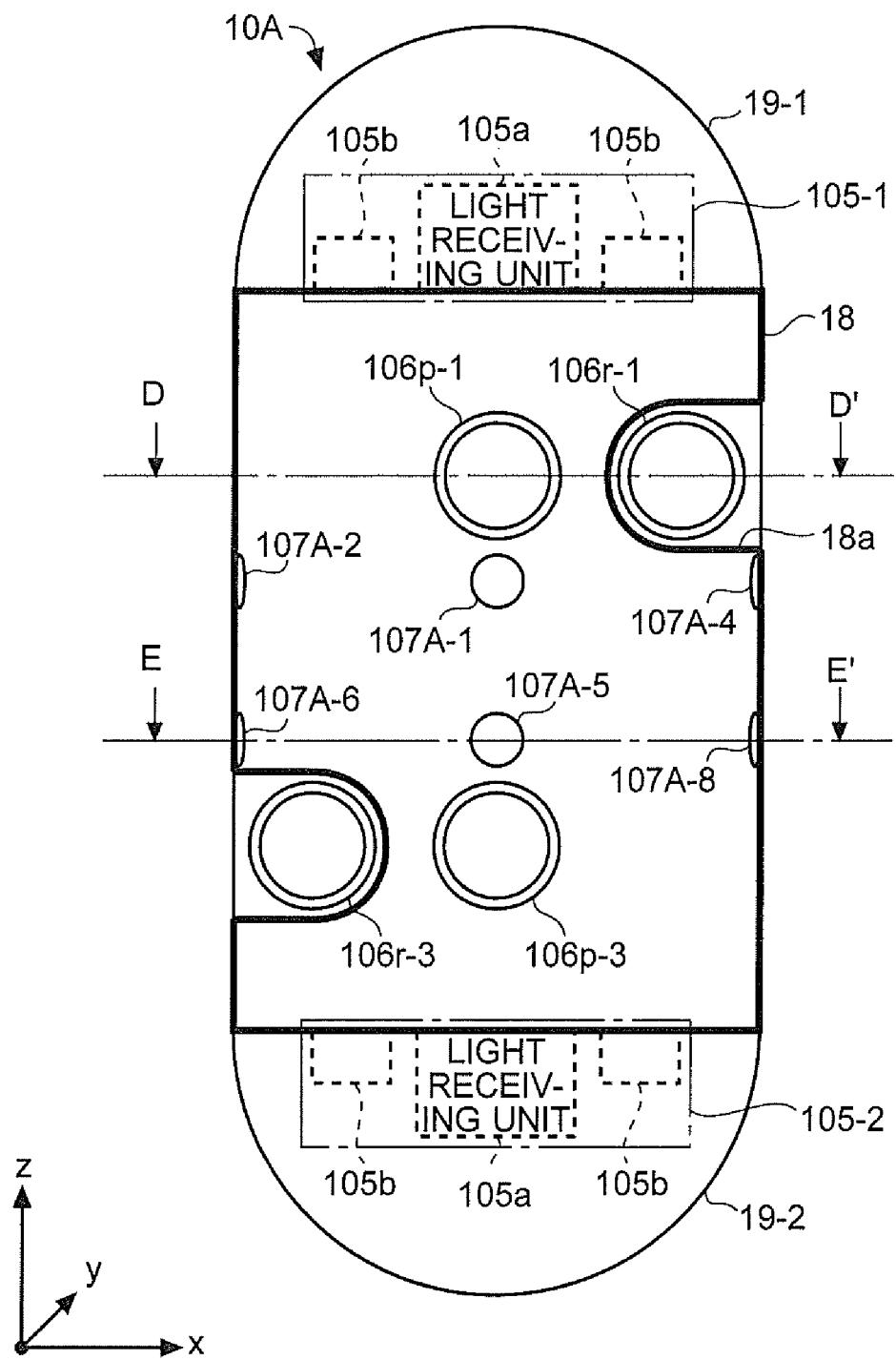
FIG. 19 is an external view showing a capsule medical device according to a fifth modification of the first embodiment of the invention.
Figure 20A:
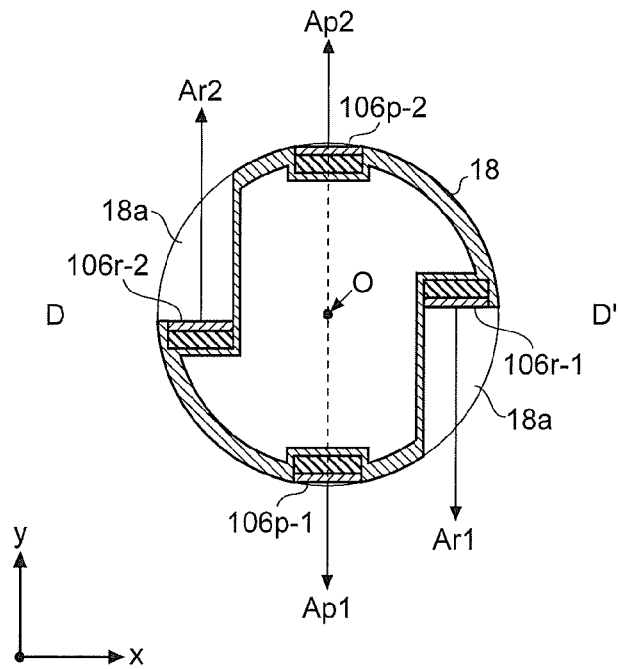
FIG. 20A is a cross-section diagram showing a schematic arrangement configuration in a section taken along line D-D' in FIG. 19.
Figure 20B:
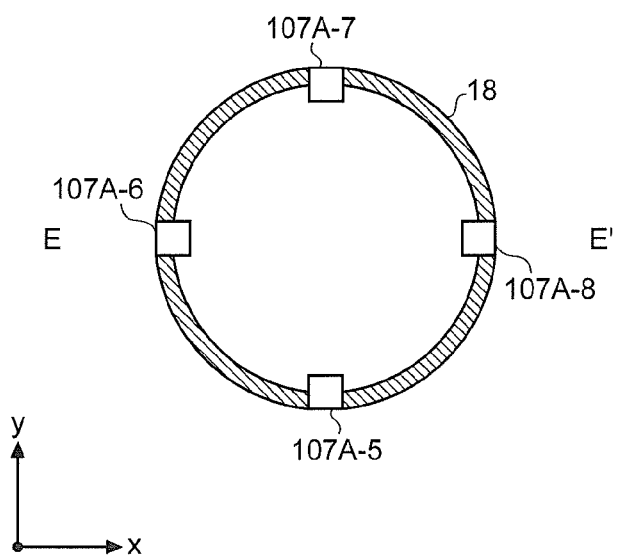
FIG. 20B is a cross-section diagram showing a schematic arrangement configuration in a section taken along line E-E' in FIG. 19.

FIG. 19 is an external view showing a schematic configuration of the capsule medical device 10A according to the fifth modification. FIG. 20A is a cross-section diagram showing a schematic arrangement configuration in a section taken along line D-D' in FIG. 19. FIG. 20B is a cross-section diagram showing a schematic arrangement configuration in a section taken along line E-E' in FIG. 19. FIG. 21 is a block diagram showing a schematic configuration of the medical system 1A made by the capsule medical device 10A according to the fifth modification and the operation terminal 80 connected to the capsule medical device 10A via radio waves.

Capsule Medical Device

As shown in FIGS. 19 and 20A, the capsule medical device 10A has: four acoustic streaming generators for straight travel (first acoustic streaming generators) 106$p$-1 to 106$p$-4 disposed so that an extension line of acoustic streaming axes Ap1/Ap2 passes through the center "O" of the capsule medical device 10A and the acoustic streaming axis Ap2 extends in the direction normal to the side face of the body portion 18 of the capsule medical device 10A; and acoustic streaming generators for turn (second acoustic streaming generators) 106$r$-1 to 106$r$-4 disposed so that an extension line of acoustic streaming axis Ar2 does not pass through the center "O" of the capsule medical device 10A and the acoustic streaming axes Ar1/Ar2 are included in a plane slicing the body portion 18 of the capsule medical device 10A.

The acoustic streaming generators 106$p$-1 to 106$p$-4 for straight travel are acoustic streaming generators for giving a propulsion force for straight travel to the capsule medical device 10A. Two of them are disposed in an upper stage and the remaining two generators are disposed in a lower stage. The two acoustic streaming generators 106$p$-1 and 106$p$-2 for straight travel in the upper and lower stages are disposed so as to be directed in opposite directions, and the two acoustic streaming generators 106$p$-3 and 106$p$-4 for straight travel disposed in the upper and lower stages are disposed so as to be directed in opposite directions. Preferably, at least one of the acoustic streaming generators 106$p$-1 to 106$p$-4 for straight travel has the acoustic lens.

On the other hand, the acoustic streaming generators 106$r$-1 to 106$r$-4 for turn are acoustic streaming generators for giving a turn force to the capsule medical device 10A. Two of them are disposed in an upper stage and the remaining two generators are disposed in a lower stage. The two acoustic streaming generators 106$r$-1 and 106$r$-2 for turn disposed in the upper stage and the two acoustic streaming generators 106$r$-3 and 106$r$-4 for turn disposed in the lower stage are disposed so as to give turn forces in opposite directions to the capsule medical device 10A. In the body portion 18 of the casing of the capsule medical device 10A, trenches 18$a$ are provided along the flows of the acoustic streaming generated by the acoustic streaming generators 106$r$ for turn. In the following description, the reference numeral of arbitrary one of the acoustic streaming generators 106$p$-1 to 106$p$-4 will be 106$p$, that of arbitrary one of the acoustic streaming generators 106$r$-1 to 106$r$-4 for turn will be 106$r$, and that of arbitrary one of distance measuring units 107A-1 to 107A-8 will be 107A.

As shown in FIGS. 19 and 20B, four out of the distance measuring units 107A-1 to 107A-8 are disposed in the upper stage of the capsule medical device 10A, and the other four are disposed on the lower stage. The optical axes of the distance measuring units 107A-1 to 107A-4 in the upper stage are deviated by 90°, and those of the distance measuring units 107A-5 to 107A-8 in the lower stage are deviated by 90°. With the configuration, in each of the upper and lower stages of the capsule medical device 10A, the distances to objects in four ways can be measured. In the fifth modification, each of the distance measuring units 107A-1 to 107A-8 is constructed by, for example, an optical distance ranging sensor described in the fourth modification.

The capsule medical device 10A according to the fifth modification having such a configuration drives the acoustic streaming generators 106$r$ for turn to turn the acoustic streaming generators 106$p$ for straight travel in a direction opposite to the travel direction and, in this state, drives the acoustic streaming generators 106$p$ to make the capsule medical device 10A travel. Since the other configuration is similar to that of the first embodiment of the invention, the detailed description will not be repeated.

Operation

Figure 22:
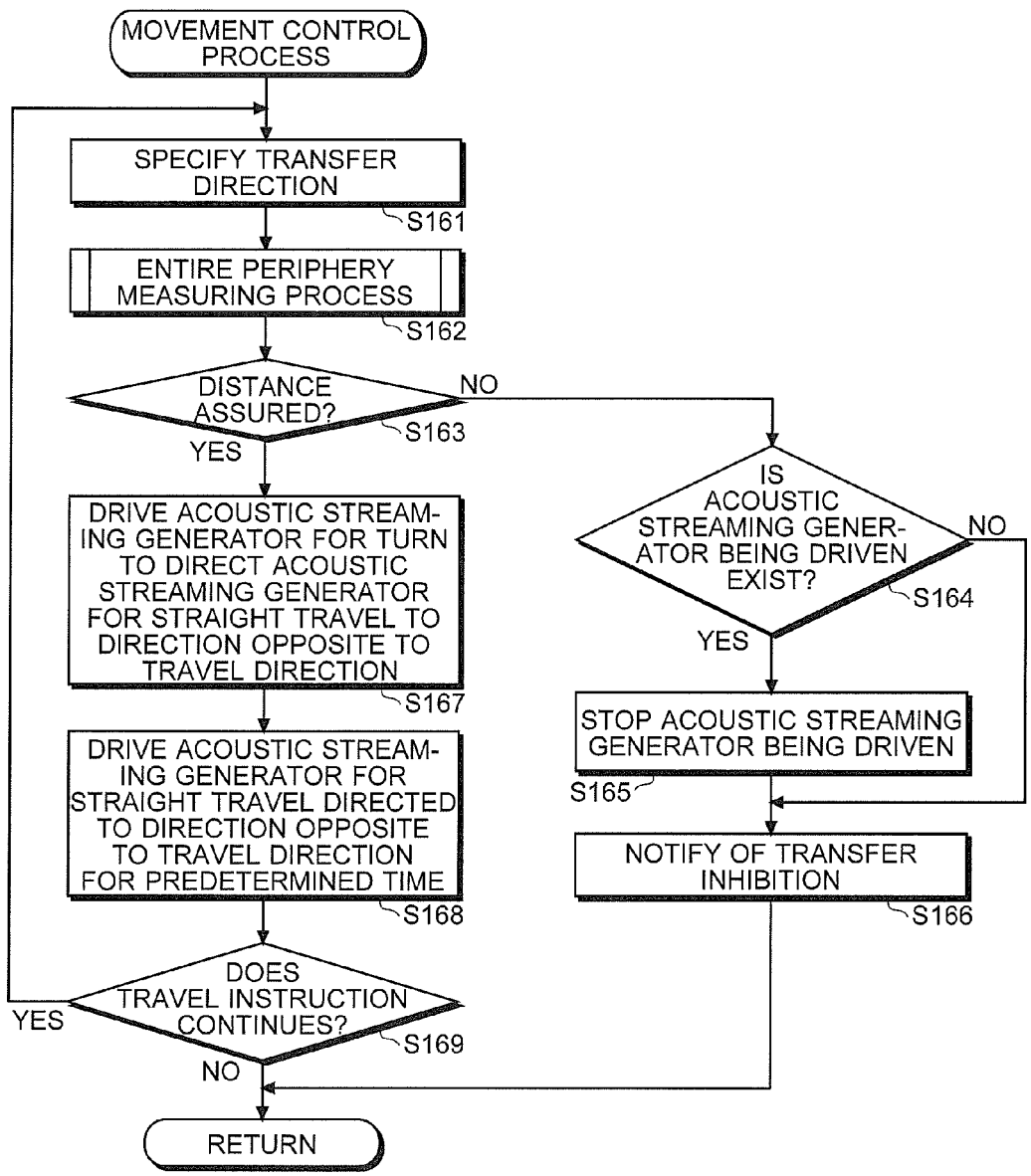
FIG. 22 is a flowchart showing an example of operation in a travel control process according to the fifth modification of the first embodiment of the invention.
Figure 23:
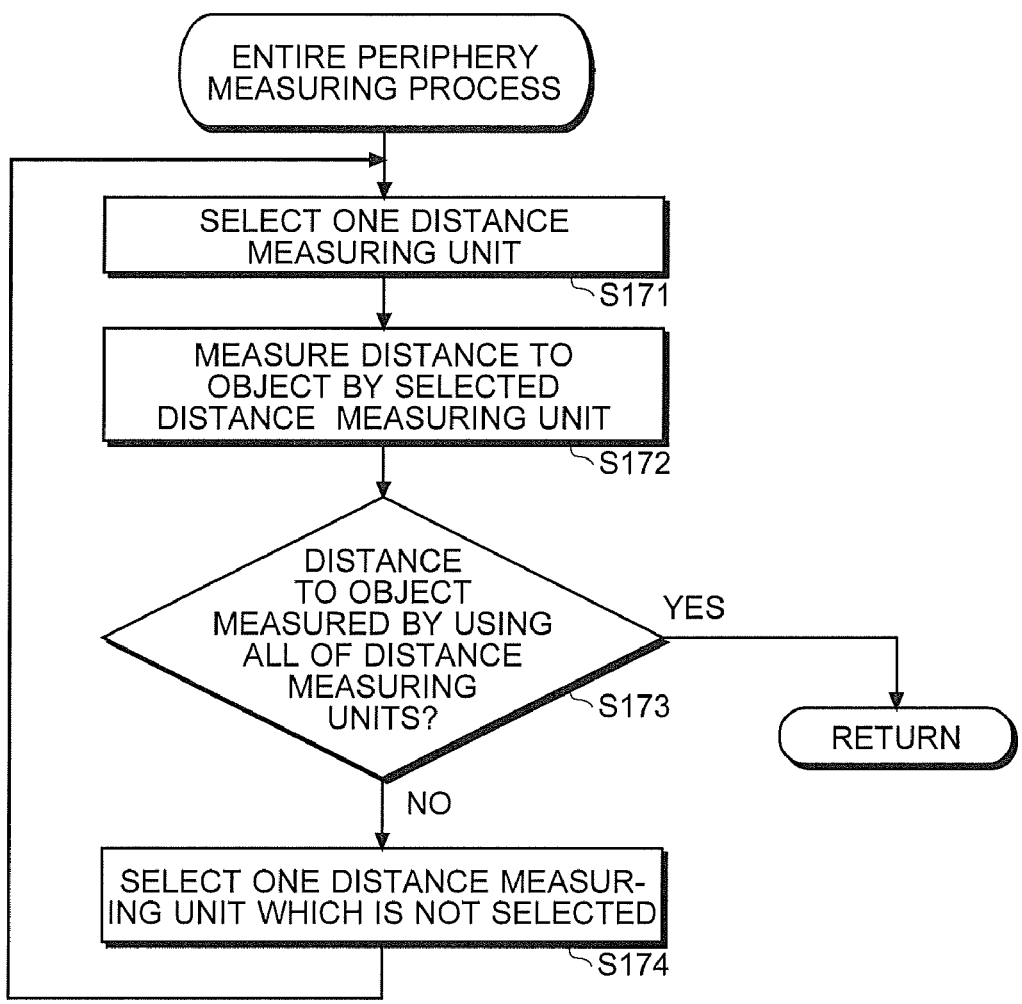
FIG. 23 is a flowchart showing an example of operation in an entire periphery measuring process according to the fifth modification of the first embodiment of the invention.

Next, the operation performed at the time of operating the capsule medical device 10A by using the operation terminal 80 in the fifth modification will be described in detail with reference to the drawings. FIG. 22 is a flowchart showing an example of operations of the travel control process according to the fifth modification. FIG. 23 is a flowchart showing an example of operations of the entire periphery measuring process according to the fifth modification. In the fifth modification, the general operation at the time of operating the capsule medical device 10A by using the operation terminal 80 is similar to that described with reference to FIG. 7 in the first embodiment of the invention, so that its detailed description will not be repeated.

As shown in FIG. 22, in the travel control process (step S103 in FIG. 7) according to the fifth modification, the control unit 101 specifies, first, the travel direction of the capsule medical device 10A determined by a travel instruction (step S161). Next, by sequentially driving, for example, all of the distance measuring units 107A, the control unit 101 executes the entire periphery measuring process of obtaining distances to the object from the entire periphery of the capsule medical device 10A (peripheral distances) (step S162). The details of the entire periphery measuring process will be described later with reference to FIG. 23.

Next, the control unit 101 determines whether a distance equal to or longer than a predetermined threshold (distance D1) to an object (stomach wall 902A) in the travel direction specified in step S161 is assured on the basis of the periphery distance obtained in step S162 (step S163). When a distance corresponding to the predetermined threshold (distance D1) is assured (Yes at step S163), the control unit 101 moves to step S167. On the other hand, when the distance is not assured (No at step S163), the control unit 101 determines whether the acoustic streaming generator 106$p$ for straight travel which is being driven and/or the acoustic streaming generator 106$r$ for turn exists (step S164). When it exists (Yes at step S164), the control unit 101 stops the acoustic streaming generator (106$p$/106$r$) being driven (step S165). After that, the control unit 101 notifies the operation terminal 80 of the state that travel in the direction entered by the operation terminal 80 is not allowed (step S166) and returns to the general operation in FIG. 7. On the other hand, when the acoustic streaming generator (106$p$/106$r$) which is being driven does not exist (No at step S164), the control unit 101 moves to step S166, notifies the operation terminal 80 of the state that travel is not allowed and, after that, returns to the general operation in FIG. 7. The operation terminal 80 which is notified of the state that travel in the instructed direction is not allowed displays the state on the display unit 81 or notifies the operator of the state by sound or voice from a not-shown speaker.

When the predetermined threshold (distance D1) is not assured as a result of determination in step S163 (No at step S163), the control unit 101 determines whether the capsule medical device 10A is traveling. If the capsule medical device 10 is traveling, the control unit 101 may properly drive the acoustic streaming generator 106r for turn and/or the acoustic streaming generator 106p for straight travel to temporarily generate a propulsion in a direction opposite to the travel direction of the capsule medical device 10A, thereby making the capsule medical device 10A stationary. Whether the capsule medical device 10A is presently traveling can be known by using various methods such as a method of determining it by using a not-shown acceleration sensor, a method of determining it from an image captured periodically by the imaging unit 105, and a method of determining it from a periphery distance obtained by periodically executing the entire periphery measuring process.

In step S167, the control unit 101 turns any one or more of acoustic streaming generators 106p for straight travel in a direction opposite to the direction specified as the travel direction in step S161 by driving one or more acoustic streaming generators 106r for turn (step S167), and drives the acoustic streaming generators 106p for straight travel for predetermined time (step S168). By the driving, a propulsion force is given to the capsule medical device 10A. After that, the control unit 101 moves to step S169. To stop turn of the capsule medical device 10A, the acoustic streaming generator 106r in the opposite direction may be driven for predetermined time. It is sufficient to select the acoustic streaming generator 106p for straight travel whose rotational amount is smaller as the acoustic streaming generator 106p for straight travel which is turned in the direction opposite to the travel direction.

After driving the specified acoustic streaming generator 106p for straight travel to give the propulsion force in the travel direction to the capsule medical device 10A as described above, the control unit 101 determines whether the travel instruction is continuously received from the operation terminal 80 (step S169). When the travel instruction is continuously received (Yes at step S169), the control unit 101 returns to step S161 and repeats the following operation. On the other hand, when the travel instruction is not continuously received (No at step S169), the control unit 101 returns to the general operation in FIG. 7.

The capsule medical device 10A as the capsule propulsion device according to the fifth modification, which is introduced in a space (the stomach 902) in which a medium for transmitting a sound wave exists, includes: a plurality of acoustic streaming generators (acoustic streaming generators 106p-1 to 106p-4 for straight travel and acoustic streaming generators 106r-1 to 106r-4 for turn) for generating acoustic streaming as a flow of the a medium in the stomach 902; the distance obtaining unit (the distance measuring units 107A-1 to 107A-8 and the control unit 101) for obtaining an object distance between the acoustic streaming generators (106p-1 to 106p-4 and 106r-1 to 106r-4) and the object (stomach wall 902A) existing in the direction of the flow of the acoustic streaming generated by the acoustic streaming generators 106p-1 to 106p-4 and 106r-1 to 106r-4); and the control unit 101 for performing driving and control to make the acoustic streaming generator 106p or 106r having an object distance equal to or longer than a predetermined threshold (distance D1) generate acoustic streaming. With the configuration, the capsule medical device 10A capable of traveling in a desired direction regardless of the position and orientation in the subject 900 and the medical system 1A having the same can be realized.

Entire Periphery Measuring Process

The entire periphery measuring process shown in step S162 in FIG. 22 will be described in detail with reference to the drawings. FIG. 23 is a flowchart showing the flow of the entire periphery measuring process according to the fifth modification.

As shown in FIG. 23, in the entire periphery measuring process (step S181 in FIG. 24), first, the control unit 101 selects any one of the distance measuring units 107A-1 to 107A-8 (step S171), drives a light emitting unit in the selected distance measuring unit 107A (corresponding to the light emitting unit 107a in FIG. 18) to emit measurement light, and detects reflection light of the measurement light by using a light receiving unit (corresponding to the light receiving unit 107b in FIG. 18), thereby measuring the distance to the object (step S172). The measurement value is input to the control unit 101 and the distance to the object is calculated in the control unit 101.

Next, the control unit 101 determines whether the distance to the object is calculated by using all of the distance measuring units 107A (step S173). In the case of "No" (No at step S173), the control unit 101 selects one of the distance measuring units 107A which are not selected (step S174), after that, returns to step S171, and repeats the subsequent operations until the distance to the object is calculated by using all of the distance measuring units 107A. On the other hand, when the distance to the object is calculated by all of the distance measuring units 107A (Yes at step S173), the control unit 101 returns to the object distance assuring process shown in FIG. 24.

As described above, by measuring the distance to an object by using the distance measuring units 107A disposed along the entire periphery of the capsule medical device 10A, the distances (periphery distance) to the object from the entire periphery of the capsule medical device 10A can be obtained.

Object Distance Assuring Process

Figure 24:
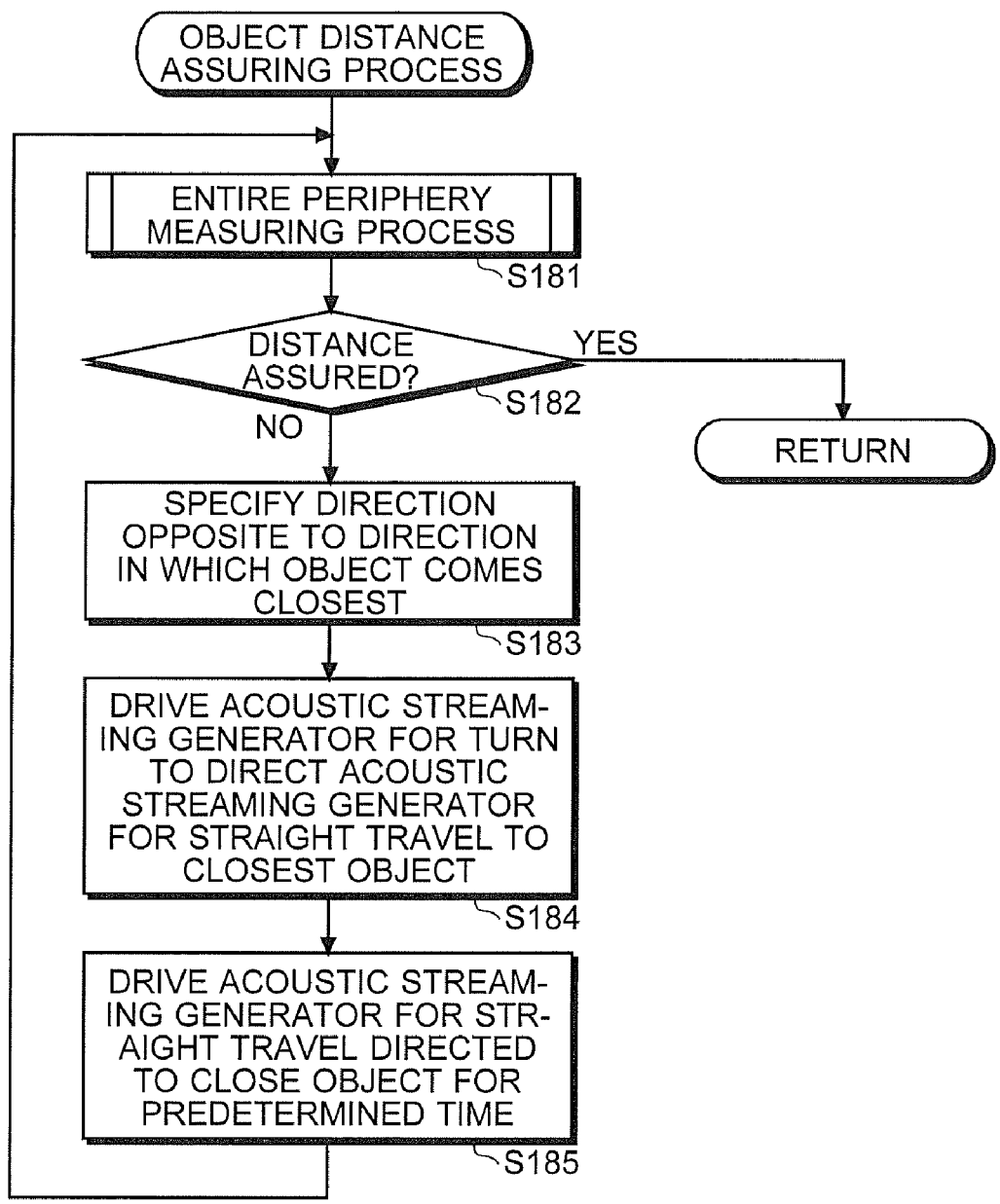
FIG. 24 is a flowchart showing an example of operation in an object distance assuring process according to the fifth modification of the first embodiment of the invention.

Also in the fifth modification, like in the first embodiment of the invention, the object distance assuring process may be periodically executed in the flow of the general operation (refer to FIG. 7). FIG. 24 is a flowchart showing the flow of the object distance assuring process according to the fifth modification.

As shown in FIG. 24, in the object distance assuring process according to the fifth modification, first, the control unit 101 sequentially drives, for example, all of the distance measuring units 107A, thereby executing an entire periphery measuring process similar to the operation shown in FIG. 23 (step S181).

Next, the control unit 101 determines whether a predetermined threshold (distance D1) is assured as the distance to the object (the stomach wall 902A) in the entire periphery direction of the capsule medical device 10A (step S182). When it is assured (Yes at step S182), the control unit 101 returns to the general operation shown in FIG. 7.

On the other hand, when a direction in which the predetermined threshold or larger is not assured as the distance between the capsule medical device 10A and the object (stomach wall 902A) exists (No at step S182), the control unit 101 specifies the direction opposite to the direction in which the capsule medical device 10A was closest to the object on the basis of the peripheral distance obtained in the entire periphery measuring process in step S181 (step S183) and, subsequently, drives the acoustic streaming generator 106r for turn to turn the capsule medical device 10A, thereby directing the acoustic streaming generator 106p for straight travel toward the closest object (step S184). To stop the turn of the capsule medical device 10A, the acoustic streaming generator 106r for turn in the opposite direction may be driven for predetermined time. It is preferable to use the acoustic streaming generator 106p for straight travel with a smallest turn amount as an acoustic streaming generator 106p for straight travel which is directed toward the closest object.

Next, the control unit 101 drives the acoustic streaming generator 106p directed toward the closest object for predetermined time (step S185). In the fifth modification, even when the capsule medical device 10A comes close to the object (stomach wall 902A), the acoustic streaming generator (the acoustic streaming generator 106p for straight travel or the acoustic streaming generator 106r for turn) in a position far from the object is selected and driven so that the travel direction can be entered. After that, the control unit 101 returns to step S181 and executes similar operation.

By the above operation, in the fifth modification, the distance between the capsule medical device 10A and the object (stomach wall 902A) is maintained to be equal to or longer than the predetermined threshold (distance D1). Therefore, occurrence of a problem such that the space for generating acoustic streaming cannot be assured for a reason that the capsule medical device 10 comes too close to the object can be prevented.

By providing an acoustic streaming generation plane of the acoustic streaming generator 106p for straight travel and/or the acoustic streaming generator 106r for turn with an acoustic lens for diffusing or converging acoustic streaming, the width D1 (predetermined threshold) of the access restricted area AR1 (refer to FIG. 14) can be made shorter. As a result, the travel range of the capsule medical device 10A in the space can be made wider. Thus, the capsule medical device 10A can get closer to the stomach wall 902A and more specific in-vivo information can be obtained.

Second Embodiment

The configuration and operation of a medical system according to a second embodiment of the invention will be described in detail with reference to the drawings. In the following, the same reference numeral is designated to the configuration or operation similar to that of the first embodiment of the invention in order to simplify explanation, and its detailed description will not be repeated. In the second embodiment, the case of using a configuration similar to that of the medical system 1 in the first embodiment of the invention will be described as an example. However, the invention is not limited to the case but the second embodiment can be applied to all of embodiments described here.

Figure 25:
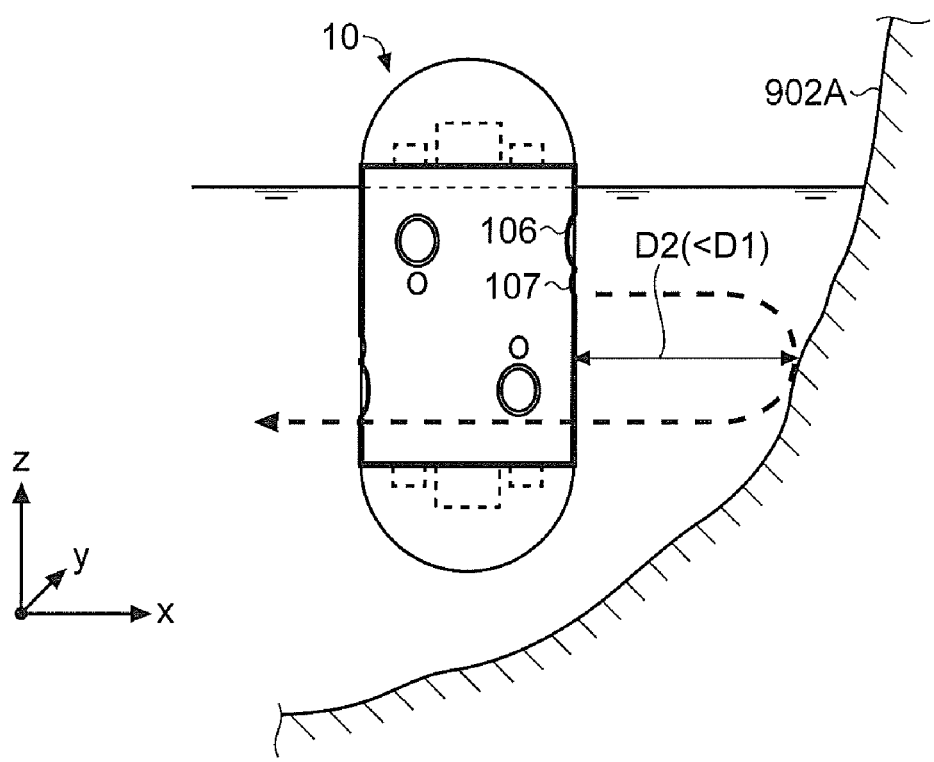
FIG. 25 is a conceptual diagram for explaining movement of a capsule medical device according to a second embodiment of the invention.

FIG. 25 is a schematic diagram for explaining movement of the capsule medical device 10 according to the second embodiment. As shown in FIG. 25, in the embodiment, when the distance D2 between the capsule medical device 10 and the object becomes less than the predetermined threshold (distance D1), the capsule medical device 10 is hit against the object and, by using the reaction, maintains the distance between the capsule medical device 10 and the object to the predetermined threshold (distance D1) or larger.

Operation

Figure 26:
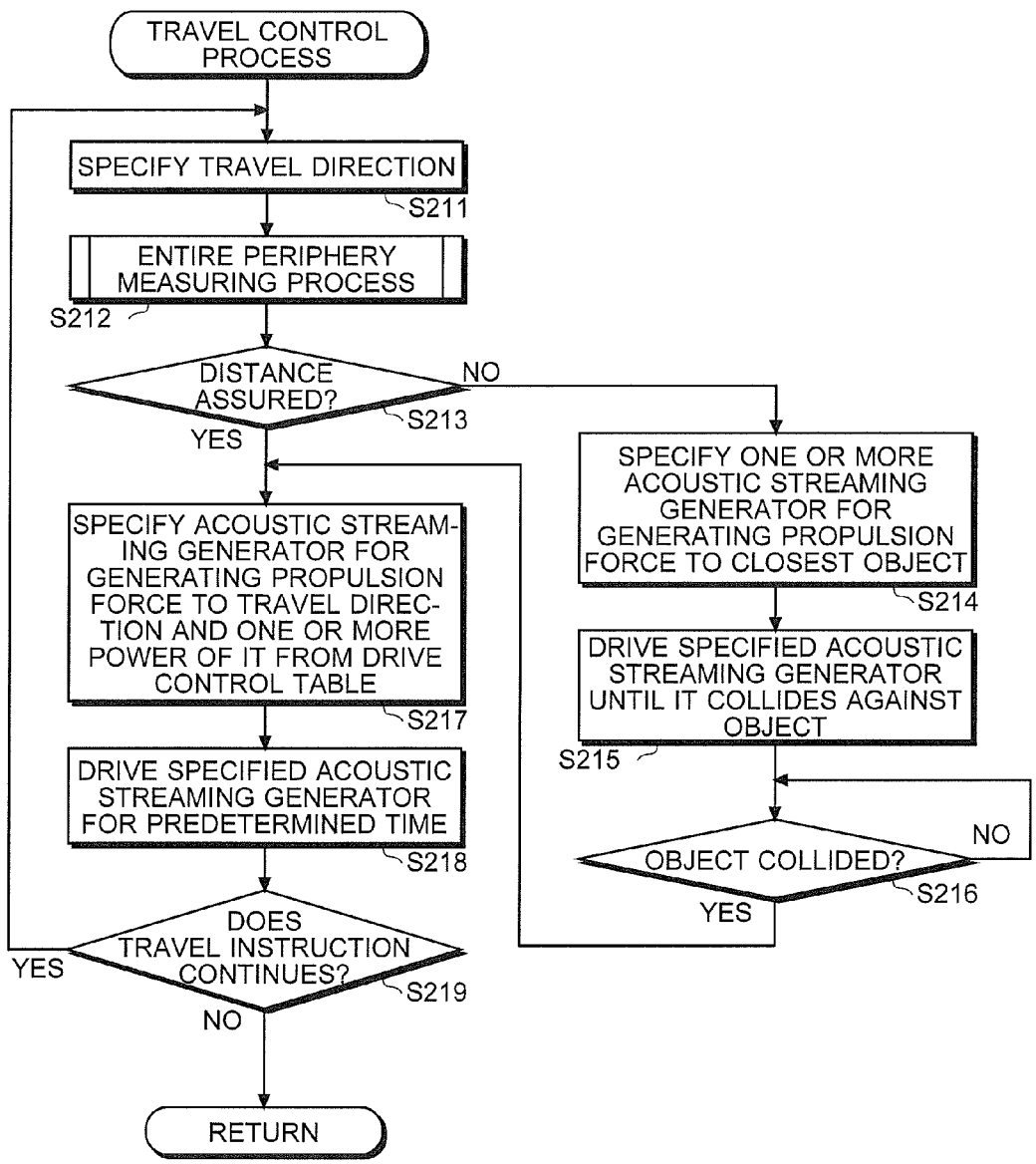
FIG. 26 is a flowchart showing an example of operations in a travel controlling process according to the second embodiment of the invention.

The operation performed at the time of operating the capsule medical device 10 by using the operation terminal 80 in the embodiment will be described in detail with reference to the drawings. FIG. 26 is a flowchart showing an example of operations in a travel controlling process according to the second embodiment. Since the general operation at the time of operating the capsule medical device 10 by using the operation terminal 80 and the entire periphery measuring process in the second embodiment are similar to those described with reference to FIGS. 7 and 9 in the first embodiment of the invention, their detailed description will not be repeated.

Travel Control Process

As shown in FIG. 26, in the travel control process (step S103 in FIG. 7) of the embodiment, first, the control unit 101 specifies the travel direction of the capsule medical device 10 instructed by the travel instruction (step S211). Next, the control unit 101 executes an operation similar to that of the entire periphery measuring process described with reference to FIG. 9 in the first embodiment, thereby executing the entire periphery measuring process of obtaining the distance to an object in the entire periphery of the capsule medical device 10 (step S212).

Next, the control unit 101 determines whether a distance equal to or longer than a predetermined threshold (distance D1) is assured between a drive force generator to be driven for a travel in the travel direction specified in step S211 and the object (stomach wall 902A) on the basis of the periphery distance obtained in step S212 (step S213). When a distance corresponding to the predetermined threshold (distance D1) is assured (Yes at step S213), the control unit 101 moves to step S217. On the other hand, when the distance is not assured (No at step S213), the control unit 101 specifies one or more acoustic streaming generators 106 for generating a propulsion force in a direction toward the object closest to the capsule medical device 10 from a drive control table (refer to FIG. 11) on the basis of the periphery distance obtained in step S212 (step S214). The control unit 101 drives the specified acoustic streaming generator 106 until the capsule medical device 10 collides against the object (step S215 and No at S216). Whether the capsule medical device 10 collides against the object can be determined (S216) by any of various methods such as a method of determining it by using a not-shown acceleration sensor, a method of determining it from an image captured periodically by the imaging unit 105, and a method of determining it from a periphery distance obtained by periodically executing the entire periphery measuring process. After collision against the object (Yes at step S216), the control unit 101 moves to step S217.

In step S217, the control unit 101 specifies the acoustic streaming generator 106 (its ID) which enables travel in the direction specified as the travel direction in step S211 and one or more powers (power information) to be given at the time of driving the acoustic streaming generators 106 from the above-described drive control table (refer to FIG. 11). The invention is not limited to the configuration but may employ a configuration of specifying the acoustic streaming generator to be driven in accordance with the instructed direction and computing the power at the time of driving the acoustic streaming generator each time. It is sufficient to select the acoustic streaming generator 106 specified in step S217 in consideration of balance on the capsule medical device 10, of the propulsion force generated from the acoustic streaming generators 106 on the upper and lower stages.

Next, the control unit 101 drives the acoustic streaming generator 106 specified in step S217 in accordance with the power information similarly specified for predetermined time (step S218). By the driving, the propulsion force in the travel direction is given to the capsule medical device 10.

As described above, when one or more acoustic streaming generators 106 specified is/are driven to give the propulsion force in the travel direction to the capsule medical device 10, the control unit 101 determines whether the travel instruction is continuously received from the operation terminal 80 (step S219). When the travel instruction is continuously received (Yes at step S219), the control unit 101 returns to step S211 and repeats the following operation. On the other hand, when the travel instruction is not continuously received (No at step S219), the control unit 101 returns to the general operation in FIG. 7.

In a manner similar to the first embodiment, the capsule medical device 10 as the capsule propulsion device according to the second embodiment, which is introduced in a space (the stomach 902) in which a medium for transmitting a sound wave exists, includes: a plurality of acoustic streaming generators 106-1 to 106-6 for generating acoustic streaming as a flow of the a medium in the stomach 902; the distance obtaining unit (the distance measuring units 107-1 to 107-6 and the control unit 101) for obtaining an object distance between the acoustic streaming generators 106-1 to 106-6 and the object (stomach wall 902A) existing in the direction of the flow of the acoustic streaming generated by the acoustic streaming generators 106-1 to 106-6; and the control unit 101 for performing driving and control to make the acoustic streaming generator 106 having an object distance equal to or longer than a predetermined threshold (distance D1) generate acoustic streaming. With the configuration, the capsule medical device 10 capable of traveling in a desired direction regardless of the position and orientation in the subject 900 and the medical system 1 having the same can be realized.

Object Distance Assuring Process

Figure 27:
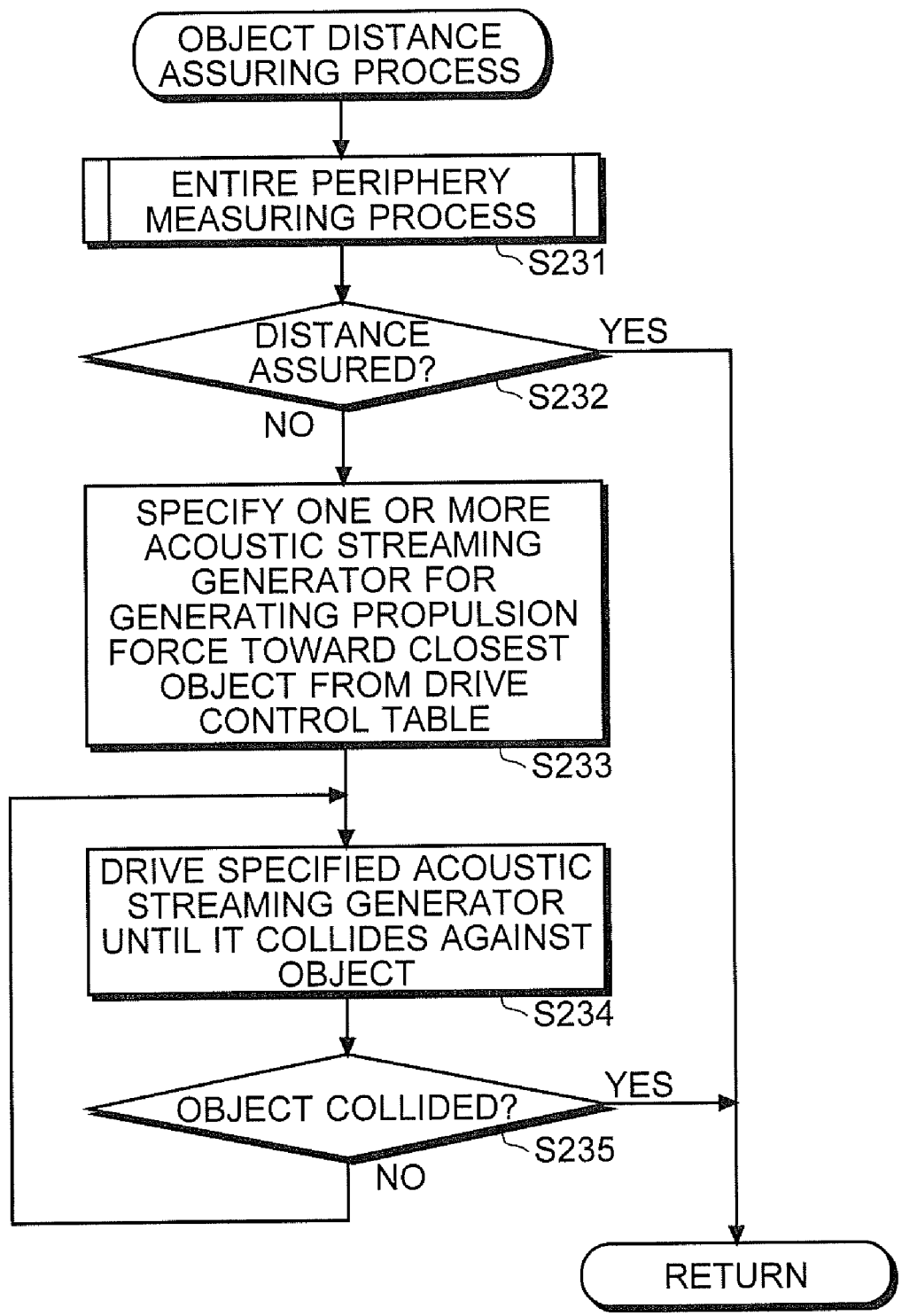
FIG. 27 is a flowchart showing an example of operations in an object distance assuring process according to the second embodiment of the invention.

Also in the second embodiment, in a manner similar to the first embodiment of the invention, the object distance assuring process (refer to FIG. 13) may be periodically executed in the flow of the general operation (refer to FIG. 7). FIG. 27 is a flowchart showing the flow of the object distance assuring process according to the second embodiment.

As shown in FIG. 27, in the object distance assuring process according to the embodiment, first, the control unit 101 sequentially drives, for example, all of the acoustic streaming generators 106-1 to 106-6 and all of the distance measuring units 107-1 to 107-6, thereby executing an entire periphery measuring process similar to the operation shown in FIG. 9 (step S231).

Next, the control unit 101 determines whether a predetermined threshold (distance D1) is assured as the distance to the object (the stomach wall 902A) in the entire periphery direction of the capsule medical device 10 (step S232). When it is assured (Yes at step S232), the control unit 101 returns to the general operation shown in FIG. 7.

On the other hand, when a direction in which the predetermined threshold or larger is not assured as the distance between the capsule medical device 10 and the object (stomach wall 902A) exists (No at step S232), the control unit 101 specifies one or more acoustic streaming generator 106 for generating a propulsion force in a direction of approaching the object closest to the capsule medical device 10 from the drive control table (refer to FIG. 11) on the basis of the periphery distance obtained in the entire periphery measuring process in step S231 (step S233), and drives the specified acoustic streaming generator 106 until the capsule medical device 10 collides against the object (step S234 to No at step S235). Whether the capsule medical device 10 collides against the object (step S235) can be determined by using various methods such as a method of determining it by using a not-shown acceleration sensor, a method of determining it from an image captured periodically by the imaging unit 105, and a method of determining it from a periphery distance obtained by periodically executing the entire periphery measuring process. After collision with an object (Yes at step S235), the control unit 101 returns to the general operation shown in FIG. 7. In such a manner, in the embodiment, the distance between the capsule medical device 10 and the object (stomach wall 902A) is maintained to the predetermined threshold (distance D1) or larger.

By the above operation, in the embodiment, also when the distance between the capsule medical device 10 and the object (stomach wall 902A) becomes less than the predetermined threshold (distance D1), the distance between the capsule medical device 10 and the object (stomach wall 902A) can be reset to the predetermined threshold (distance D1) or longer by the reaction of the collision with the object. Thus, occurrence of a problem such that the space for generating acoustic streaming cannot be assured because the capsule medical device 10 comes too close to the object can be prevented. Further, even when the capsule medical device 10 is introduced in the stomach 902 first and the distance to the object (for example, the stomach wall 902A) is shortened, by periodically performing the object distance assuring process in short cycles, the capsule medical device 10 can be moved in a direction according to an input from the operator.

By providing an acoustic streaming generation plane of the acoustic streaming generator 106 with an acoustic lens for diffusing or converging acoustic streaming, the space necessary for generation of acoustic streaming (distance to the object) can be made shorter. As a result, the travel range of the capsule medical device 10 in the space can be made wider. Thus, the capsule medical device 10 can get closer to the stomach wall 902A and more specific in-vivo information can be obtained.

Third Embodiment

The configuration and operation of a medical system 3 according to a third embodiment of the invention will be described in detail with reference to the drawings. In the following, the same reference numeral is designated to the configuration or operation similar to that of the first or second embodiment of the invention in order to simplify explanation, and its detailed description will not be repeated.

Figure 28A:
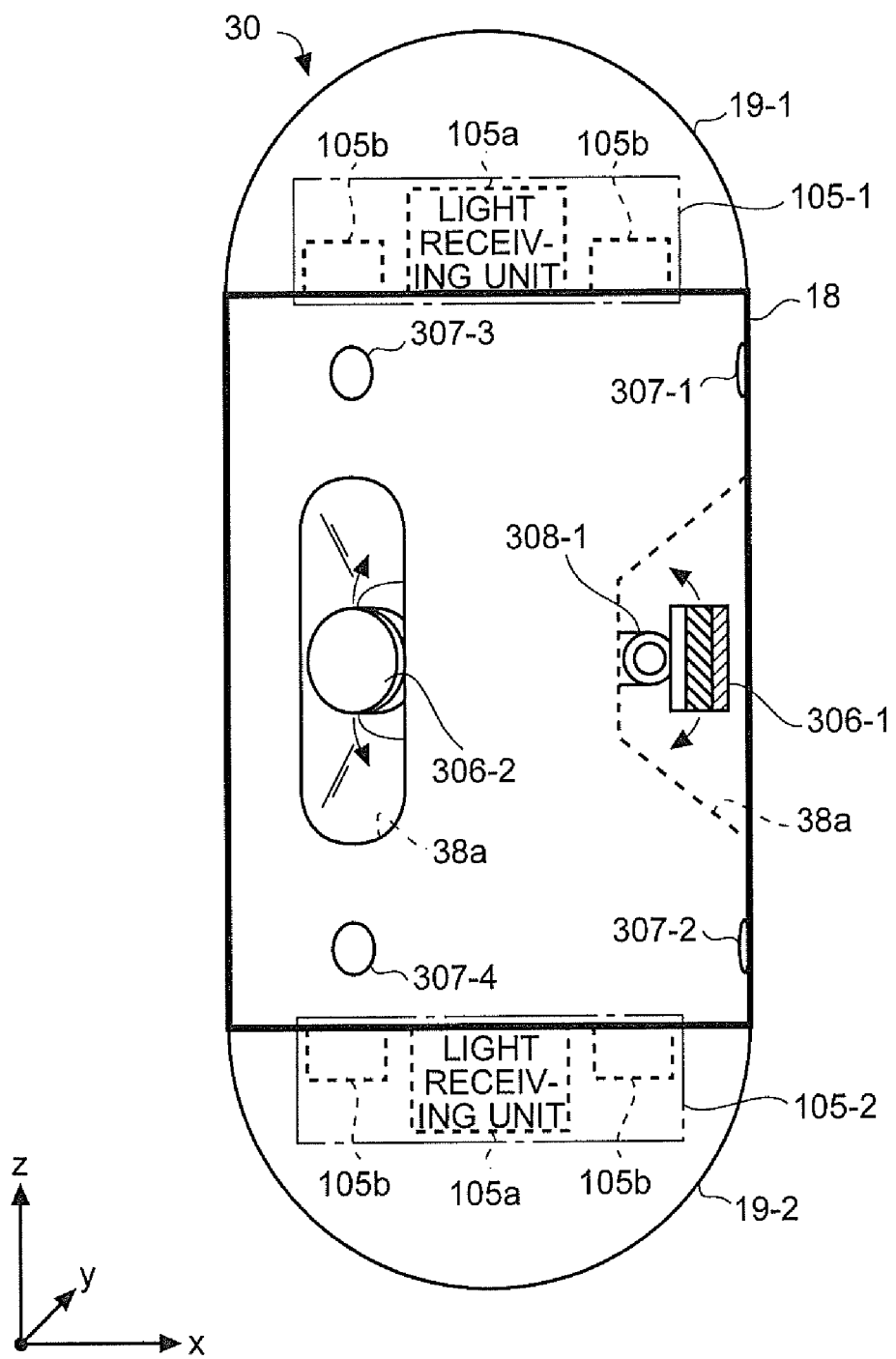
FIG. 28A is an external view (No. 1) showing a schematic configuration of a capsule medical device according to a third embodiment of the invention.
Figure 28B:
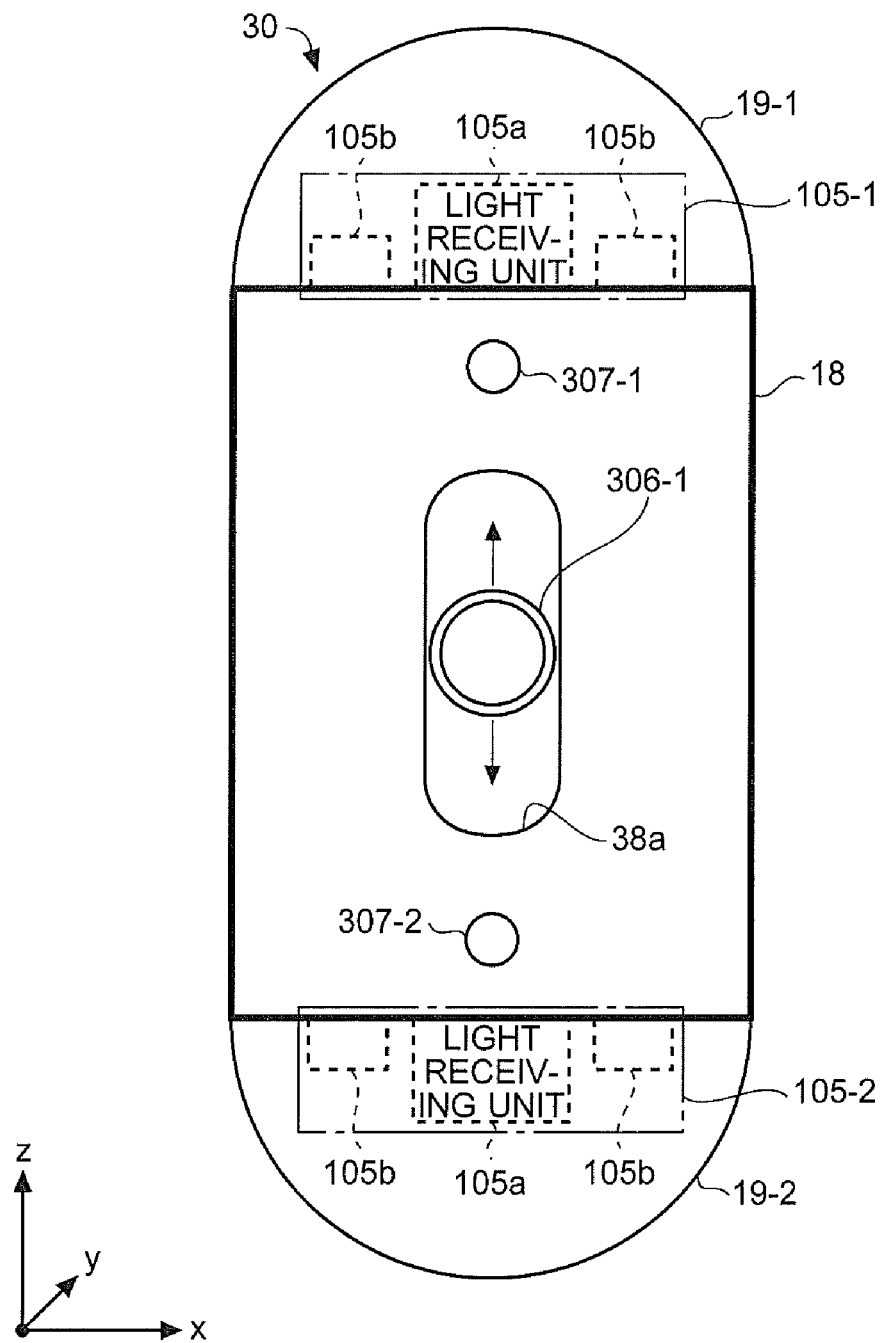
FIG. 28B is an external view (No. 2) showing a schematic configuration of the capsule medical device according to the third embodiment of the invention.
Figure 29:
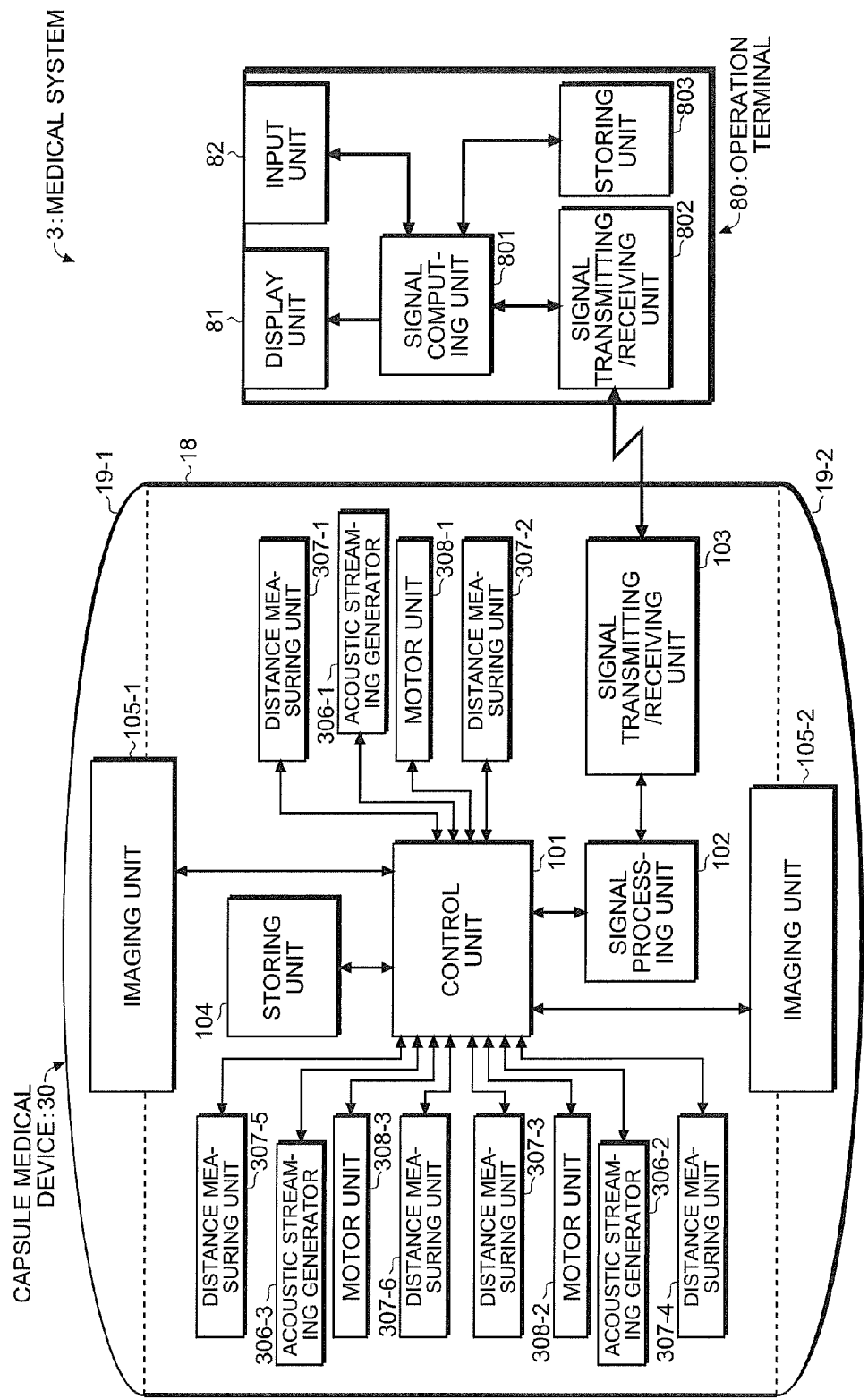
FIG. 29 is a block diagram showing a schematic configuration of a medical system made by the capsule medical device according to the third embodiment of the invention and an operation terminal connected to the capsule medical device via radio waves.
Figure 30:
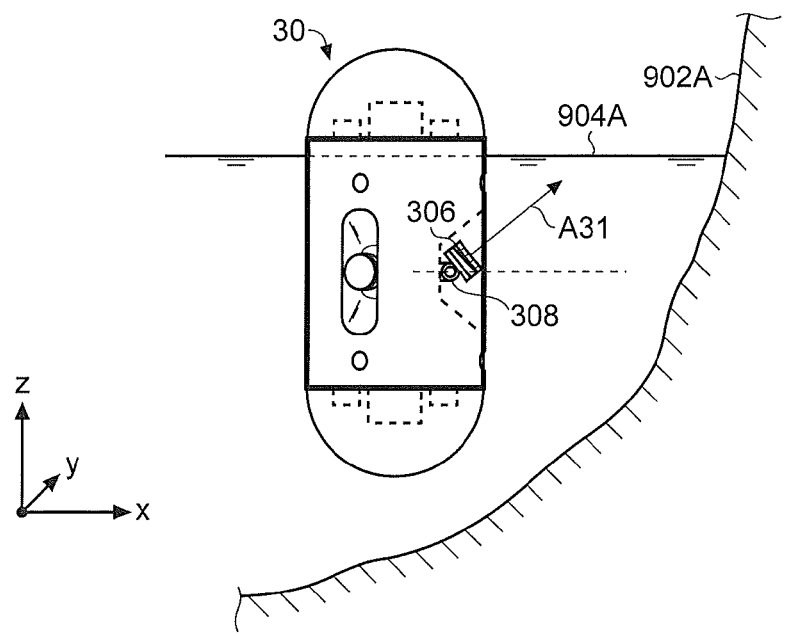
FIG. 30 is a schematic view for explaining movement of the capsule medical device according to the third embodiment of the invention.
Figure 31:
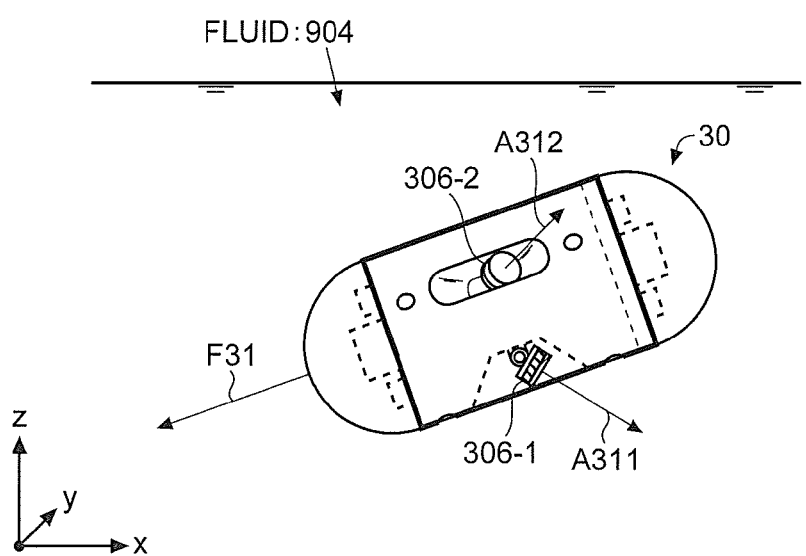
FIG. 31 is a schematic view for explaining another movement of the capsule medical device according to the third embodiment of the invention.

FIGS. 28A and 28B are external views each showing a schematic configuration of a capsule medical device 30 according to the third embodiment. The view angles in FIGS. 28A and 28B are different from each other by 90°. FIG. 29 is a block diagram showing a schematic configuration of the medical system 3 made by the capsule medical device 30 according to the third embodiment and the operation terminal 80 connected to the capsule medical device 30 via radio waves. FIG. 30 is a schematic view for explaining movement of the capsule medical device 30 according to the third embodiment. FIG. 31 is a schematic view for explaining another movement of the capsule medical device 30 according to the third embodiment.

Capsule Medical Device

As shown in FIGS. 28A, 28B, and 29, for example, like the acoustic streaming generators 106-1 to 106-3 in the upper stage in the first embodiment of the invention, the capsule medical device 30 has three acoustic streaming generators 306-1 to 306-3 disposed so that acoustic streaming axes are deviated by 120°, three motor units (acoustic streaming generation direction changing units) 308-1 to 308-3 making the three acoustic streaming generators 306-1 to 306-3 movable in the vertical directions, respectively; and total six distance measuring units 307-1 to 307-6 disposed on the upper and lower sides of the acoustic streaming generators 306-1 to 306-3. The invention is not limited to the motor units but may employ motor units making the acoustic streaming generators movable in the vertical and/or horizontal directions. In the following description, the reference numeral of arbitrary one of the acoustic streaming generators 306-1 to 306-3 will be 306, that of the motor units 308-1 to 308-3 will be 308, and that of the distance measuring units 307-1 to 307-6 will be 307.

The three acoustic streaming generators 306-1 to 306-3 are disposed in an almost center part in the body portion 18 of the capsule medical device 30. As described above, the distance measuring units 307-1 to 307-6 are disposed on the upper and lower sides of the acoustic streaming generators 306-1 to 306-3. Therefore, in the embodiment, the distance between the side face of the capsule medical device 30 on the upper side of the acoustic streaming generators 306-1 to 306-3 and the object and the distance between the side face of the capsule medical device 30 on the lower side and the object can be obtained by using the distance measuring units 307-1 to 307-6.

In the body portion 18 of the casing of the capsule medical device 30, trenches 38a are provided along the flows of the acoustic streaming generated by the acoustic streaming generators 306 which can be swung by the motor units 308.

In the embodiment, by driving and controlling the motor unit 308, the acoustic streaming axis A31 of the acoustic streaming generator 306 is oriented so that the distance to the object (object distance) can be assured on both of the upper and lower sides of the acoustic streaming generator 306 which is driven as shown in FIG. 30. By driving the acoustic streaming generator 306 in this state, the capsule medical device 30 is moved.

In the embodiment, the motor unit 308 is driven and controlled to make the acoustic streaming axes A311, A312, . . . of the one or more acoustic streaming generators 306-1, 306-2, . . . tilt with respect to the capsule medical device 30, or to make an output change as necessary, thereby enabling a propulsion force F31 to be generated in any directions in the fluid 904 as shown in FIG. 31. Therefore, the capsule medical device 30 which can be freely moved in the fluid 904 can be realized. Since the other configuration is similar to that of the first or second embodiment of the invention, its detailed description will not be repeated.

Operation

Figure 32:
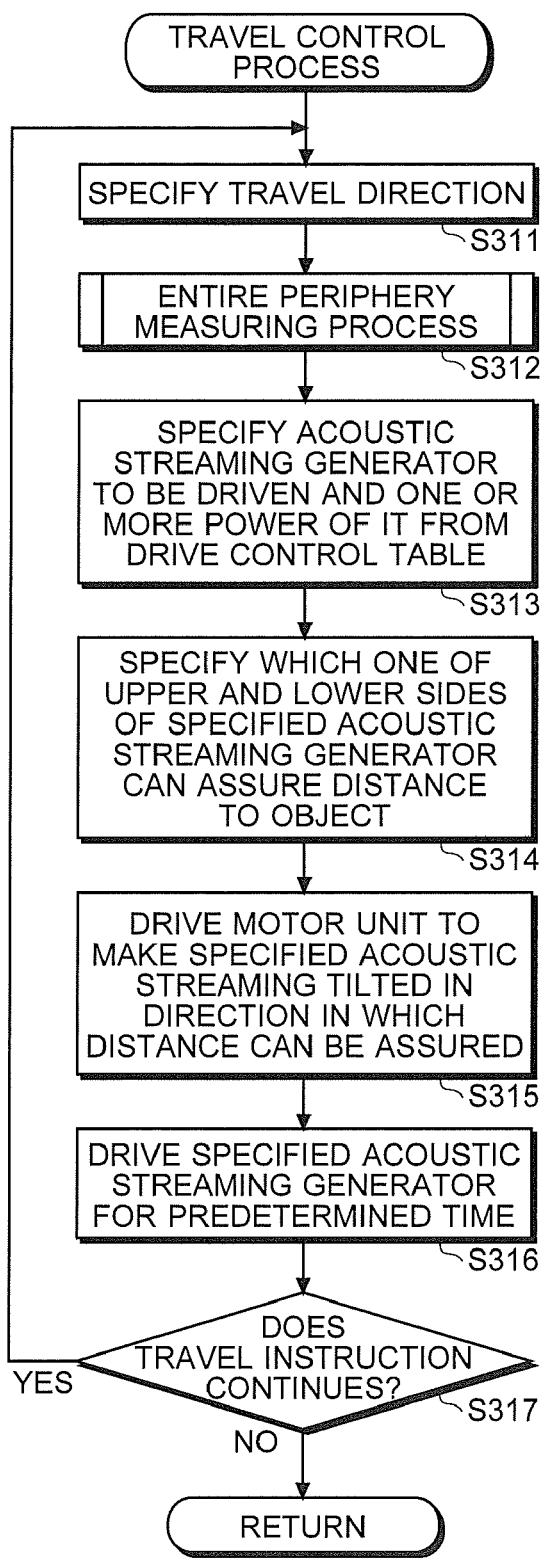
FIG. 32 is a flowchart showing an example of operations in a travel controlling process according to the third embodiment of the invention.
Figure 33:
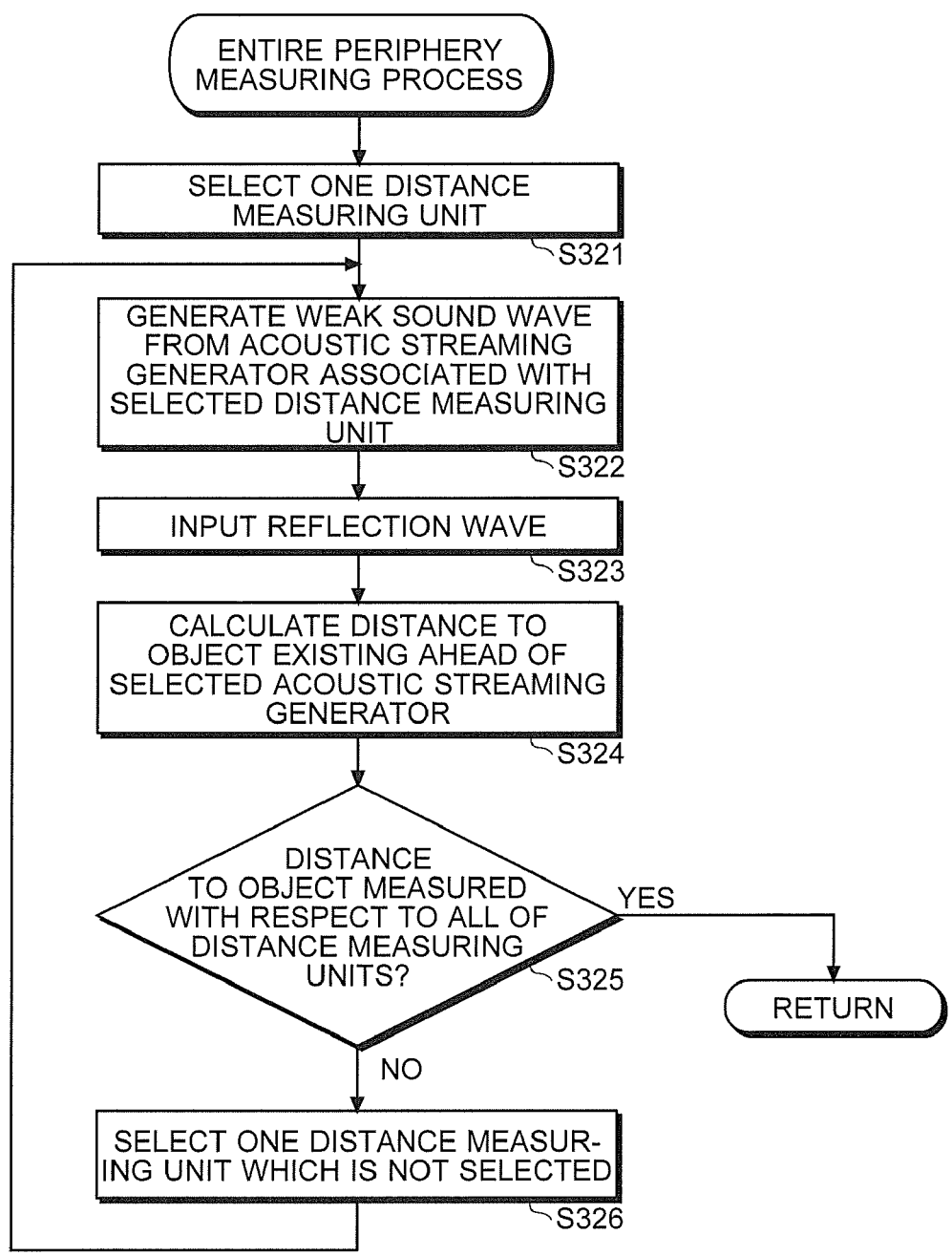
FIG. 33 is a flowchart showing an example of operations in an entire periphery measuring process according to the third embodiment of the invention.

The operation performed at the time of operating the capsule medical device 30 by using the operation terminal 80 in the embodiment will be described in detail with reference to the drawings. FIG. 32 is a flowchart showing an example of operations in the travel controlling process according to the embodiment. FIG. 33 is a flowchart showing an example of operations in the entire periphery measuring process according to the embodiment. Since the general operation at the time of operating the capsule medical device 30 by using the operation terminal 80 in the third embodiment are similar to those described with reference to FIG. 7 in the first embodiment of the invention, their detailed description will not be repeated here.

Travel Control Process

As shown in FIG. 32, in the travel control process (step S103 in FIG. 7) of the embodiment, first, the control unit 101 specifies the travel direction of the capsule medical device 30 instructed by the travel instruction (step S311). Next, the control unit 101 executes the entire periphery measuring process for obtaining the distance to an object in the entire periphery of the capsule medical device 30 by, for example, sequentially driving all of the distance measuring units 307 (step S312). The details of the entire periphery measuring process will be described later with reference to FIG. 33.

Next, the control unit 101 specifies the acoustic streaming generator 306 (its ID) which enables travel in the direction specified as the travel direction in step S311 and one or more powers (power information) to be given at the time of driving the acoustic streaming generators 306 from a drive control table (step S313). Since the drive control table in the embodiment can have only upper-stage control information in the drive control table shown in FIG. 11, its detailed description will not be repeated here. The invention is not limited to the configuration but may employ a configuration of specifying the acoustic streaming generator to be driven in accordance with the instructed direction and computing the power at the time of driving the acoustic streaming generator each time.

Next, the control unit 101 specifies which of the upper and lower sides of the specified acoustic streaming generator 306 can assure the distance to the object (object distance), that is, which one of the distance from the upper side of the specified acoustic streaming generator 306 to the object and the distance from the lower side of the specified acoustic streaming generator 306 to the object is longer (step S314). The object distance may be obtained by, for example, specifying the distance on the upper side of the acoustic streaming generator 306 and the distance on the lower side from the periphery distance obtained by the entire periphery measuring process in step S312 or re-driving the acoustic streaming generator 306 and two distance measuring units 307 associated with the acoustic streaming generator 306.

Next, by driving the motor unit 308, the control unit 101 makes the direction of the acoustic streaming generator 306 tilt to the side (upper or lower side) specified in step S314 (step S315) and drives the specified acoustic streaming generator 306 for predetermined time in this state (step S316). By the operation, a propulsion force in the travel direction is given to the capsule medical device 30. When the distance between the acoustic streaming generator 306 to be driven and the object is sufficiently assured (for example, the distance D1 or longer is assured), without changing the direction of the acoustic streaming generator 306 to up or down, the acoustic streaming generator 306 may be driven in a state where it is oriented in the horizontal direction.

As described above, when the specified acoustic streaming generator 306 is driven to give the propulsion force in the travel direction to the capsule medical device 30, the control unit 101 determines whether the travel instruction is continuously received from the operation terminal 80 (step S317). When the travel instruction is continuously received (Yes at step S317), the control unit 101 returns to step S311 and repeats the following operation. On the other hand, when the travel instruction is not continuously received (No at step S317), the control unit 101 returns to the general operation in FIG. 7. When the propulsion force is given to the capsule medical device 30 and the distance between the acoustic streaming generator 306 to be driven and the object existing in the direction of the acoustic streaming generator 306 is sufficiently assured (for example, the distance D1 or longer), the orientation of the acoustic streaming generator 306 is reset to the horizontal direction and driving is performed.

As described above, the capsule medical device 30 as the capsule propulsion device according to the embodiment, which is introduced in a space (the stomach 902) in which a medium for transmitting a sound wave exist, includes: a plurality of acoustic streaming generators 306-1 to 306-3 for generating acoustic streaming as a flow of the a medium in the stomach 902; the distance obtaining unit (the distance measuring units 307-1 to 307-6 and the control unit 101) for obtaining an object distance between the acoustic streaming generators 306-1 to 306-3 and the object (stomach wall 902A) existing in the direction of the flow of the acoustic streaming generated by the acoustic streaming generators 306-1 to 306-3; and the control unit 101, when the capsule medical device 30 comes close to the stomach wall 902A, for performing driving and control to generate acoustic streaming in a direction in which the distance to the stomach wall 902A is assured by changing the direction of one or more acoustic streaming generator 306. With the configuration, the capsule medical device 30 capable of traveling in a desired direction regardless of the position and orientation in the subject 900 and the medical system 3 having the same can be realized.

Entire Periphery Measuring Process

The entire periphery measuring process shown in step S312 in FIG. 32 will be described in detail with reference to the drawings. FIG. 33 is a flowchart showing the flow of the entire periphery measuring process according to the embodiment.

As shown in FIG. 33, in the entire periphery measuring process (step S312 in FIG. 32), first, the control unit 101 selects any one of the distance measuring units 307-1 to 307-6 (step S321), makes the acoustic streaming generator 306 associated with the selected distance measuring unit 307 generate a weak sound wave (step S322), and receives a reflection wave of the sound wave by the distance measuring unit 307 (step S323). Next, on the basis of the difference between the timing at which the acoustic streaming generator 306 is made output the sound wave and the timing at which the distance measuring unit 307 detects the reflection wave, the control unit 101 calculates the distance from the selected distance measuring unit 307 to an object ahead, that is, the distance to the object from the upper/lower side of the acoustic streaming generator 306 (step S324). At the time of outputting the sound wave for distance measurement, the motor unit 308 may be driven to make the direction of the acoustic streaming generator 306 tilt toward the selected distance measuring unit 307.

Next, the control unit 101 determines whether the distance to the object is calculated with respect to all of the distance measuring units 307 (step S325). In the case of "No" (No at step S325), the control unit 101 selects one of the distance measuring units 307 which are not selected (step S326), after that, returns to step S322, and repeats the subsequent operations until the distance to the object is calculated with respect to all of the distance measuring units 307. On the other hand, when the distance to the object is calculated with respect to all of the distance measuring unit 307 (Yes at step S325), the control unit 101 returns to the travel control process in FIG. 32.

As described above, by calculating the distance from the upper and lower sides of each of the acoustic streaming generators 306 to an object by using the sound wave emitted from the acoustic streaming generators 306 disposed along the entire periphery of the capsule medical device 30, the distances (periphery distance) to the object from the entire periphery of the capsule medical device 30 can be obtained.

Object Distance Assuring Process

Figure 34:
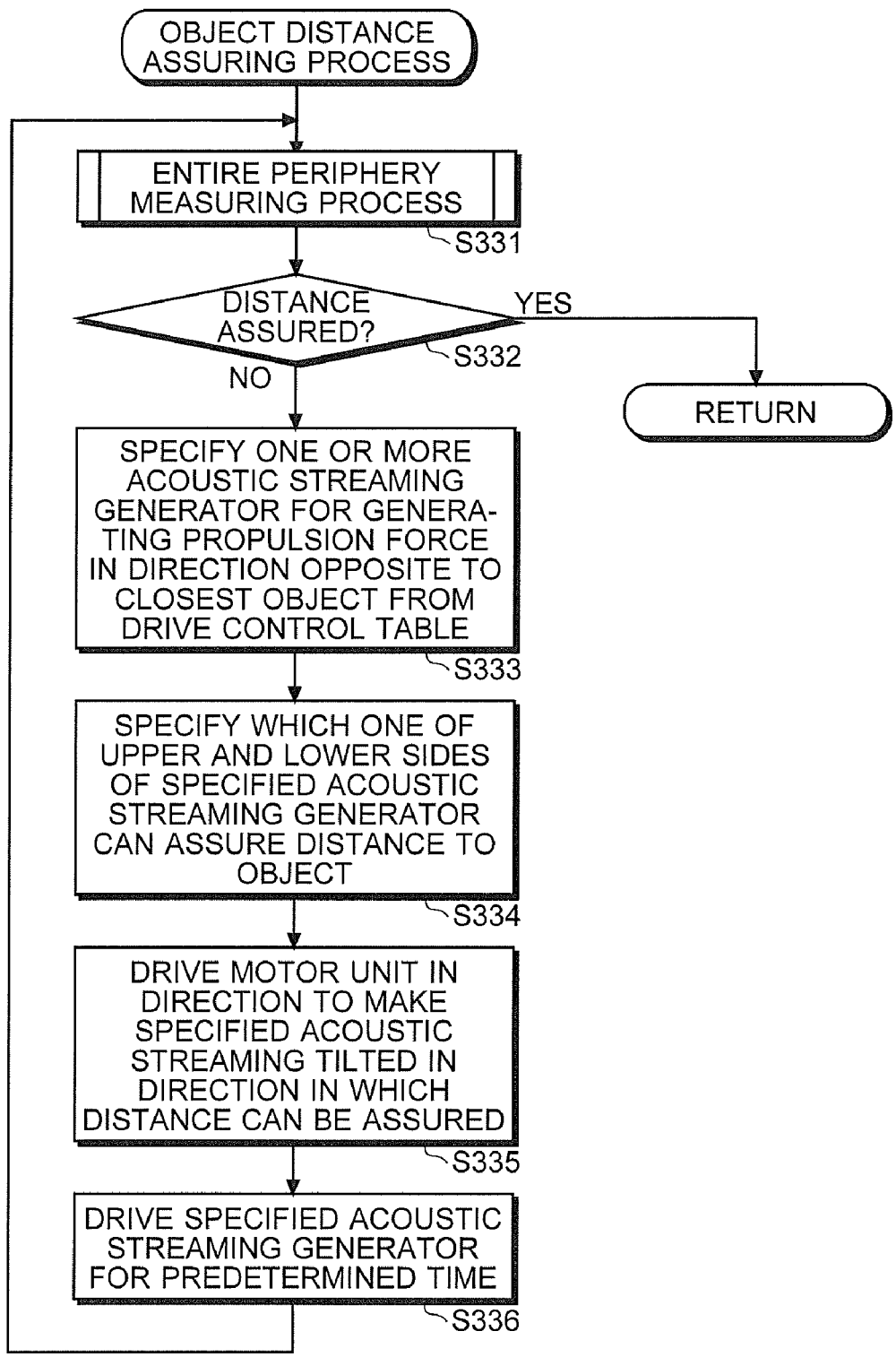
FIG. 34 is a flowchart showing an example of operations in an object distance assuring process according to the third embodiment of the invention.

Also in the fifth modification, in a manner similar to the first embodiment of the invention, the object distance assuring process may be periodically executed in the flow of the general operation (refer to FIG. 7). FIG. 34 is a flowchart showing the flow of the object distance assuring process according to the embodiment.

As shown in FIG. 34, in the object distance assuring process according to the embodiment, first, the control unit 101 sequentially drives, for example, all of the distance measuring units 307, thereby executing an entire periphery measuring process similar to the operation shown in FIG. 33 (step S331).

Next, the control unit 101 determines whether a predetermined threshold (distance D1) or larger is assured as the distance to the object (the stomach wall 902A) in the entire periphery direction of the capsule medical device 30 (step S332). When it is assured (Yes at step S332), the control unit 101 returns to the general operation shown in FIG. 7.

On the other hand, when a direction in which the predetermined threshold or larger is not assured as the distance between the capsule medical device 30 and the object (stomach wall 902A) exists (No at step S332), the control unit 101 specifies one or more of the acoustic streaming generator 306 for generating a propulsion force to the side opposite to the direction in which the capsule medical device 30 comes closest to the object and power (power information) to be given at the time of driving the acoustic streaming generators 306 from the drive control table on the basis of the periphery distance obtained in the entire periphery measuring process in step S331 (step S333). The invention is not limited to the configuration but the acoustic streaming generator 306 to be driven according to the instructed direction and power at the time of driving the acoustic streaming generator 306 may be computed each time.

Subsequently, the control unit 101 specifies which of the upper and lower sides of the specified acoustic streaming generator 306 can assure the distance to the object (object distance), that is, which one of the distance from the upper side of the specified acoustic streaming generator 306 to the object and the distance from the lower side of the specified acoustic streaming generator 306 to the object is longer (step S334). The object distance may be obtained by, for example, specifying the distance on the upper side of the acoustic streaming generator 306 and the distance on the lower side from the periphery distance obtained by the entire periphery measuring process in step S331 or re-driving the acoustic streaming generator 306 and two upper and lower distance measuring units 307 associated with the acoustic streaming generator 306.

Next, by driving the motor unit 308, the control unit 101 makes the direction of the acoustic streaming generator 306 tilt to the side (upper or lower side) specified in step S334 (step S335), drives the specified acoustic streaming generator 306 for predetermined time in this state (step S336) and, after that, returns to step S331. In such a manner, in the embodiment, the distance between the capsule medical device 30 and the object (stomach wall 902A) is maintained to be the predetermined threshold (distance D1) or larger.

By the above operation, in the embodiment, even when the capsule medical device 30 is introduced in the stomach 902 first and the distance to the object (for example, the stomach wall 902A) is shortened, by periodically performing the above-described process in short cycles, the capsule medical device 30 can be moved in a direction according to an input from the operator. In the embodiment, the direction of the acoustic streaming generator 306 can be changed by using the motor unit 308. Consequently, also when the capsule medical device 30 is under the water, the capsule medical device 30 can be moved by driving the acoustic streaming generator 306.

By providing an acoustic streaming generation plane of the acoustic streaming generator 306 with an acoustic lens for diffusing or converging acoustic streaming, the space necessary for generation of acoustic streaming (distance to the object) can be made shorter. As a result, the travel range of the capsule medical device 30 in the space can be made wider. Thus, the capsule medical device 30 can get closer to the stomach wall 902A and more specific in-vivo information can be obtained.

Fourth Embodiment

The configuration and operation of a medical system 4 according to a fourth embodiment of the invention will be described in detail with reference to the drawings. In the following, the same reference numeral is designated to the configuration or operation similar to that of any of the first to third embodiments of the invention in order to simplify explanation, and its detailed description will not be repeated.

Figure 35:
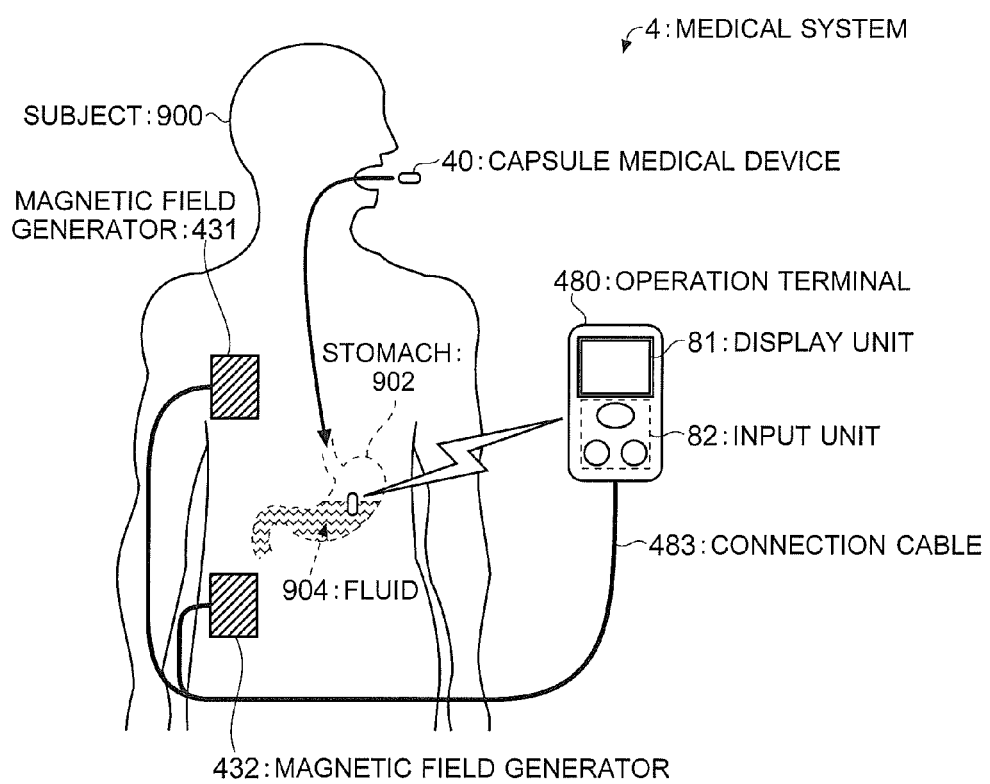
FIG. 35 is a schematic diagram showing a schematic configuration of the medical system according to a fourth embodiment of the invention.
Figure 36:
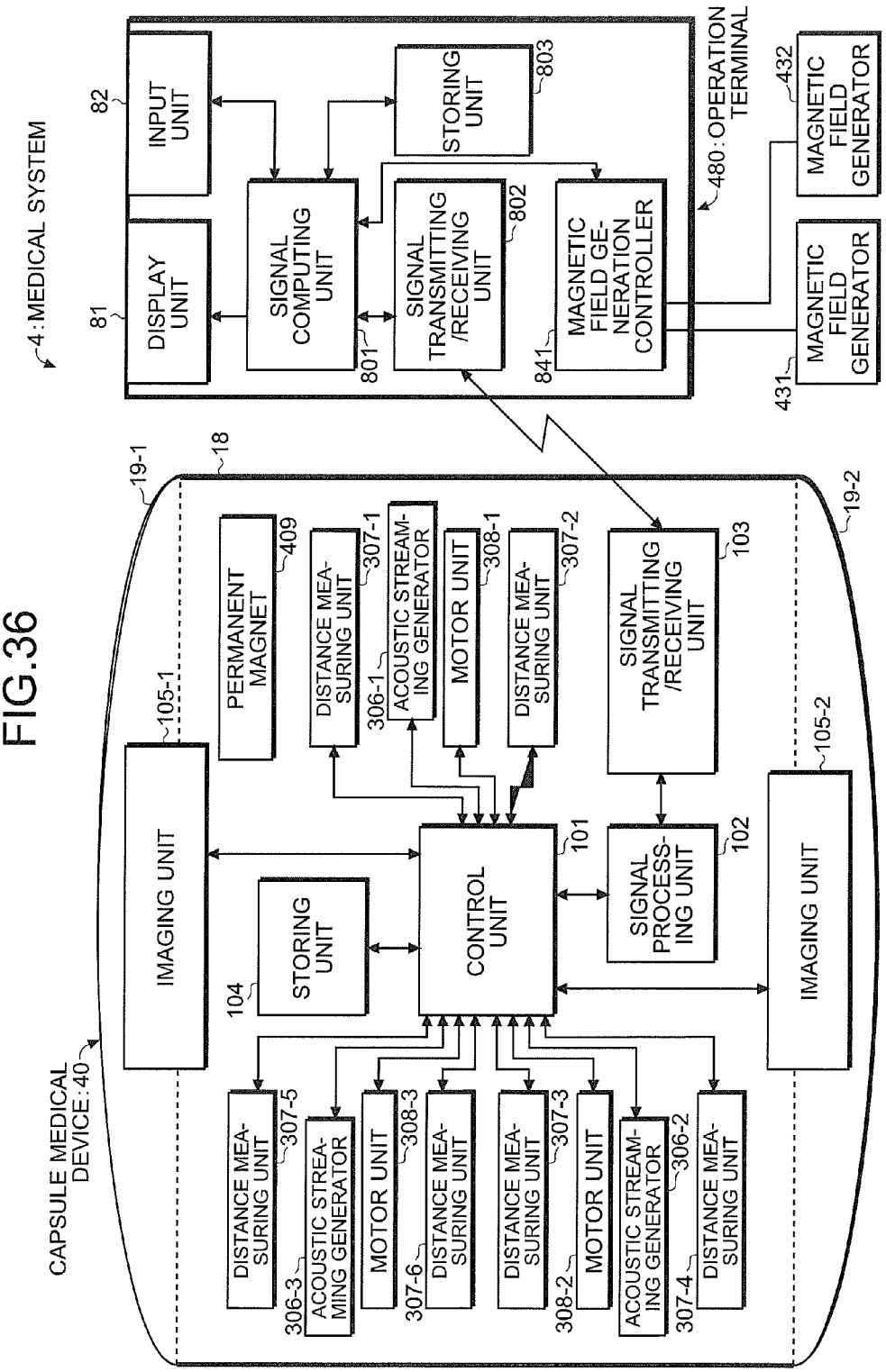
FIG. 36 is a block diagram showing a schematic configuration of a medical system made by the capsule medical device according to the fourth embodiment of the invention and an operation terminal connected to the capsule medical device via radio waves.

FIG. 35 is a schematic view showing a schematic configuration of the medical system 4 according to the embodiment. FIG. 36 is a block diagram showing a schematic configuration of the medical system 4 made by a capsule medical device 40 and an operation terminal 480 connected to the capsule medical device 40 via radio waves.

As shown in FIGS. 35 and 36, the medical system 4 has, in addition to the capsule medical device 40 and the operation terminal 480 which can perform communication with the capsule medical device 40 via radio waves, magnetic field generators 431 and 432 attached to the outside of the subject 900. Each of the magnetic field generators 431 and 432 includes, for example, a coil, when current is passed from the operation terminal 480 connected via a connection cable 483, generates a magnetic field which reaches the capsule medical device 40 in the subject 900.

As shown in FIG. 36, the capsule medical device 40 has, for example, a configuration similar to that of the capsule medical device 30 described in the third embodiment of the invention and has a magnetic field generator such as a permanent magnet 409 fixed to the body portion 18 constructing the casing of the capsule medical device 40. Therefore, the capsule medical device 40 according to the fourth embodiment can control its tilt by making the magnetic field generators 431 and/or 432 attached to the outside of the subject 900. That is, in the embodiment, in addition to the control on the direction of the acoustic streaming generator 306 by the motor unit 308, control on posture of the capsule medical device 40 by the magnetic field generator 431 and/or the magnetic field generator 432 can be realized. With the configuration, in the embodiment, the degree of freedom in the travel of the capsule medical device 40 can be further increased.

Further, the operation terminal 480 is provided with a magnetic field generation controller 841 for supplying current which makes the magnetic field generators 431 and 432 generate magnetic fields in different directions as necessary. The magnetic field generation controller 841 and the magnetic field generators 431 and 432 are connected to each other via the connection cable 483. Since the other configuration is similar to that of any of the first to third embodiments of the invention, the detailed description will not be repeated here.

Operation

Figure 37:
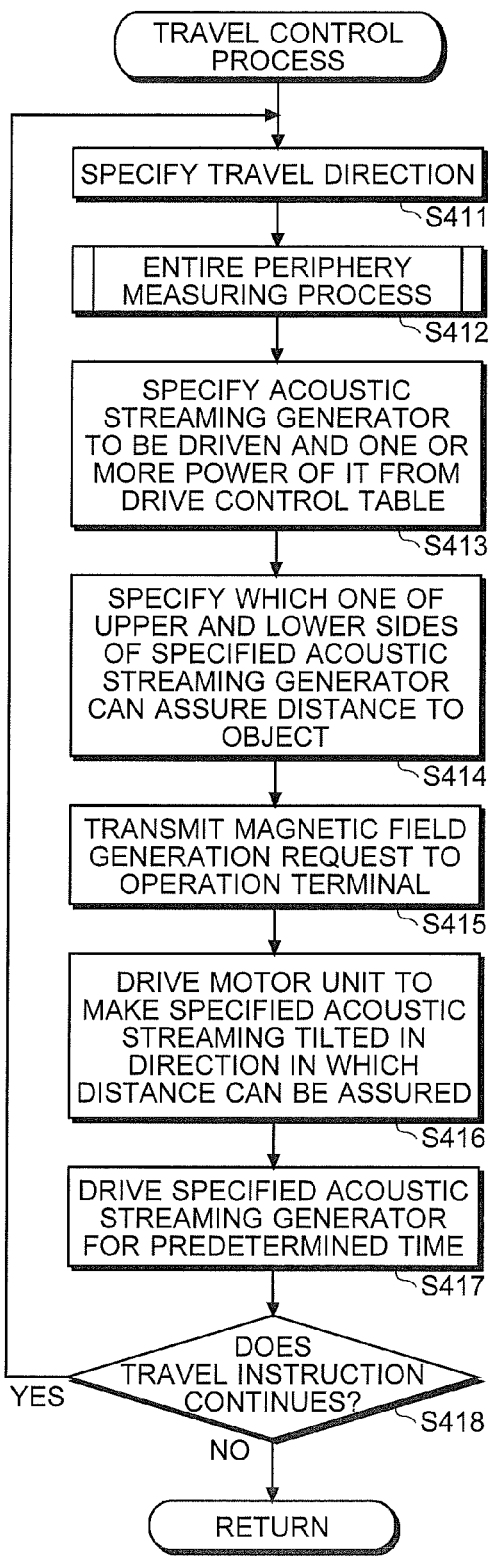
FIG. 37 is a flowchart showing an example of operations in a travel controlling process according to the fourth embodiment of the invention.

The operation performed at the time of operating the capsule medical device 40 by using the operation terminal 480 in the embodiment will be described in detail with reference to the drawings. FIG. 37 is a flowchart showing an example of operations in the travel controlling process according to the embodiment. Since the general operation at the time of operating the capsule medical device 40 by using the operation terminal 480 in the fourth embodiment is similar to that described with reference to FIG. 7 in the first embodiment of the invention, the detailed description will not be repeated here. Since the entire periphery measuring process is similar to that described with reference to FIG. 33 in the third embodiment of the invention, its detailed description will not be repeated.

Travel Control Process

As shown in FIG. 37, in the travel control process (step S103 in FIG. 7) of the embodiment, first, the control unit 101 specifies the travel direction of the capsule medical device 40 instructed by the travel instruction (step S411). Next, the control unit 101 executes an entire periphery measuring process similar to the operation shown in FIG. 33 by, for example, sequentially driving all of the distance measuring units 307 (step S412).

Next, the control unit 101 specifies the acoustic streaming generator 306 (its ID) which enables travel in the direction specified as the travel direction in step S411 and one or more powers (power information) to be given at the time of driving the acoustic streaming generators 306 from a drive control table (step S413). Since the drive control table in the embodiment can have only upper-stage control information in the drive control table shown in FIG. 11, its detailed description will not be repeated here. The invention is not limited to the configuration but may employ a configuration of specifying the acoustic streaming generator 306 to be driven in accordance with the instructed direction and computing the power at the time of driving the acoustic streaming generator 306 each time.

Next, the control unit 101 specifies which of the upper and lower sides of the specified acoustic streaming generator 306 can assure the distance to the object (object distance), that is, which one of the distance from the upper side of the specified acoustic streaming generator 306 to the object and the distance from the lower side of the specified acoustic streaming generator 306 to the object is longer (step S414). The object distance may be obtained by, for example, specifying the distance on the upper side of the acoustic streaming generator 306 and the distance on the lower side from the periphery distance obtained by the entire periphery measuring process in step S412 or re-driving the acoustic streaming generator 306 and two distance measuring units 307 associated with the acoustic streaming generator 306.

Next, the control unit 101 requests the operation terminal 480 to generate a magnetic field for tilting the capsule medical device 40 by attraction of the magnetic field with the permanent magnet 409 in the capsule medical device 40 (magnetic field generation request) (step S415). For example, when the distance on the upper side of the capsule medical device 40 is assured, the control unit 101 requests the operation terminal 480 to generate a magnetic field for tilting the capsule medical device 40 so that the acoustic streaming generator 306 to be driven is directed upward. On the other hand, for example, when the distance on the lower side of the capsule medical device 40 is assured, the control unit 101 requests the operation terminal 480 to generate a magnetic field for tilting the capsule medical device 40 so that the acoustic streaming generator 306 to be driven is directed downward.

By driving the motor unit 308 as necessary, the control unit 101 tilts the direction of the acoustic streaming generator 306 to the side (upper/lower side) specified in step S414 (step S416).

After the direction of the acoustic streaming generator 306 is controlled by using the magnetic field from the outside and the motor unit 308 as described above, the control unit 101 drives the specified acoustic streaming generator 306 for predetermined time (step S417), thereby giving the propulsion force in the travel direction to the capsule medical device 40. When the distance between the acoustic streaming generator 306 to be driven and the object is sufficiently assured (for example, the distance D1 or longer is assured), without changing the direction of the acoustic streaming generator 306 upward/downward or tilting the capsule medical device 40, the driving may be performed in a state where the acoustic streaming generator 306 lies in the horizontal direction.

As described above, when the specified acoustic streaming generator 306 is driven to give the propulsion force in the travel direction to the capsule medical device 40, the control unit 101 determines whether the travel instruction is continuously received from the operation terminal 480 (step 3418). When the travel instruction is continuously received (Yes at step 3418), the control unit 101 returns to step S411 and repeats the following operation. On the other hand, when the travel instruction is not continuously received (No at step 3418), the control unit 101 returns to the general operation in FIG. 7. When the propulsion force is given to the capsule medical device 40 and the distance between the acoustic streaming generator 306 to be driven and the object existing in the direction of the acoustic streaming generator 306 is sufficiently assured (for example, the distance D1 or longer), the direction of the acoustic streaming generator 306 and/or the posture of the capsule medical device 40 may be reset (the acoustic streaming generator 306 is transversely oriented and the capsule medical device 40 is in a perpendicular posture).

As described above, the capsule medical device 40 as the capsule propulsion device according to the embodiment, which is introduced in a space (the stomach 902) in which a medium for transmitting a sound wave exists, includes: a plurality of acoustic streaming generators 306-1 to 306-3 for generating acoustic streaming as a flow of the a medium in the stomach 902; the distance obtaining unit (the distance measuring units 307-1 to 307-6 and the control unit 101) for obtaining an object distance between the acoustic streaming generators 306-1 to 306-3 and the object (stomach wall 902A) existing in the direction of the flow of the acoustic streaming generated by the acoustic streaming generators 306-1 to 306-3; and the control unit 101, when the capsule medical device 40 comes close to the stomach wall 902A, for performing driving and control to generate acoustic streaming in a direction in which the distance to the stomach wall 902A is assured by changing the direction of one or more acoustic streaming generator 306 and changing the tilt of the capsule medical device 30 itself. With the configuration, the capsule medical device 40 capable of traveling in a desired direction regardless of the position and orientation in the subject 900 and the medical system 4 having the same can be realized.

Object Distance Assuring Process

Figure 38:
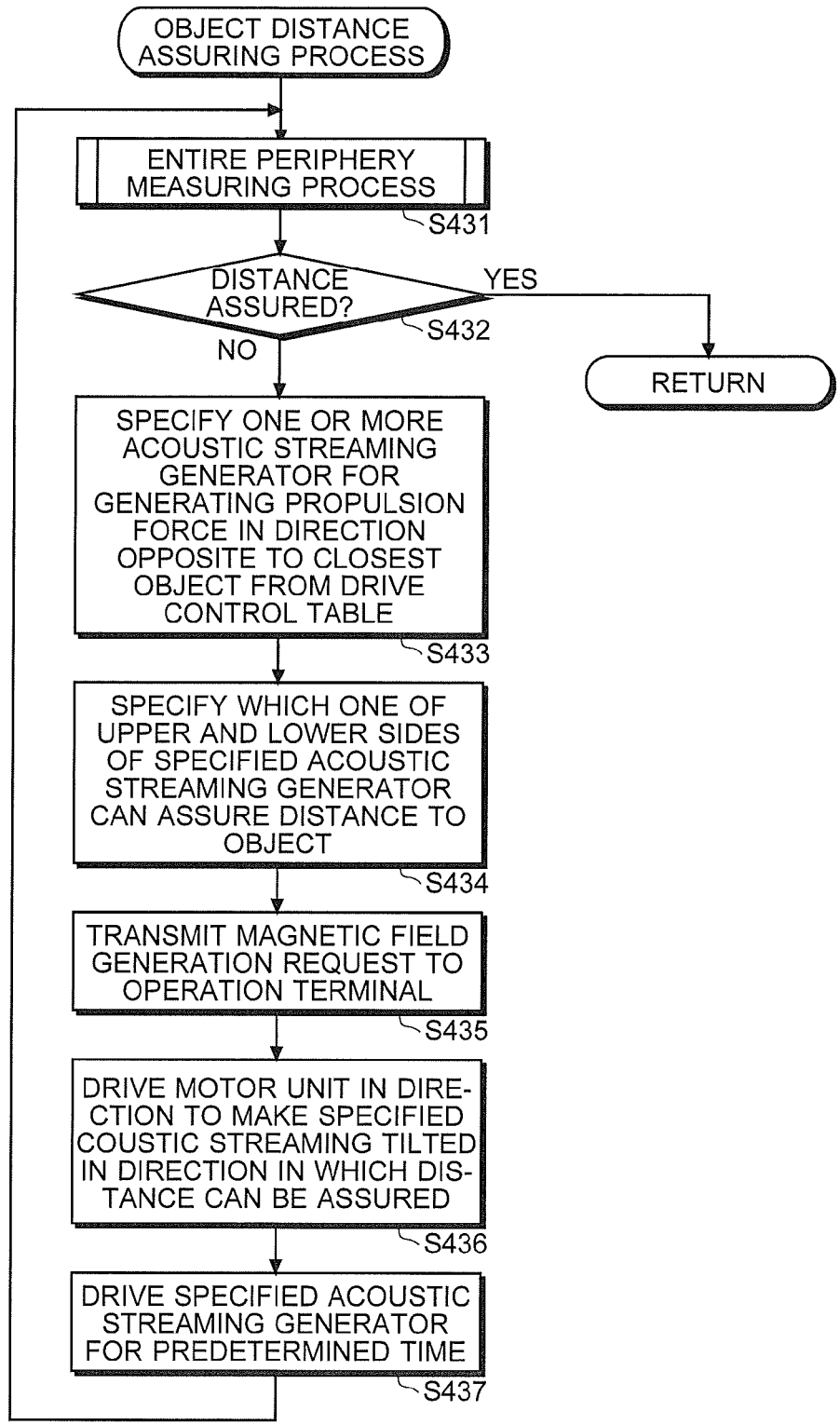
FIG. 38 is a flowchart showing an example of operations in an object distance assuring process according to the fourth embodiment of the invention.

Also in the fourth embodiment, in a manner similar to the first embodiment of the invention, the object distance assuring process may be periodically executed in the flow of the general operation (refer to FIG. 7). FIG. 38 is a flowchart showing the flow of the object distance assuring process according to the embodiment.

As shown in FIG. 38, in the object distance assuring process according to the embodiment, first, the control unit 101 sequentially drives, for example, all of the distance measuring units 307, thereby executing an entire periphery measuring process similar to the operation shown in FIG. 33 (step S431).

Next, the control unit 101 determines whether a predetermined threshold (distance D1) or larger is assured as the distance to the object (the stomach wall 902A) in the entire periphery direction of the capsule medical device 40 (step S432). When it is assured (Yes at step S432), the control unit 101 returns to the general operation shown in FIG. 7.

On the other hand, when a direction in which the predetermined threshold or larger is not assured as the distance between the capsule medical device 40 and the object (stomach wall 902A) exists (No at step S432), the control unit 101 specifies one or more of the acoustic streaming generator 306 for generating a propulsion force to the side opposite to the direction in which the capsule medical device 40 comes closest to the object and power (power information) to be given at the time of driving the acoustic streaming generators 306 from the drive control table on the basis of the periphery distance obtained in the entire periphery measuring process in step S431 (step S433). The invention is not limited to the configuration but the acoustic streaming generator 306 to be driven according to the instructed direction and power at the time of driving the acoustic streaming generator 306 may be computed each time.

Subsequently, the control unit 101 specifies which of the upper and lower sides of the specified acoustic streaming generator 306 can assure the distance to the object (object distance), that is, which one of the distance from the upper side of the specified acoustic streaming generator 306 to the object and the distance from the lower side of the specified acoustic streaming generator 306 to the object is longer (step S434). The object distance may be obtained by, for example, specifying the distance on the upper side of the acoustic streaming generator 306 and the distance on the lower side from the periphery distance obtained by the entire periphery measuring process in step S431 or re-driving the acoustic streaming generator 306 and two upper and lower distance measuring units 307 associated with the acoustic streaming generator 306.

Next, the control unit 101 requests the operation terminal 480 to generate a magnetic field for tilting the capsule medical device 40 by attraction of the magnetic field with the permanent magnet 409 in the capsule medical device 40 (magnetic field generation request) (step S435). For example, when the distance on the upper side of the capsule medical device 40 is assured, the control unit 101 requests the operation terminal 480 to generate a magnetic field for tilting the capsule medical device 40 so that the acoustic streaming generator 306 to be driven is directed upward. On the other hand, for example, when the distance on the lower side of the capsule medical device 40 is assured, the control unit 101 requests the operation terminal 480 to generate a magnetic field for tilting the capsule medical device 40 so that the acoustic streaming generator 306 to be driven is directed downward.

By driving the motor unit 308 as necessary, the control unit 101 tilts the direction of the acoustic streaming generator 306 to the side (upper/lower side) specified in step S434 (step S436).

After the direction of the acoustic streaming generator 306 is controlled by using the magnetic field from the outside and the motor unit 308 as described above, the control unit 101 drives the specified acoustic streaming generator 306 for predetermined time (step S437) and, after that, returns to step S431. In the embodiment, the operation is performed so that the distance between the capsule medical device 40 and the object (stomach wall 902A) is maintained to be the predetermined threshold (distance D1) or larger.

By the above operation, in the embodiment, even when the capsule medical device 40 is introduced in the stomach 902 first and the distance to the object (for example, the stomach wall 902A) is shortened, by periodically performing the above-described process in short cycles, the capsule medical device 40 can be moved in a direction according to an input from the operator. In the embodiment, not only the direction of the acoustic streaming generator 306 can be changed by using the motor unit 308 but also the tilt of the capsule medical device 40 can be changed by using a magnetic field generated by the magnetic field generator 431 and/or the magnetic field generator 432 on the outside. Consequently, also when the capsule medical device 40 is under the water, the capsule medical device 40 can be moved by driving the acoustic streaming generator 306.

By providing an acoustic streaming generation plane of the acoustic streaming generator 306 with an acoustic lens for diffusing or converging acoustic streaming, the space necessary for generation of acoustic streaming (distance to the object) can be made shorter. As a result, the travel range of the capsule medical device 40 in the space can be made wider. Thus, the capsule medical device 40 can get closer to the stomach wall 902A and more specific in-vivo information can be obtained.

Fifth Embodiment

The configuration and operation of a medical system 5 according to a fifth embodiment of the invention will be described in detail with reference to the drawings. In the following, the same reference numeral is designated to the configuration or operation similar to that of any of the first to fourth embodiments of the invention in order to simplify explanation, and its detailed description will not be repeated. In the fifth embodiment, the case of using a configuration similar to that of the medical system 3 in the third embodiment of the invention will be described as an example. However, the invention is not limited to the case but the fifth embodiment can be applied to all of embodiments described here.

Figure 39:
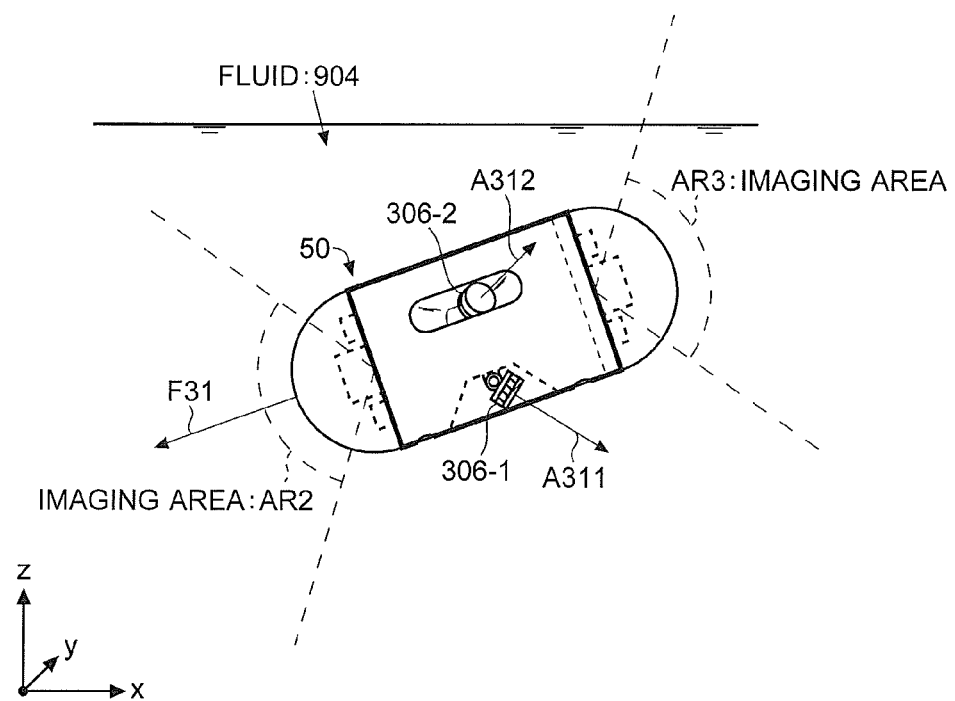
FIG. 39 is a schematic diagram for explaining travel of the capsule medical device according to a fifth embodiment of the invention.
Figure 40:
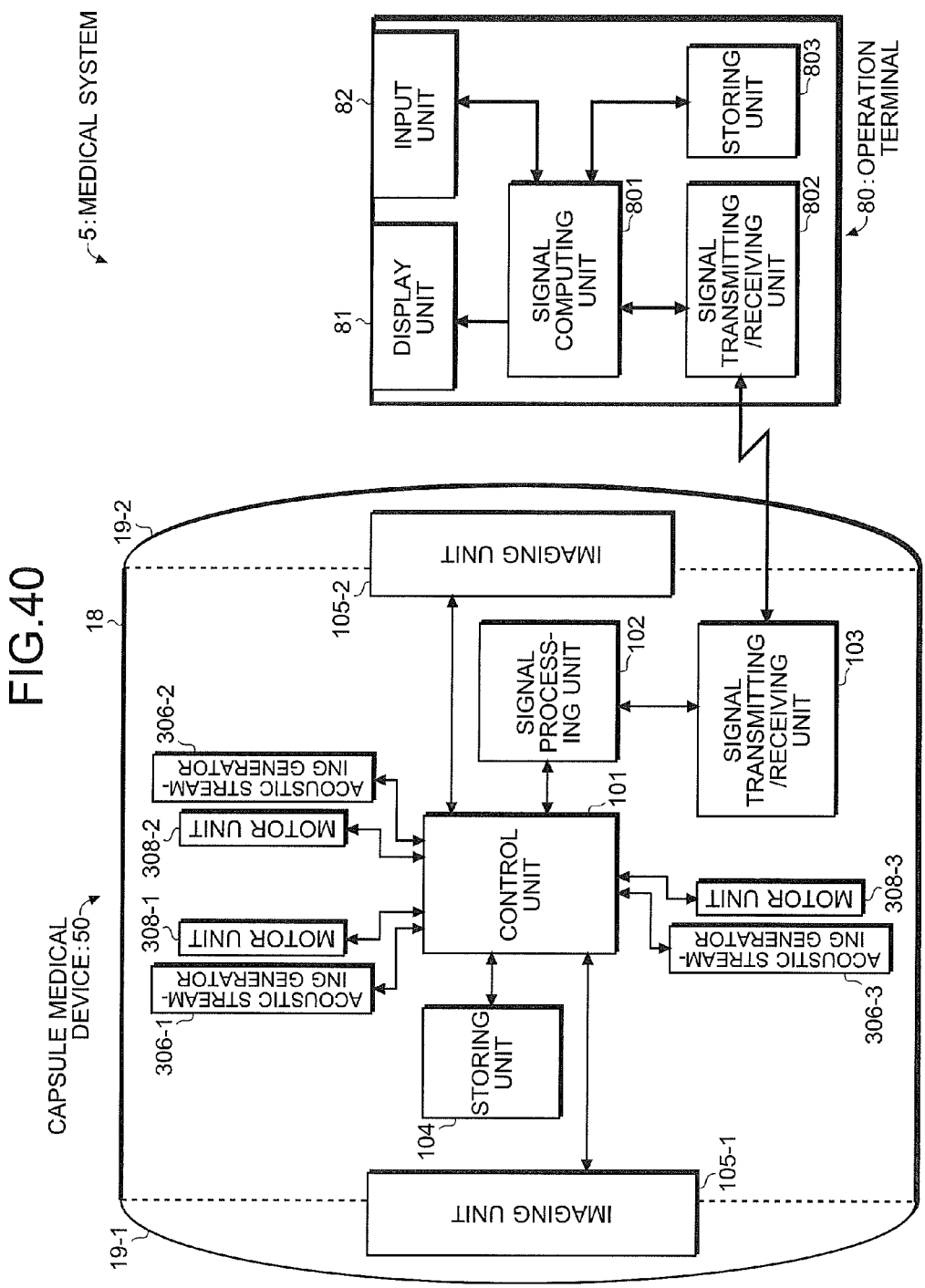
FIG. 40 is a block diagram showing a schematic configuration of the capsule medical device according to the fifth embodiment of the invention and an operation terminal connected to the capsule medical device via radio waves.

FIG. 39 is a schematic view for explaining movement of a capsule medical device 50 according to the fifth embodiment. FIG. 40 is a block diagram showing a schematic configuration of the capsule medical device 50 according to the fifth embodiment of the invention and the operation terminal 80 connected to the capsule medical device 50 via radio waves.

As shown in FIGS. 39 and 40, the capsule medical device 50 of the embodiment can move below the surface of the fluid 904. Consequently, the center of gravity of the capsule medical device 50 of the embodiment leans so that the posture in the fluid 904 is horizontal.

As obvious from comparison between FIGS. 39 and 40 and FIGS. 31 and 29, the capsule medical device 50 of the fifth embodiment has a configuration similar to that of the capsule medical device 30 in the third embodiment of the invention except that the distance measuring unit 307 in the capsule medical device 30 is not provided. Instead, in the fifth embodiment, by analyzing an image captured by the imaging unit 105-1 and/or the imaging unit 105-2, the distance (periphery distance) between the capsule medical device 50 and the object is obtained.

The imaging units 105-1 and 105-2 use, for example, a fish-eye lens as an objective lens and capture images in wide imaging areas AR2 and AR3, respectively. As a method of calculating the distance from the captured image to the object, various methods such as a method using a light amount change can be used. Since the other configuration is similar to any of the first to fourth embodiments, its detailed description will not be repeated here.

Operation

Figure 41:
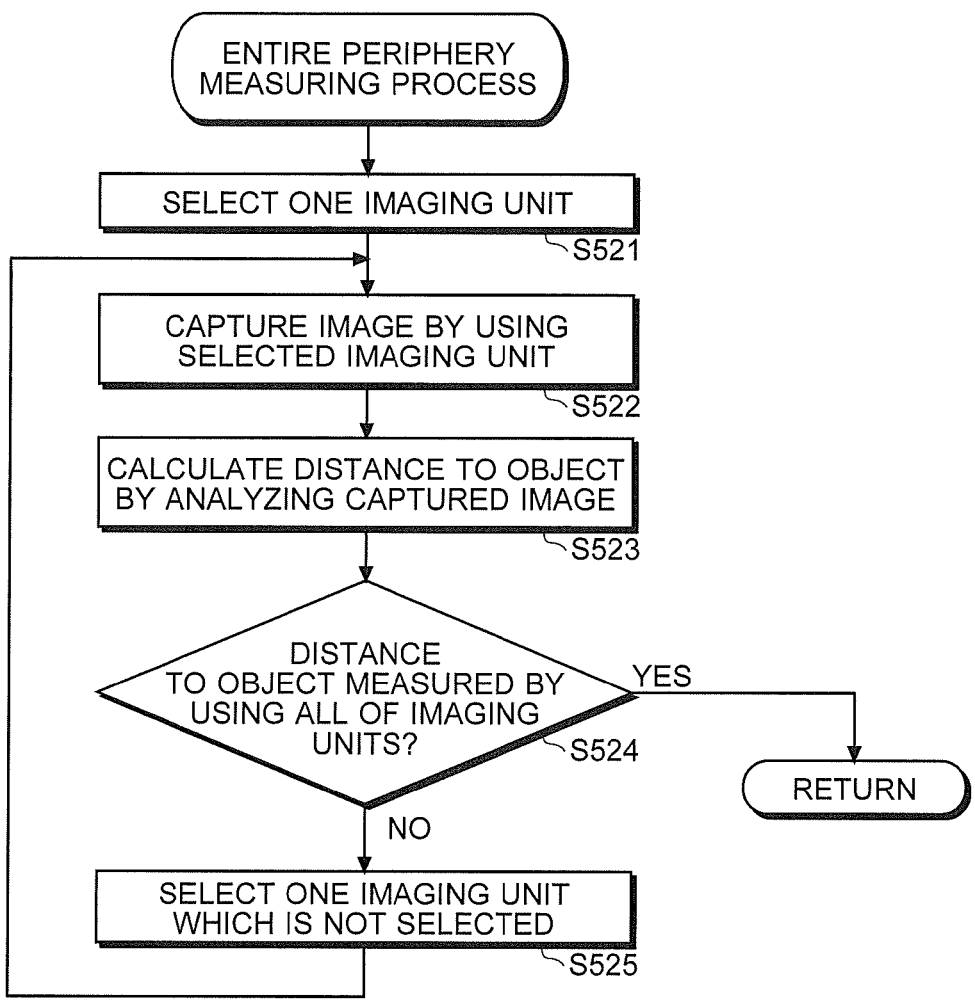
FIG. 41 is a flowchart showing an example of operations in an entire periphery measuring process according to the fifth embodiment of the invention.

The operation performed at the time of operating the capsule medical device 50 by using the operation terminal 80 in the embodiment will be described in detail with reference to the drawings. FIG. 41 is a flowchart showing an example of operations in the entire periphery measuring process according to the embodiment. Since the general operation at the time of operating the capsule medical device 50 by using the operation terminal 80 in the fifth embodiment is similar to that described with reference to FIG. 7 in the first embodiment of the invention, the detailed description will not be repeated here. Since the object distance assuring process and the travel control process are similar to those described with reference to FIGS. 32 and 34 in the third embodiment of the invention, its detailed description will not be repeated.

Entire Periphery Measuring Process

As shown in FIG. 41, in the entire periphery measuring process (step S331 in FIG. 34 and step S312 in FIG. 32) according to the embodiment, first, the control unit 101 selects any one of the imaging units 105-1 and 105-2 (step S521) and obtains an image in the imaging area AR2 or AR3 by using the selected imaging unit 105-1 or 105-2 (step S522). Subsequently, the control unit 101 analyzes the captured image, obtains, for example, a light amount change, and calculates the distance to the object by using the light amount change (step S523).

Next, the control unit 101 determines whether the distance to the object has been calculated by analyzing images captured by all of the imaging units 105-1 and 105-2 (step S524). In the case the distance has not been calculated (No at step S524), the control unit 101 selects one of the imaging units 105-1 and 105-2, which is not selected (step S525), after that, returns to step S522, and repeats the subsequent operations until the distance to the object is calculated by analyzing images captured by all of the imaging units 105-1 and 105-2. On the other hand, when the distance has been calculated (Yes at step S524), the control unit 101 returns to the travel control process in FIG. 32.

As described above, the capsule medical device 50 as the capsule propulsion device according to the embodiment, which is introduced in a space (the stomach 902) in which a medium for transmitting a sound wave exist, includes: a plurality of acoustic streaming generators 306-1 to 306-3 for generating acoustic streaming as a flow of the a medium in the stomach 902; the distance obtaining unit (the imaging units 105-1 and 105-2 and the control unit 101) for obtaining an object distance between the acoustic streaming generators 306-1 to 306-3 and the object (stomach wall 902A) existing in the direction of the flow of the acoustic streaming generated by the acoustic streaming generators 306-1 to 306-3; and the control unit 101 for performing driving and control to make the acoustic streaming generator 306 having an object distance of a predetermined threshold (distance D1) or larger generate acoustic streaming. With the configuration, the capsule medical device 50 capable of traveling in a desired direction regardless of the position and orientation in the subject 900 and the medical system 5 having the same can be realized.

Sixth Embodiment

The configuration and operation of a medical system 6 according to a sixth embodiment of the invention will be described in detail with reference to the drawings. In the following, the same reference numeral is designated to the configuration or operation similar to that of any of the first to fifth embodiments of the invention in order to simplify explanation, and its detailed description will not be repeated. In the sixth embodiment, the case of applying the configuration of the sixth embodiment to the medical system 1 of the first embodiment of the invention will be described as an example. However, the invention is not limited to the case. The sixth embodiment can be applied to all of the embodiments illustrated in the description.

Figure 42:
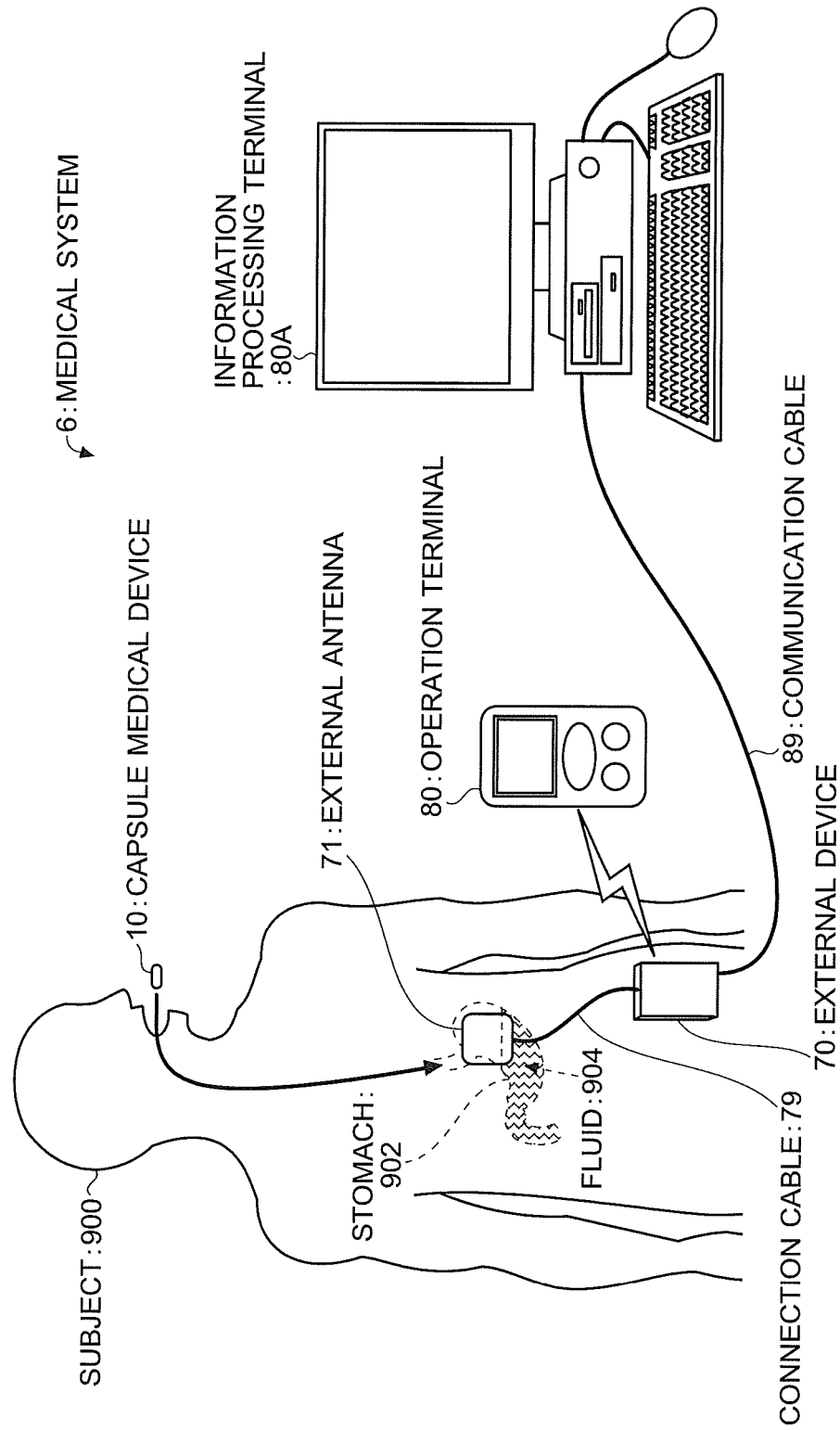
FIG. 42 is a schematic diagram showing a schematic configuration of the medical system according to a sixth embodiment of the invention.

FIG. 42 is a schematic diagram showing a schematic configuration of the medical system 6 according to the sixth embodiment of the invention. As shown in FIG. 42, the medical system 6 is constructed so that the operation terminal 80 according to the first embodiment of the invention performs radio communication with the capsule medical device 10 introduced in the subject 900 via an external device 70 fixed on the outside of the subject 900.

An external antenna 71 is connected to the external device 70 via a connection cable 79, and electric waves emitted from the external antenna 71 are received by the capsule medical device 10. The electric waves output from the capsule medical device 10 are received by the external antenna 71 and supplied to the external device 70.

The external device 70 can perform communication with the operation terminal 80, for example, via radio waves. The invention is not limited to the configuration. The external device 70 may be connected to the operation terminal 80 by a wired circuit.

In addition, to the external device 70, an information processing terminal 80A such as a personal computer can be connected via a communication cable 89 such as a Local Area Network (LAN) cable or a Universal Serial Bus (USB) cable. With the configuration, for example, the capsule medical device 10 can be operated from the information processing terminal 80A in place of the operation terminal 80.

The external antenna 71, the external device 70, the operation terminal 80, and the information processing terminal 80A in the above configuration are external devices in the embodiment. By providing one or more of them, the capsule medical device 10 in the subject 900 can be operated. Since the other configuration and operation are similar to those of any of the first to fifth embodiments of the invention, the detailed description will not be repeated here.

As described above, the capsule medical device 10 as the capsule propulsion device according to the embodiment, which is introduced in a space (the stomach 902) in which a medium for transmitting a sound wave exists, includes: a plurality of acoustic streaming generators 106-1 to 106-6 for generating acoustic streaming as a flow of the a medium in the stomach 902; the distance obtaining unit (the distance measuring units 107-1 and 107-6 and the control unit 101) for obtaining an object distance between the acoustic streaming generators 106-1 to 106-6 and the object (stomach wall 902A) existing in the direction of the flow of the acoustic streaming generated by the acoustic streaming generators 106-1 to 106-6; and the control unit 101 for performing driving and control to make the acoustic streaming generator 106 having an object distance of a predetermined threshold (distance D1) or larger generate acoustic streaming. With the configuration, the capsule medical device 10 capable of traveling in a desired direction regardless of the position and orientation in the subject 900 and the medical system 6 having the same can be realized.

The foregoing embodiments are just examples for carrying out the present invention, and the present invention is not limited to the embodiments and various modifications according to specifications and the like are within the scope of the present invention. It is obviously understood from the above description that other various embodiments are possible within the range of the present invention.

The above and other features, advantages and technical and industrial significance of this invention will be better understood by reading the following detailed description of presently preferred embodiments of the invention, when considered in connection with the accompanying drawings.

What is claimed is:

1. A capsule propulsion device which is introduced in a space in which a medium for transmitting a sound wave exists, the capsule propulsion device comprising:
    at least one acoustic streaming generator that generates acoustic streaming as a flow of the medium in the space;
    a control unit that drives and controls the at least one acoustic streaming generator;
    a distance obtaining unit that obtains an object distance between one of the at least one acoustic streaming generator and an object existing in the space; and
    an input receiving unit that receives an input in a travel direction of the capsule propulsion device in the space in accordance with an operation instruction input by an operation instruction input unit that is separated from the capsule propulsion device,
    wherein the control unit drives and controls the at least one acoustic streaming generator on the basis of the distance information obtained by the distance obtaining unit, and
    the control unit specifies one or more acoustic streaming generator to be driven for travel in the travel direction in accordance with an operation signal transmitted corresponding to the operation instruction input by the operation instruction input unit and, when an object distance obtained by the distance obtaining unit is less than a predetermined threshold that is defined in advance to be a distance required for generating the acoustic streaming between the specified one or more acoustic streaming generator and the object, the control unit stops driving of the specified specified one or more acoustic streaming generator.

2. The capsule propulsion device according to claim 1, wherein the control unit specifies at least one acoustic streaming generator for travel in a direction opposite to the travel direction and drives it for predetermined time.

3. The capsule propulsion device according to claim 1,
    wherein the at least one acoustic streaming generator includes at least one first acoustic streaming generator that gives a propulsion force to the capsule propulsion device by generating acoustic streaming and at least one second acoustic streaming generator that gives a rotational force to the capsule propulsion device by generating acoustic streaming, and
    the control unit drives the second acoustic streaming generator, assuring the object distance obtained by the distance obtaining unit, which is equal to or larger than the predetermined threshold, to turn the capsule propulsion device, and controls so that the object distance between the one of the at least one first acoustic streaming generator and the object becomes the predetermined threshold or larger.

4. The capsule propulsion device according to claim 1,
    wherein the control unit specifies at least one first acoustic streaming generator for travel in the travel direction and, when an object distance between the first acoustic streaming generator and the object, obtained by the distance obtaining unit is less than the predetermined threshold, the control unit specifies at least one second acoustic streaming generator assuring a distance to the object for travel in a direction away from the object, wherein the distance is the predetermined threshold or larger to drive and control the second acoustic streaming generator.

5. The capsule propulsion device according to claim 1,
    wherein the control unit specifies at least one first acoustic streaming generator for travel in the travel direction and, when an object distance between the first acoustic streaming generator and the object, obtained by the distance obtaining unit is less than a predetermined threshold, the control unit specifies at least one second acoustic streaming generator for travel toward the object to drive and control the second acoustic streaming generator, and stops driving of the second acoustic streaming generator before the capsule propulsion device collides against the object.

6. The capsule propulsion device according to claim 1, further comprising:
    an acoustic streaming generation direction changing unit that changes a direction of generating the acoustic streaming of the acoustic streaming generator,
    wherein the control unit specifies at least one acoustic streaming generator to be driven for travel in the travel direction, and drives and controls the acoustic streaming generation direction changing unit so that an object distance between the specified acoustic streaming generator and the object, obtained by the distance obtaining unit becomes a predetermined threshold or larger, thereby changing the direction of the acoustic streaming generator.

7. The capsule propulsion device according to claim 1, further comprising:
- a magnetic body fixed to the capsule propulsion device; and
- an external magnetic field generator that controls a tilt of the capsule propulsion device by exerting an influence on the magnetic body and makes the acoustic streaming generator generate the acoustic streaming,
- wherein the control unit specifies at least one acoustic streaming generator to be driven for travel in the travel direction, and controls a magnetic field from the external magnetic field generator so that an object distance between the specified acoustic streaming generator and the object, obtained by the distance obtaining unit becomes a predetermined threshold or larger, thereby changing the direction of the acoustic streaming generator.

8. The capsule propulsion device according to claim 1, wherein density of the capsule propulsion device is equal to or less than that of the medium.

9. The capsule propulsion device according to claim 1, wherein the acoustic streaming generator includes:
- a piezoelectric element to which a predetermined resonance frequency is applied;
- a vibration absorbing unit that absorbs a component transmitted to the capsule propulsion device side by vibration generated in the piezoelectric element; and
- an acoustic lens that enhances directionality of a vibration wave output from the piezoelectric element.

10. The capsule propulsion device according to claim 1, wherein the distance obtaining unit is an optical distance measuring sensor including a light emitting unit that outputs light in a direction in which the acoustic streaming generated by the acoustic streaming generator flows, and a light receiving unit that detects light reflected by the object.

11. A method of operating a capsule propulsion device to propel the capsule propulsion device in a medium that transmits a sound wave, the propulsion method comprising:
- an operation instructing step of receiving, by an input receiving unit, an input of operation for instructing a travel direction of the capsule propulsion device;
- a distance measuring step of measuring distance from the capsule propulsion device to an object existing in the medium;
- a determining step of determining, by a control unit, on the basis of the distance to the object measured at the distance measuring step whether the capsule propulsion device can move in a direction instructed in the operation instructing step on the basis of whether the distance to the object measured at the distance measuring step is less than a predetermined threshold that is defined in advance to be a distance required for generating an acoustic streaming between an acoustic streaming generator and the object; and
- an acoustic streaming generating step of causing, by the control unit, at least one acoustic streaming generator in which the distance to the object measured at the distance measuring step is equal to or more than the predetermined threshold to generate acoustic streaming for propelling the capsule propulsion device if it is determined that the capsule propulsion device can move at the determining step.

12. The propulsion method according to claim 11, wherein in the acoustic streaming generating step, a generation direction and output intensity of the acoustic streaming are specified on the basis of the distance to the object measured in the distance measuring step.

13. The propulsion method according to claim 11, wherein in the acoustic streaming generating step, a generation direction and output intensity of the acoustic streaming are specified by referring to an acoustic streaming control table for managing correspondence relations among a travel direction of the capsule propulsion device, the generation direction of the acoustic streaming, and information of output intensity on the basis of the distance to the object measured in the distance measuring step.

* * * * *